(12) United States Patent
Davis et al.

(10) Patent No.: US 9,494,554 B2
(45) Date of Patent: Nov. 15, 2016

(54) CHIP SET-UP AND HIGH-ACCURACY NUCLEIC ACID SEQUENCING

(71) Applicant: Genia Technologies, Inc., Mountain View, CA (US)

(72) Inventors: Randall Davis, Pleasanton, CA (US);
Roger Chen, Saratoga, CA (US);
Arkadiusz Bibillo, Cupertino, CA (US);
Kevin Deierling, Pescadero, CA (US)

(73) Assignee: Genia Technologies, Inc., Santa Clara, CA (US)

( * ) Notice: Subject to any disclaimer, the term of this patent is extended or adjusted under 35 U.S.C. 154(b) by 617 days.

(21) Appl. No.: 13/918,626

(22) Filed: Jun. 14, 2013

(65) Prior Publication Data

US 2014/0034497 A1  Feb. 6, 2014

Related U.S. Application Data

(60) Provisional application No. 61/771,031, filed on Feb. 28, 2013, provisional application No. 61/660,537, filed on Jun. 15, 2012, provisional application No. 61/660,543, filed on Jun. 15, 2012.

(51) Int. Cl.
*G01N 27/447* (2006.01)
*G01N 33/487* (2006.01)
*C12Q 1/68* (2006.01)

(52) U.S. Cl.
CPC ....... *G01N 27/44791* (2013.01); *C12Q 1/6869* (2013.01); *G01N 33/48721* (2013.01)

(58) Field of Classification Search
CPC .............. G01N 27/3275; G01N 27/3278; G01N 33/48721
See application file for complete search history.

(56) References Cited

U.S. PATENT DOCUMENTS

| | | | |
|---|---|---|---|
| 2,656,508 A | 10/1953 | Coulter | |
| 4,121,192 A | 10/1978 | Wilson | |
| 4,859,945 A | 8/1989 | Stokar | |
| 5,198,543 A | 3/1993 | Blanco et al. | |
| 5,302,509 A | 4/1994 | Cheeseman | |
| 5,308,539 A | 5/1994 | Koden et al. | |
| 5,457,342 A | 10/1995 | Herbst, II | |

(Continued)

FOREIGN PATENT DOCUMENTS

| | | |
|---|---|---|
| WO | WO 91/06678 A1 | 5/1991 |
| WO | WO 93/21340 A1 | 10/1993 |

(Continued)

OTHER PUBLICATIONS

Davies, Kevin, The Nanopore Wars: Genia CEO Touts Best of Oxford Nanopore and Ion Torrent. Bio-IT World Feb. 22, 2012.
(Continued)

*Primary Examiner* — J. Christopher Ball
(74) *Attorney, Agent, or Firm* — FisherBroyles, LLP; Victoria L. Boyd

(57) ABSTRACT

The present disclosure provides devices, systems and methods for sequencing nucleic acid molecules. Nucleic acid molecules can be sequenced with a high accuracy (e.g., greater than 97% in a single pass) using a chip comprising an array of independently addressable nanopore sensors at a density of at least about 500 sites per 1 $mm^2$. An individual nanopore sensor can include a nanopore in a membrane that is adjacent or in proximity to a sensing electrode.

15 Claims, 43 Drawing Sheets

(56) References Cited

U.S. PATENT DOCUMENTS

| | | |
|---|---|---|
| 5,569,950 A | 10/1996 | Lewis et al. |
| 5,576,204 A | 11/1996 | Blanco et al. |
| 5,756,355 A | 5/1998 | Lang et al. |
| 5,770,367 A | 6/1998 | Southern et al. |
| 5,795,782 A | 8/1998 | Church et al. |
| 5,804,386 A | 9/1998 | Ju |
| 5,814,454 A | 9/1998 | Ju |
| 5,869,244 A | 2/1999 | Martin et al. |
| 5,876,936 A | 3/1999 | Ju |
| 5,912,155 A | 6/1999 | Chatterjee et al. |
| 5,939,301 A | 8/1999 | Hughes, Jr. et al. |
| 5,952,180 A | 9/1999 | Ju |
| 5,981,733 A | 11/1999 | Gamble et al. |
| 6,012,291 A | 1/2000 | Ema |
| 6,014,213 A | 1/2000 | Waterhouse et al. |
| 6,015,714 A | 1/2000 | Baldarelli et al. |
| 6,046,005 A | 4/2000 | Ju et al. |
| 6,082,115 A | 7/2000 | Strnad |
| 6,210,896 B1 | 4/2001 | Chan |
| 6,217,731 B1 | 4/2001 | Kane et al. |
| 6,232,103 B1 | 5/2001 | Short |
| 6,255,083 B1 | 7/2001 | Williams |
| 6,261,797 B1 | 7/2001 | Sorge et al. |
| 6,265,193 B1 | 7/2001 | Brandis et al. |
| 6,321,101 B1 | 11/2001 | Holmstrom |
| 6,362,002 B1 | 3/2002 | Denison et al. |
| 6,383,749 B2 | 5/2002 | Bochkariov et al. |
| 6,399,320 B1 | 6/2002 | Markau et al. |
| 6,399,335 B1 | 6/2002 | Kao et al. |
| 6,413,792 B1 | 7/2002 | Sauer |
| 6,485,703 B1 | 11/2002 | Cote et al. |
| 6,607,883 B1 | 8/2003 | Frey et al. |
| 6,616,895 B2 | 9/2003 | Dugas et al. |
| 6,627,748 B1 | 9/2003 | Ju et al. |
| 6,664,079 B2 | 12/2003 | Ju et al. |
| 6,673,615 B2 | 1/2004 | Denison et al. |
| 6,686,997 B1 | 2/2004 | Allen |
| 6,699,719 B2 | 3/2004 | Yamazaki et al. |
| 6,723,513 B2 | 4/2004 | Lexow |
| 6,746,594 B2 | 6/2004 | Akeson et al. |
| 6,762,048 B2 | 7/2004 | Williams |
| 6,794,177 B2 | 9/2004 | Markau et al. |
| 6,800,933 B1 | 10/2004 | Mathews et al. |
| 6,824,659 B2 | 11/2004 | Bayley et al. |
| 6,880,346 B1 | 4/2005 | Tseng et al. |
| 6,891,278 B2 | 5/2005 | Muller et al. |
| 6,916,665 B2 | 7/2005 | Bayley et al. |
| 6,952,651 B2 | 10/2005 | Su |
| 7,033,762 B2 | 4/2006 | Nelson et al. |
| 7,041,812 B2 | 5/2006 | Kumar et al. |
| 7,052,839 B2 | 5/2006 | Nelson et al. |
| 7,057,026 B2 | 6/2006 | Barnes et al. |
| 7,074,597 B2 | 7/2006 | Ju |
| 7,153,672 B1 | 12/2006 | Eickbush et al. |
| 7,189,503 B2 | 3/2007 | Akeson et al. |
| 7,223,541 B2 | 5/2007 | Fuller et al. |
| 7,229,799 B2 | 6/2007 | Williams |
| 7,233,541 B2 | 6/2007 | Yamamoto et al. |
| 7,238,485 B2 | 7/2007 | Akeson et al. |
| 7,244,602 B2 | 7/2007 | Frey et al. |
| 7,279,337 B2 | 10/2007 | Zhu |
| 7,321,329 B2 | 1/2008 | Tooyama et al. |
| 7,345,159 B2 | 3/2008 | Ju |
| 7,361,466 B2 | 4/2008 | Korlach et al. |
| 7,368,668 B2 | 5/2008 | Ren et al. |
| 7,405,281 B2 | 7/2008 | Xu et al. |
| 7,446,017 B2 | 11/2008 | Liu et al. |
| 7,452,698 B2 | 11/2008 | Sood et al. |
| 7,622,279 B2 | 11/2009 | Ju |
| 7,622,934 B2 | 11/2009 | Hibbs et al. |
| 7,625,701 B2 | 12/2009 | Williams et al. |
| 7,626,379 B2 | 12/2009 | Peters et al. |
| 7,635,578 B2 | 12/2009 | Ju et al. |
| 7,710,479 B2 | 5/2010 | Nitta et al. |
| 7,713,698 B2 | 5/2010 | Ju et al. |
| 7,727,722 B2 | 6/2010 | Nelson et al. |
| 7,745,116 B2 | 6/2010 | Williams |
| 7,777,013 B2 | 8/2010 | Xu et al. |
| 7,777,505 B2 | 8/2010 | White et al. |
| 7,790,869 B2 | 9/2010 | Ju et al. |
| 7,871,777 B2 | 1/2011 | Schneider et al. |
| 7,883,869 B2 | 2/2011 | Ju et al. |
| 7,897,738 B2 | 3/2011 | Brandis et al. |
| 7,906,371 B2 | 3/2011 | Kim et al. |
| 7,924,335 B2 | 4/2011 | Itakura et al. |
| 7,939,259 B2 | 5/2011 | Kokoris et al. |
| 7,939,270 B2 | 5/2011 | Holden et al. |
| 7,947,454 B2 | 5/2011 | Akeson et al. |
| 7,948,015 B2 | 5/2011 | Rothberg et al. |
| 7,973,146 B2 | 7/2011 | Shen et al. |
| 7,982,029 B2 | 7/2011 | Ju et al. |
| 7,989,928 B2 | 8/2011 | Liao et al. |
| 8,022,511 B2 | 9/2011 | Chiu et al. |
| 8,058,030 B2 | 11/2011 | Smith et al. |
| 8,058,031 B2 | 11/2011 | Xu et al. |
| 8,058,414 B2 | 11/2011 | Menchen et al. |
| 8,088,575 B2 | 1/2012 | Ju et al. |
| 8,133,672 B2 | 3/2012 | Bjornson et al. |
| 8,137,569 B2 | 3/2012 | Harnack et al. |
| 8,148,516 B2 | 4/2012 | Williams et al. |
| 8,192,961 B2 | 6/2012 | Williams |
| 8,252,911 B2 | 8/2012 | Bjornson et al. |
| 8,257,954 B2 | 9/2012 | Clark et al. |
| 8,298,792 B2 | 10/2012 | Ju et al. |
| 8,324,914 B2 | 12/2012 | Chen et al. |
| 8,461,854 B2 | 6/2013 | Chen et al. |
| 8,541,849 B2 | 9/2013 | Chen et al. |
| 2003/0027140 A1 | 2/2003 | Ju et al. |
| 2003/0054360 A1 | 3/2003 | Gold et al. |
| 2003/0101006 A1 | 5/2003 | Mansky et al. |
| 2003/0166282 A1 | 9/2003 | Brown et al. |
| 2003/0198982 A1 | 10/2003 | Seela et al. |
| 2004/0122335 A1 | 6/2004 | Sackellares et al. |
| 2004/0185466 A1 | 9/2004 | Ju et al. |
| 2005/0091989 A1 | 5/2005 | Leija et al. |
| 2005/0127035 A1 | 6/2005 | Ling |
| 2005/0186576 A1 | 8/2005 | Chan et al. |
| 2005/0032081 A1 | 9/2005 | Ju et al. |
| 2005/0208574 A1 | 9/2005 | Bayley et al. |
| 2005/0221351 A1 | 10/2005 | Ryu |
| 2005/0239194 A1 | 10/2005 | Gorenstein et al. |
| 2006/0057565 A1 | 3/2006 | Ju et al. |
| 2006/0105461 A1 | 5/2006 | Tom-Moy et al. |
| 2006/0115951 A1 | 6/2006 | Mosley |
| 2006/0252038 A1 | 11/2006 | Ju |
| 2006/0278992 A1 | 12/2006 | Trezza et al. |
| 2007/0173731 A1 | 7/2007 | Meka et al. |
| 2007/0190542 A1 | 8/2007 | Ling et al. |
| 2007/0196846 A1 | 8/2007 | Hanzel et al. |
| 2007/0275387 A1 | 11/2007 | Ju |
| 2008/0101988 A1 | 5/2008 | Kang et al. |
| 2008/0108082 A1 | 5/2008 | Rank et al. |
| 2008/0199932 A1 | 8/2008 | Hanzel et al. |
| 2008/0218184 A1 | 9/2008 | White et al. |
| 2008/0221806 A1 | 9/2008 | Bryant et al. |
| 2008/0286768 A1 | 11/2008 | Lexow |
| 2008/0318245 A1 | 12/2008 | Smirnov |
| 2009/0029477 A1 | 1/2009 | Meller et al. |
| 2009/0066315 A1 | 3/2009 | Hu et al. |
| 2009/0073293 A1 | 3/2009 | Yaffe et al. |
| 2009/0087834 A1 | 4/2009 | Lexow et al. |
| 2009/0099786 A1 | 4/2009 | Oliver et al. |
| 2009/0102534 A1 | 4/2009 | Schmid et al. |
| 2009/0136958 A1 | 5/2009 | Gershow et al. |
| 2009/0167288 A1 | 7/2009 | Reid et al. |
| 2009/0215050 A1 | 8/2009 | Jenson |
| 2009/0263791 A1 | 10/2009 | Ju et al. |
| 2009/0269759 A1 | 10/2009 | Menchen et al. |
| 2009/0298072 A1 | 12/2009 | Ju |
| 2009/0325154 A1 | 12/2009 | Ju et al. |
| 2010/0025238 A1 | 2/2010 | Gottlieb et al. |
| 2010/0025249 A1 | 2/2010 | Polonsky et al. |
| 2010/0035260 A1 | 2/2010 | Olasagati et al. |
| 2010/0047802 A1 | 2/2010 | Bjornson et al. |

(56) References Cited

U.S. PATENT DOCUMENTS

| | | |
|---|---|---|
| 2010/0072080 A1 | 3/2010 | Karhanek et al. |
| 2010/0075328 A1 | 3/2010 | Bjornson et al. |
| 2010/0075332 A1 | 3/2010 | Patel et al. |
| 2010/0078777 A1 | 4/2010 | Barth et al. |
| 2010/0092952 A1 | 4/2010 | Ju et al. |
| 2010/0093555 A1 | 4/2010 | Bjornson et al. |
| 2010/0121582 A1 | 5/2010 | Pan et al. |
| 2010/0122907 A1 | 5/2010 | Standford et al. |
| 2010/0148126 A1 | 6/2010 | Guan et al. |
| 2010/0243449 A1 | 9/2010 | Oliver |
| 2010/0261247 A1 | 10/2010 | Hanzel et al. |
| 2010/0292101 A1 | 11/2010 | So |
| 2010/0297644 A1 | 11/2010 | Kokoris et al. |
| 2010/0301398 A1 | 12/2010 | Rothberg et al. |
| 2010/0320094 A1 | 12/2010 | White et al. |
| 2010/0331194 A1 | 12/2010 | Turner et al. |
| 2011/0005918 A1 | 1/2011 | Akeson et al. |
| 2011/0014601 A2 | 1/2011 | Hardin et al. |
| 2011/0014611 A1 | 1/2011 | Ju et al. |
| 2011/0039259 A1 | 2/2011 | Ju et al. |
| 2011/0053284 A1 | 3/2011 | Meller et al. |
| 2011/0059505 A1 | 3/2011 | Hanzel et al. |
| 2011/0160093 A1 | 6/2011 | Van Den Boom et al. |
| 2011/0165652 A1 | 7/2011 | Hardin et al. |
| 2011/0168968 A1 | 7/2011 | Yang et al. |
| 2011/0174625 A1 | 7/2011 | Akeson et al. |
| 2011/0189659 A1 | 8/2011 | Clark et al. |
| 2011/0192723 A1 | 8/2011 | Chen et al. |
| 2011/0193249 A1 | 8/2011 | Chen et al. |
| 2011/0193570 A1 | 8/2011 | Chen et al. |
| 2011/0218414 A1 | 9/2011 | Kamath et al. |
| 2011/0244447 A1 | 10/2011 | Korlach |
| 2011/0287414 A1 | 11/2011 | Chen et al. |
| 2012/0034602 A1 | 2/2012 | Emig et al. |
| 2012/0040869 A1 | 2/2012 | Meller et al. |
| 2012/0052188 A1 | 3/2012 | Chen et al. |
| 2012/0094278 A1 | 4/2012 | Akeson et al. |
| 2012/0094332 A1 | 4/2012 | Lee et al. |
| 2012/0115736 A1 | 5/2012 | Bjornson et al. |
| 2012/0142006 A1 | 6/2012 | Ju et al. |
| 2012/0149021 A1 | 6/2012 | Yung et al. |
| 2012/0156680 A1 | 6/2012 | Ju et al. |
| 2012/0160681 A1 | 6/2012 | Davis et al. |
| 2012/0160687 A1 | 6/2012 | Akeson et al. |
| 2012/0160688 A1 | 6/2012 | Davis et al. |
| 2012/0187963 A1 | 7/2012 | Chen |
| 2012/0188092 A1 | 7/2012 | Chen |
| 2012/0196759 A1 | 8/2012 | Chen |
| 2012/0261261 A1 | 10/2012 | Huber |
| 2013/0015068 A1 | 1/2013 | Chen et al. |
| 2013/0207205 A1 | 8/2013 | Chen |
| 2013/0237460 A1 | 9/2013 | Deierling et al. |
| 2013/0240359 A1 | 9/2013 | Turner et al. |
| 2013/0244340 A1 | 9/2013 | Davis et al. |
| 2013/0263946 A1 | 10/2013 | Afzali-Ardakani et al. |
| 2013/0264207 A1 | 10/2013 | Ju et al. |
| 2013/0280700 A1 | 10/2013 | Ju et al. |
| 2014/0014513 A1 | 1/2014 | Chen et al. |
| 2014/0093869 A1 | 4/2014 | Ju et al. |
| 2014/0134616 A1 | 5/2014 | Davis et al. |

FOREIGN PATENT DOCUMENTS

| | | |
|---|---|---|
| WO | WO 97/32999 A1 | 9/1997 |
| WO | WO 97/46704 A1 | 12/1997 |
| WO | WO 01/48235 A2 | 7/2001 |
| WO | WO 02/22883 A1 | 3/2002 |
| WO | WO 02/29003 A2 | 4/2002 |
| WO | WO 02/029003 A3 | 7/2002 |
| WO | WO 02/079519 A1 | 10/2002 |
| WO | WO 03/020734 A2 | 3/2003 |
| WO | WO 2004/007773 A1 | 1/2004 |
| WO | WO 2004/055160 A2 | 7/2004 |
| WO | WO 2004/055160 A3 | 8/2004 |
| WO | WO 2004/071155 A2 | 8/2004 |
| WO | WO 2004/072238 A2 | 8/2004 |
| WO | WO 2005/084367 A2 | 9/2005 |
| WO | WO 2005/084367 A3 | 12/2005 |
| WO | WO 2006/020775 A2 | 2/2006 |
| WO | WO 2007/002204 A2 | 1/2007 |
| WO | WO 2007/053702 A2 | 5/2007 |
| WO | WO 2007/053719 A2 | 5/2007 |
| WO | WO 2007/062105 A2 | 5/2007 |
| WO | WO 2007/127327 A2 | 11/2007 |
| WO | WO 2007/146158 A1 | 12/2007 |
| WO | WO 2007/053702 A3 | 1/2008 |
| WO | WO 2008/034602 A2 | 3/2008 |
| WO | WO 2008/069973 A2 | 6/2008 |
| WO | WO 2008/102120 A1 | 8/2008 |
| WO | WO 2008/124107 A1 | 10/2008 |
| WO | WO 2008/034602 A3 | 2/2009 |
| WO | WO 2009/020682 A2 | 2/2009 |
| WO | WO 2007/002204 A3 | 4/2009 |
| WO | WO 2007/053719 A3 | 4/2009 |
| WO | WO 2007/062105 A3 | 4/2009 |
| WO | WO 2009/051807 A1 | 4/2009 |
| WO | WO 2009/054922 A1 | 4/2009 |
| WO | WO 2008/069973 A3 | 6/2009 |
| WO | WO 2010/109197 A2 | 9/2010 |
| WO | WO 2011/038241 A1 | 3/2011 |
| WO | WO 2011/067559 A1 | 6/2011 |
| WO | WO 2011/097028 A1 | 8/2011 |
| WO | WO 2011/106459 A2 | 9/2011 |
| WO | WO 2012/009578 A2 | 1/2012 |
| WO | WO 2012/088339 A2 | 6/2012 |
| WO | WO 2012/088341 A2 | 6/2012 |
| WO | WO 2012/121756 A1 | 9/2012 |
| WO | WO 2013/109970 A1 | 7/2013 |
| WO | WO 2013/154999 A2 | 10/2013 |
| WO | WO 2013/191793 A1 | 12/2013 |

OTHER PUBLICATIONS

Davies, Kevin, Genia's Nanopore/Microchip Technology Gains Life Technologies' Support. Bio-IT World, Oct. 21, 2011.
Office action dated Feb. 25, 2013 for U.S. Appl. No. 13/396,522.
International search report dated Feb. 7, 2014 for PCT Application No. US2013/068967.
International search report dated Sep. 24, 2013 for PCT Application No. US2013/035630.
Office action dated Mar. 28, 2014 for U.S. Appl. No. 13/333,932.
Office action dated Apr. 10, 2014 for U.S. Appl. No. 12/658,602.
Office action dated Apr. 10, 2014 for U.S. Appl. No. 13/759,701.
Office action dated Apr. 11, 2014 for U.S. Appl. No. 12/658,601.
Office action dated Apr. 15, 2014 for U.S. Appl. No. 12/658,591.
Schneider et al. DNA sequencing with nanopores. Nat Biotechnol. Apr. 10, 2012; 30(4):326-8. doi: 10.1038/nbt.2181.
U.S. Appl. No. 14/073,445, filed Nov. 6, 2013, Davis et al.
Chinese office action dated Jul. 2, 2012 for CN Application No. 200780028545.1.
Chinese office action dated Oct. 12, 2013 for CN Application No. 200780028545.1.
International search report and written opinion dated Sep. 13, 2013 for PCT Application No. US2013/046012.
International search report dated Feb. 26, 2013 for PCT Application No. US2012/069911.
McGuigan, et al. DNA fingerprinting by sampled sequencing. Methods in Enzymology. 1993; 218:241-258.
Office action dated Jan. 17, 2014 for U.S. Appl. No. 13/276,200.
Rosenstein, et al. Integrated nanopore sensing platform with sub-microsecond temporal resolution. Nat Methods. Mar. 18, 2012;9(5):487-92. doi: 10.1038/nmeth.1932.
Venkatesan, et al. Nanopore sensors for nucleic acid analysis. Nat Nanotechnol. Sep. 18, 2011;6(10):615-24. doi: 10.1038/nnano.2011.129.
U.S. Appl. No. 13/745,688, filed Jan. 18, 2013, Davis et al.
Akeson, et al. Microsecond time-scale discrimination among polycytidylic acid, polyadenylic acid, and polyuridylic acid as homopolymers or as segments within single RNA molecules. Biophys J. Dec. 1999;77(6):3227-33.

(56) References Cited

OTHER PUBLICATIONS

Aksimentiev, et al. Microscopic Kinetics of DNA Translocation through synthetic nanopores. Biophys J. Sep. 2004;87(3):2086-97.

Andersen. Sequencing and the single channel. Biophys J. Dec. 1999;77(6):2899-901.

Ashkenasy, et al. Recognizing a single base in an individual DNA strand: a step toward DNA sequencing in nanopores. Angew Chem Int Ed Engl. Feb. 18, 2005;44(9):1401-4.

Atanasov, et al. Membrane on a chip: a functional tethered lipid bilayer membrane on silicon oxide surfaces. Biophys J. Sep. 2005;89(3):1780-8.

Baaken, et al. Planar microelectrode-cavity array for high-resolution and parallel electrical recording of membrane ionic currents. Lab Chip. Jun. 2008;8(6):938-44. Epub Apr. 16, 2008.

Bai, et al. Design and synthesis of a photocleavable biotinylated nucleotide for DNA analysis by mass spectrometry. Nucleic Acids Res. Jan. 26, 2004;32(2):535-41. Print 2004.

Benner, et al. Sequence-specific detection of individual DNA polymerase complexes in real time using a nanopore. Nat Nanotechnol. Nov. 2007;2(11):718-24. Epub Oct. 28, 2007.

Bezrukov, et al. Counting polymers moving through a single ion channel. Nature. Jul. 28, 1994;370(6487):279-81.

Bezrukov, et al. Dynamic partitioning of neutral polymers into a single ion channel. In NATO Advanced Research Workshop: Structure and dynamics of confined polymers. Kulwer Press. 2002; 117-130.

Bezrukov, et al. Dynamics and free energy of polymers partitioning into a nanoscale pore. Macromolecules. 1996; 29:8517-8522.

Bezrukov, et al. Neutral polymers in the nanopores of alamethicin and alpha-hemolysin. Biologicheskie Membrany 2001, 18, 451-455.

Boireau, et al. Unique supramolecular assembly of a redox protein with nucleic acids onto hybrid bilayer: towards a dynamic DNA chip. Biosens Bioelectron. Feb. 15, 2005;20(8):1631-7.

Bokhari, et al. A parallel graph decomposition algorithm for DNA sequencing with nanopores. Bioinformatics. Apr. 1, 2005;21(7):889-96. Epub Nov. 11, 2004.

Buchmann, et al. Electrochemical release from gold-thiolate electrodes for controlled insertion of ion channels into bilayer membranes. Bioorg Med Chem. Mar. 15, 2004;12(6):1315-24.

Butler, et al. Ionic current blockades from DNA and RNA molecules in the alpha-hemolysin nanopore. Biophys J. Nov. 1, 2007;93(9):3229-40. Epub Aug. 3, 2007.

Butler, et al. of RNA orientation during translocation through a biological nanopore. Biophys J. Jan. 1, 2006;90(1):190-9. Epub Oct. 7, 2005.

Butler, et al. Single-molecule DNA detection with an engineered MspA protein nanopore. Proc Natl Acad Sci U S A. Dec. 30, 2008;105(52):20647-52. Epub Dec. 19, 2008.

Chandler, et al. Membrane surface dynamics of DNA-threaded nanopores revealed by simultaneous single-molecule optical and ensemble electrical recording. Langmuir. Feb. 3, 2004;20(3):898-905.

Churbanov, et al. Duration learning for analysis of nanopore ionic current blockades. BMC Bioinformatics. Nov. 1, 2007;8 Suppl 7:S14.

Clarke, et al. Continuous base identification for single-molecule nanopore DNA sequencing. Nat Nanotechnol. Apr. 2009;4(4):265-70. Epub Feb. 22, 2009.

Cockroft, et al. A single-molecule nanopore device detects DNA polymerase activity with single-nucleotide resolution. J Am Chem Soc. Jan. 23, 2008;130(3):818-20. Epub Jan. 1, 2008.

Danelon, et al. Cell membranes suspended across nanoaperture arrays.Langmuir. Jan. 3, 2006;22(1):22-5.

Deamer, et al. Characterization of nucleic acids by nanopore analysis. Acc Chem Res. Oct. 2002;35(10):817-25.

Derrington, et al. Nanopore DNA sequencing with MspA. Proc Natl Acad Sci U S A. Sep. 14, 2010;107(37):16060-5. Epub Aug. 26, 2010.

Einstein. Investigations on the theory of Brownian movement. Dover, New York. 1956.

Ervin, et al. Simultaneous alternating and direct current readout of protein ion channel blocking events using glass nanopore membranes. Anal Chem. Mar. 15, 2008;80(6):2069-76. Epub Feb. 23, 2008.

Flusberg, et al. Direct detection of DNA methylation during single-molecule, real-time sequencing. Nat Methods. Jun. 2010;7(6):461-5. Epub May 9, 2010.

Fologea, et al. Detecting single stranded DNA with a solid state nanopore. Nano Lett. Oct. 2005;5(10):1905-9.

Fologea, et al. Slowing DNA translocation in a solid-state nanopore. Nano Lett. Sep. 2005;5(9):1734-7.

Gu, et al. Stochastic sensing of organic analytes by a pore-forming protein containing a molecular adapter. Nature. Apr. 22, 1999;398(6729):686-90.

Haas, et al. Improvement of the quality of self assembled bilayer lipid membranes by using a negative potential. Bioelectrochemistry. Aug. 2001;54(1):1-10.

Halverson, et al. Asymmetric blockade of anthrax protective antigen ion channel asymmetric blockade. J Biol Chem. Oct. 7, 2005;280(40):34056-62. Epub Aug. 8, 2005.

Harlepp, et al. Probing complex RNA structures by mechanical force. Eur Phys J E Soft Matter. Dec. 2003;12(4):605-15.

Heins, et al. Detecting single porphyrin molecules in a conically shaped synthetic nanopore. Nano Left. Sep. 2005;5(9):1824-9.

Heng, et al. Stretching DNA using the electric field in a synthetic nanopore. Nano Lett. Oct. 2005;5(10):1883-8.

Heng, et al. The electromechanics of DNA in a synthetic nanopore. Biophys J. Feb. 1, 2006;90(3):1098-106. Epub Nov. 11, 2005.

Henrickson, et al. Driven DNA transport into an asymmetric nanometer-scale pore. Phys Rev Lett. Oct. 2, 2000;85(14):3057-60.

Henrickson, et al. Probing single nanometer-scale pores with polymeric molecular rulers. J Chem Phys. Apr. 7, 2010;132(13):135101. doi: 10.1063/1.3328875.

Holden, et al. Direct introduction of single protein channels and pores into lipid bilayers. J Am Chem Soc. May 11, 2005;127(18):6502-3.

Holden, et al. Direct transfer of membrane proteins from bacteria to planar bilayers for rapid screening by single-channel recording. Nat Chem Biol. Jun. 2006;2(6):314-8. Epub May 7, 2006.

Hromada, et al. Single molecule measurements within individual membrane-bound ion channels using a polymer-based bilayer lipid membrane chip. Lab Chip. Apr. 2008;8(4):602-8. Epub Feb. 29, 2008.

International Preliminary Report on Patentability issued Dec. 24, 2008 in connection with International Application No. PCT/US2007/013559.

International search report and written opinion dated Mar. 18, 2013 for PCT/US2012/063099.

International search report and written opinion dated May 3, 2012 for PCT/US2012/020827.

International search report and written opinion dated May 9, 2013 for PCT/US2013/028058.

International search report and written opinion dated May 16, 2013 for PCT Application No. US2013/026514.

International search report and written opinion dated May 16, 2013 for PCT Application No. US2013/022273.

International search report and written opinion dated Jul. 8, 2011 for PCT/US2011/064490.

International search report and written opinion dated Aug. 28, 2012 for PCT/US2011/066627.

International search report and written opinion dated Aug. 28, 2012 for PCT/US2011/066632.

International search report and written opinion dated Oct. 29, 2007 for PCT/US2007/013559.

International search report and written opinion dated Nov. 5, 2012 for PCT/US2011/064490.

International search report dated Feb. 24, 2013 for PCT/US2011/065640.

Ito, et al. Simultaneous determination of the size and surface charge of individual nanoparticles using a carbon nanotube-based Coulter counter. Anal Chem. May 15, 2003;75(10):2399-406.

(56) References Cited

OTHER PUBLICATIONS

Ju, et al. Cassette labeling for facile construction of energy transfer fluorescent primers. Nucleic Acids Res. Mar. 15, 1996;24(6):1144-8.
Ju, et al. Energy transfer primers: a new fluorescence labeling paradigm for DNA sequencing and analysis. Nat Med. Feb. 1996;2(2):246-9.
Ju, et al. Fluorescence energy transfer dye-labeled primers for DNA sequencing and analysis. Proc Natl Acad Sci U S A. May 9, 1995;92(10):4347-51.
Ju, et al. Four-color DNA sequencing by synthesis using cleavable fluorescent nucleotide reversible terminators. Proc Natl Acad Sci U S A. Dec. 26, 2006;103(52):19635-40. Epub Dec. 14, 2006.
Jurak, et al. Wettability and topography of phospholipid DPPC multilayers deposited by spin-coating on glass, silicon, and mica slides. Langmuir. Sep. 25, 2007;23(20):10156-63. Epub Aug. 28, 2007.
Kang, et al. A storable encapsulated bilayer chip containing a single protein nanopore. J Am Chem Soc. Apr. 18, 2007;129(15):4701-5. Epub Mar. 22, 2007.
Kasianowicz, et al. Characterization of individual polynucleotide molecules using a membrane channel. Proc Natl Acad Sci U S A. Nov. 26, 1996;93(24):13770-3.
Kasianowicz, et al. Physics of DNA threading through a nanometer pore and applications to simultaneous multianalyte sesnsing. In NATO Advanced Research Workshop: Structure and dynamics of confined polymers. Kluwer Press. 2002; 141-163.
Kasianowicz, et al. Simultaneous multianalysis detection with a nanopore. Anal. Chem. 2001; 73:2268-2272.
Kasianowicz. Nanometer-scale pores: potential applications for analyte detection and DNA characterization. Dis Markers. 2002;18(4):185-91.
Kasianowicz. Nanopores: flossing with DNA. Nat Mater. Jun. 2004;3(6):355-6.
Kawano, et al. Controlling the translocation of single-stranded DNA through alpha-hemolysin ion channels using viscosity. Langmuir. Jan. 20, 2009;25(2):1233-7.
Krasilnikov, et al. A simple method for the determination of the pore radius of ion channels in planar lipid bilayer membranes. FEMS Microbiol Immunol. Sep. 1992;5(1-3):93-100.
Krasilnikov, et al. Single polymer molecules in a protein nanopore in the limit of a strong polymer-pore attraction. Phys Rev Lett. Jul. 7, 2006;97(1):018301. Epub Jul. 5, 2006.
Krasilnikov, et al. Sizing channels with neutral polymers. In NATO Advanced Research Workshop: Structure and dynamics of confined polymers. Kluwer Press. 2002; 97-116.
Kullman, et al. Transport of maltodextrins through maltoporin: a single-channel study. Biophys J. Feb. 2002;82(2):803-12.
Kumar, et al. PEG-labeled nucleotides and nanopore detection for single molecule DNA sequencing by synthesis. Sci Rep. 2012;2:684. Epub Sep. 21, 2012.
Kutik, et al. Dissecting membrane insertion of mitochondrial beta-barrel proteins. Cell. Mar. 21, 2008;132(6):1011-24.
Lee, et al. Enhancing the catalytic repertoire of nucleic acids: a systematic study of linker length and rigidity. Nucleic Acids Res. Apr. 1, 2001;29(7):1565-73.
Li, et al. A photocleavable fluorescent nucleotide for DNA sequencing and analysis. Proc Natl Acad Sci U S A. Jan. 21, 2003;100(2):414-9. Epub Jan. 6, 2003.
Li, et al. Ion-beam sculpting at nanometre length scales. Nature. Jul. 12, 2001;412(6843):166-9.
Linear Technology, High Efficiency Thermoelectric Cooler Controller, 2001.
Low Noise, Dual Switched Integrator, Burr-Brown Corporation, Sep. 1994.
Lundquist, et al. A new tri-orthogonal strategy for peptide cyclization. Org Lett. Sep. 19, 2002;4(19):3219-21.
Madampage, et al. Nanopore detection of antibody prion interactions. Anal Biochem. Jan. 1, 2010;396(1):36-41. Epub Aug. 21, 2009.
Mathe, et al. Nanopore unzipping of individual DNA hairpin molecules. Biophys J. Nov. 2004;87(5):3205-12. Epub Sep. 3, 2004.
Mathe, et al. Orientation discrimination of single-stranded DNA inside the alpha-hemolysin membrane channel. Proc Natl Acad Sci U S A. Aug. 30, 2005;102(35):12377-82. Epub Aug. 19, 2005.
Maurer, et al. Reconstitution of ion channels in agarose-supported silicon orifices. Biosens Bioelectron. May 15, 2007;22(11):2577-84. Epub Nov. 13, 2006.
McNally, et al. Optical recognition of converted DNA nucleotides for single-molecule DNA sequencing using nanopore arrays. Nano Lett. Jun. 9, 2010;10(6):2237-44.
Meller, et al. Rapid nanopore discrimination between single polynucleotide molecules. Proc Natl Acad Sci U S A. Feb. 1, 2000;97(3):1079-84.
Meller, et al. Single molecule measurements of DNA transport through a nanopore. Electrophoresis. Aug. 2002;23(16):2583-91.
Mohammad, et al. Controlling a single protein in a nanopore through electrostatic traps. J Am Chem Soc. Mar. 26, 2008;130(12):4081-8. Epub Mar. 6, 2008.
Movileanu, et al. Partitioning of a polymer into a nanoscopic protein pore obeys a simple scaling law. Proc Natl Acad Sci U S A. Aug. 28, 2001;98(18):10137-41. Epub Aug. 14, 2001.
Movileanu, et al. Partitioning of individual flexible polymers into a nanoscopic protein pore. Biophys J. Aug. 2003;85(2):897-910.
Nakane, et al. A Nanosensor for Transmembrane Capture and Identification of Single Nucleic Acid Molecules, Biophysical Journal, vol. 87, Issue 1, Jul. 2004, pp. 615-621, ISSN 0006-3495.
Office action dated Apr. 11, 2013 for U.S. Appl. No. 12/658,603.
Office action dated Apr. 26, 2012 for U.S. Appl. No. 12/658,591.
Office action dated Apr. 26, 2012 for U.S. Appl. No. 12/658,601.
Office action dated Jun. 15, 2012 for U.S. Appl. No. 12/658,604.
Office action dated Jun. 28, 2012 for U.S. Appl. No. 12/308,091.
Office action dated Aug. 3, 2012 for U.S. Appl. No. 12/658,602.
Office action dated Oct. 2, 2012 for U.S. Appl. No. 12/658,603.
Office action dated Oct. 16, 2012 for U.S. Appl. No. 12/658,601.
Office action dated Oct. 25, 2012 for U.S. Appl. No. 12/658,591.
Office action dated Nov. 26, 2011 for U.S. Appl. No. 12/308,091.
Office action dated Dec. 17, 2012 for U.S. Appl. No. 13/620,973.
Oxford Nanopore Technologies, Sensor Array Chip, Jul. 14, 2011.
Park, et al. DNA hybridization sensors based on electrochemical impedance spectroscopy as a detection tool. Sensors (Basel). 2009;9(12):9513-32. Epub Nov. 26, 2009.
Perkins, et al. Relaxation of a single DNA molecule observed by optical microscopy. Science. May 6, 1994;264(5160):822-6.
Pourmand, et al. Multiplex Pyrosequencing. Acids Res. Apr. 1, 2002;30(7):e31.
Purnell, et al. Discrimination of single base substitutions in a DNA strand immobilized in a biological nanopore. ACS Nano. Sep. 22, 2009;3(9):2533-8.
Reiner, et al. Temperature sculpting in yoctoliter volumes. J Am Chem Soc. Feb. 27, 2013;135(8):3087-94. doi: 10.1021/ja309892e. Epub Feb. 14, 2013.
Reiner, et al. Theory for polymer analysis using nanopore-based single-molecule mass spectrometry. Proc Natl Acad Sci U S A. Jul. 6, 2010;107(27):12080-5. doi: 10.1073/pnas.1002194107. Epub Jun. 21, 2010.
Rief, et al. Sequence-dependent mechanics of single DNA molecules. Nat Struct Biol. Apr. 1999;6(4):346-9.
Robertson, et al. Single-molecule mass spectrometry in solution using a solitary nanopore. Proc Natl Acad Sci U S A. May 15, 2007;104(20):8207-11. Epub May 9, 2007.
Rosenblum, et al. New dye-labeled terminators for improved DNA sequencing patterns. Nucleic Acids Res. Nov. 15, 1997;25(22):4500-4.
Rostovtsev, et al. A stepwise huisgen cycloaddition process: copper(I)-catalyzed regioselective "ligation" of azides and terminal alkynes. Angew Chem Int Ed Engl. Jul. 15, 2002;41(14):2596-9.
Rotem et al., Temperature Measurement in the Intel Core Duo Processor, 2007.
Saleh, et al. Direct detection of antibody-antigen binding using an on-chip artificial pore. Proc Natl Acad Sci U S A. Feb. 4, 2003;100(3):820-4. Epub Jan. 27, 2003.

(56) References Cited

OTHER PUBLICATIONS

Sanchez-Magraner, et al. Membrane insertion of *Escherichia coli* alpha-hemolysin is independent from membrane lysis. J Biol Chem. Mar. 3, 2006;281(9):5461-7. Epub Dec. 22, 2005.
Sauer-Budge, et al. Unzipping kinetics of double-stranded DNA in a nanopore. Phys Rev Lett. Jun. 13, 2003;90(23):238101. Epub Jun. 9, 2003.
Seo, et al. Photocleavable fluorescent nucleotides for DNA sequencing on a chip constructed by site-specific coupling chemistry. Proc Natl Acad Sci U S A. Apr. 13, 2004;101(15):5488-93. Epub Apr. 2, 2004.
Shim, et al. Encapsulating a single G-quadruplex aptamer in a protein nanocavity. J Phys Chem B. Jul. 17, 2008;112(28):8354-60. Epub Jun. 19, 2008.
Simon, et al. Formation and stability of a suspended biomimetic lipid bilayer on silicon submicrometer-sized pores. J Colloid Interface Sci. Apr. 15, 2007;308(2):337-43. Epub Jan. 31, 2007.
Singer et al., Nanopore Based Sequence Specific Detection of Duplex DNA for Genomic Profiling, Jan. 8, 2010, published Jan. 20, 2010, pp. 738-742.
Singh, et al. Synthesis of natural flutimide and analogous fully substituted pyrazine-2,6-diones, endonuclease inhibitors of influenza virus. J Org Chem. Aug. 10, 2001;66(16):5504-16.
Smith, et al. Overstretching B-DNA: the elastic response of individual double-stranded and single-stranded DNA molecules. Science. Feb. 9, 1996;271(5250):795-9.
Stanford, et al. Transport of DNA through a single nanometer-scale pore: evolution of signal structure. IEEE Workshop on Genomic Signal Processing and Statistics. Baltimore, MD. May 26, 2004.
Stanford, et al. Using HMMs to Quantify Signals from DNA Driven Through a Nanometer-Scale Pore. IEEE Workshop on Genomic Signal Processing and Statistics. Raleigh, NC. Oct. 2002; 11-13.
Stefureac, et al. Nanopore analysis of the interaction of metal ions with prion proteins and peptides. Biochem Cell Biol. Apr. 2010;88(2):347-58.
Stefureac, et al. Transport of alpha-helical peptides through alpha-hemolysin and aerolysin pores. Biochemistry. Aug. 1, 2006;45(30):9172-9.
Stoddart, et al. Nucleobase recognition in ssDNA at the central constriction of the alpha-hemolysin pore. Nano Lett. Sep. 8, 2010;10(9):3633-7.
Stoddart, et al. Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009.
Storm, et al. Translocation of double-strand DNA through a silicon oxide nanopore. Phys Rev E Stat Nonlin Soft Matter Phys. May 2005;71(5 Pt 1):051903. Epub May 6, 2005.
Streater, et al. Novel 3-hydroxy-2(1H)-pyridinones. Synthesis, iron(III)-chelating properties, and biological activity. J Med Chem. Jun. 1990;33(6):1749-55.
Studer, et al. Formation of individual protein channels in lipid bilayers suspended in nanopores. Colloids Surf B Biointerfaces. Oct. 15, 2009;73(2):325-31. Epub Jun. 10, 2009.
Suzuki, et al. Highly reproducible method of planar lipid bilayer reconstitution in polymethyl methacrylate microfluidic chip. Langmuir. Feb. 14, 2006;22(4):1937-42.
Thomson et al. Preliminary nanopore cheminformatics analysis of aptamer-target binding strength. BMC Bioinformatics. Nov. 1, 2007;8 Suppl 7:S11.
UK search and examination report dated Feb. 25, 2013 for GB Application No. 1216656.7.
UK search and examination report dated May 1, 2013 for GB Application No. 1216026.3.
Vercoutere, et al. Discrimination among individual Watson-Crick base pairs at the termini of single DNA hairpin molecules. Nucleic Acids Res. Feb. 15, 2003;31(4):1311-8.
Vercoutere, et al. Rapid discrimination among individual DNA hairpin molecules at single-nucleotide resolution using an ion channel. Nat Biotechnol. Mar. 2001;19(3):248-52.
Viasnoff, et al. Probing DNA base pairing energy profiles using a nanopore. Eur Biophys J. Feb. 2009;38(2):263-9. Epub Oct. 3, 2008.
Wang, et al. DNA heterogeneity and phosphorylation unveiled by single-molecule electrophoresis. Proc Natl Acad Sci U S A. Sep. 14, 2004;101(37):13472-7. Epub Sep. 1, 2004.
Wanunu, et al. DNA profiling using solid-state nanopores: detection of DNA-binding molecules. Nano Lett. Oct. 2009;9(10):3498-502.
Weng, et al. Fluid biomembranes supported on nanoporous aerogel/xerogel substrates. Langmuir. Aug. 17, 2004;20(17):7232-9.
Wilson, et al. Electronic control of DNA polymerase binding and unbinding to single DNA molecules. ACS Nano. Apr. 28, 2009;3(4):995-1003.
Wilson, et al. Feedback control of a DNA molecule tethered in a nanopore to repeatedly probe DNA-binding enzymes. Conf Proc IEEE Eng Med Biol Soc. 2008;2008:5745-8.
Winters-Hilt, et al. Nanopore-based kinetics analysis of individual antibody-channel and antibody-antigen interactions. BMC Bioinformatics. Nov. 1, 2007;8 Suppl 7:S20.
Woodside, et al. Direct measurement of the full, sequence-dependent folding landscape of a nucleic acid. Science. Nov. 10, 2006;314(5801):1001-4.
Woodside, et al. Nanomechanical measurements of the sequence-dependent folding landscapes of single nucleic acid hairpins. Proc Natl Acad Sci U S A. Apr. 18, 2006;103(16):6190-5. Epub Apr. 10, 2006.
Wu, et al. Single-molecule detection of nitrogen mustards by covalent reaction within a protein nanopore. J Am Chem Soc. May 28, 2008;130(21):6813-9. Epub Apr. 30, 2008.
Zeineldin, et al. Using bicellar mixtures to form supported and suspended lipid bilayers on silicon chips. Langmuir. Sep. 12, 2006;22(19):8163-8.
Zwolak, et al. Electronic signature of DNA nucleotides via transverse transport. Nano Lett. Mar. 2005;5(3):421-4.
Allowed claims dated Apr. 30, 2008 in U.S. Appl. No. 12/084,457.
Chinese office action dated Apr. 9, 2013 for CN Application No. 200780028545.1. (with English translation).
Eid, et al. Real-time DNA sequencing from single polymerase molecules. Science. Jan. 2, 2009;323(5910):133-8. doi: 10.1126/science.1162986. Epub Nov. 20, 2008.
European search report and opinion dated Apr. 16, 2014 for EP Application No. 11848220.7.
Guranowski, et al. Selective degradation of 2'-adenylated diadenosine tri- and tetraphosphates, Ap(3)A and Ap(4)A, by two specific human dinucleoside polyphosphate hydrolases. Arch Biochem Biophys. Jan. 1, 2000;373(1):218-24.
International search report and written opinion dated Oct. 25, 2013 for PCT Application No. US2013/035635.
Invitation to Pay Additional Fees dated Aug. 19, 2013 for PCT Application No. US2013/035635.
Kumar, et al. Terminal phosphate labeled nucleotides: synthesis, applications, and linker effect on incorporation by DNA polymerases. Nucleosides Nucleotides Nucleic Acids. 2005;24(5-7):401-8.
Mulder, et al. Nucleotide modification at the gamma-phosphate leads to the improved fidelity of HIV-1 reverse transcriptase. Nucleic Acids Res. Sep. 1, 2005;33(15):4865-73. Print 2005.
Office Action dated Mar. 27, 2014 in connection with Chinese Patent Application No. 201180063978.7 (with English translation of cover page only).
Pending claims dated Jul. 19, 2011 in U.S. Appl. No. 13/186,353.
Pending claims dated Dec. 14, 2007 in U.S. Appl. No. 11/922,385.
Pending claims in U.S. Appl. No. 13/959,660, filed Aug. 5, 2013, Ju et al.
Reynolds, et al. Synthesis and stability of novel terminal phosphate-labeled nucleotides. Nucleosides Nucleotides Nucleic Acids. Jan. 2008;27(1):18-30. doi: 10.1080/15257770701571768.
Sood, et al. Terminal phosphate-labeled nucleotides with improved substrate properties for homogeneous nucleic acid assays. J Am Chem Soc. Mar. 2, 2005;127(8):2394-5.

| Titanium Nitride |
| Aluminum |
| Semiconductor |

*FIG. 28*

CHIP SET-UP AND HIGH-ACCURACY NUCLEIC ACID SEQUENCING

CROSS-REFERENCE

This application claims the benefit of U.S. Provisional Patent Application No. 61/771,031, filed Feb. 28, 2013, U.S. Provisional Patent Application No. 61/660,537, filed Jun. 15, 2012, and U.S. Provisional Patent Application No. 61/660,543, filed Jun. 15, 2012, each of which is incorporated herein by reference in its entirety.

BACKGROUND

Biochips can be used for various kinds of molecular detection and sensing, including the sequencing of nucleic acid molecules. Nucleic acid sequencing is the process for determining the nucleic acid basis of a nucleic acid. Such sequence information can be helpful in diagnosing and/or treating a subject. For example, the nucleic acid sequence of a subject may be used to identify, diagnose and potentially develop treatments for genetic diseases. As another example, research into pathogens may lead to treatment for contagious diseases.

There are methods available which may be used to sequence a nucleic acid. Such methods, however, are expensive and may not provide sequence information within a time period and at an accuracy that may be necessary to diagnose and/or treat a subject.

SUMMARY

The present disclosure provides devices, systems and methods for species detection and sequencing, such as molecular detection and/or nucleic acid sequencing. Methods are also provided for forming high accuracy nanopore devices. The present disclosure provides high performance devices that can be configured for high accuracy nucleic acid sequencing by sequencing nucleic acid molecules (e.g., as part of a larger nucleic acid sample) independently and in parallel, and at substantially high accuracy (e.g., at least about 97%, 98%, or 99%), in some cases in a substantially low time period (e.g., less than about 1 day, 12 hours, 6 hours, 5 hours, 4 hours, 3 hours, 2 hours, or 1 hour). Such high performance devices can include, for example, at least about 500, 600, 700, 800, 900, 1000, 10000 individual nanopore sensors per 1 mm$^2$. Independent and parallel sequencing can enable high accuracy sequencing, in some cases with the aid of redundant nucleic acid sequence information.

In an aspect, a method for nucleic acid sequencing comprises: (a) providing a chip comprising a plurality of discrete sites at a density greater than or equal to about 500 sites per 1 mm$^2$, wherein an individual site of said plurality of discrete sites comprises at least one nanopore formed in a membrane disposed adjacent to an electrode, wherein each discrete site is adapted to aid in the detection of said nucleic acid molecule or a portion thereof; (b) directing a plurality of nucleic acid molecules to said plurality of discrete sites; and (c) characterizing, with the aid of a computer processor coupled to said discrete sites, a nucleic acid sequence of each of said nucleic molecules based on electrical signals received from said plurality of discrete sites.

In another aspect, a system for sequencing a nucleic acid molecule comprises: (a) a chip comprising a plurality of discrete sites at a density greater than or equal to about 500 sites per 1 mm$^2$, wherein an individual site of said plurality of discrete sites comprises at least one nanopore formed in a membrane disposed adjacent to an electrode, wherein each discrete site is adapted to aid in the detection of said nucleic acid molecule or a portion thereof; and (b) a processor coupled to said chip, wherein said processor is programmed to aid in characterizing a nucleic acid sequence of said nucleic acid molecule based on electrical signals received from said plurality of discrete sites.

In another aspect, a system comprises a substrate with a surface comprising discrete sites at a density greater than or equal to about 500 sites per 1 mm$^2$, wherein an individual site of said plurality of discrete sites comprises at least one nanopore and a sensing circuit adjacent to said nanopore, wherein said sensing circuit is in communication with a computer processor that is programmed to aid in characterizing a nucleic acid sequence of a nucleic acid molecule based on electrical signals received from said sensing circuit.

In another aspect, a membrane is disposed upon a membrane-incompatible surface in sensing proximity to an electrode coupled to an integrated circuit, wherein said membrane, as measured by said integrated circuit, exhibits a capacitance greater than about 5 fF/μm$^2$ per square micron and a conductance less than about 0.25 nano Siemens per mole of electrolyte as measured by said electrode under an applied voltage of at least about 50 mV. The membrane can be part of a device (e.g., chip) for species detection and/or nucleic acid sequencing.

In another aspect, a device for use in molecular sensing comprises one or more nanopores in a membrane disposed upon at least one membrane incompatible surface in sensing proximity to an electrode coupled to an integrated circuit, wherein said membrane comprising said one or more nanopores exhibits a capacitance greater than about 5 fF/μm$^2$ and a conductance less than about 10 nano Siemens per mole of electrolyte per nanopore as measured by said electrode under an applied voltage of at least about 50 mV.

In another aspect, a method for sequencing a nucleic acid molecule comprises: (a) providing a chip comprising an array of sensors, wherein an individual sensor of said array of sensors comprises a membrane adjacent to a sensing electrode, wherein said membrane comprises at least one nanopore configured to aid in the detection of one or more nucleic acid bases of said nucleic acid molecule or portion thereof upon the flow of said nucleic acid molecule or portion thereof through or adjacent to said at least one nanopore; (b) directing said nucleic acid molecule to said individual sensor; (c) applying a series of electrical pulses to said membrane upon directing said nucleic acid molecule to said individual sensor; and (d) detecting one or more nucleic acid bases of said nucleic acid molecule or portion thereof between said series of electrical pulses.

In another aspect, a method for sequencing a nucleic acid molecule comprises: (a) providing a chip comprising an array of individual sensors, wherein an individual sensor of said array comprises an electrode that is disposed adjacent to a membrane having a nanopore therein, wherein said electrode is coupled to an electrical circuit that is adapted to generate an electrical signal to aid in the detection of said nucleic acid molecule or a portion thereof upon the flow of said nucleic acid molecule or portion thereof through or in proximity to said nanopore; (b) directing said nucleic acid molecule or portion thereof through or in proximity to said nanopore; and (c) identifying a nucleic acid sequence of said nucleic acid molecule or portion thereof at an accuracy of at least about 97%.

In another aspect, a system for sequencing a nucleic acid molecule comprises: (a) a chip comprising an array of individual sensors, wherein an individual sensor of said array comprises an electrode that is disposed adjacent to a membrane having a nanopore therein, wherein said electrode is coupled to an electrical circuit that is adapted to generate an electrical signal to aid in the detection of said nucleic acid molecule or a portion thereof upon the flow of said nucleic acid molecule or portion thereof through or adjacent to said nanopore; and (b) a processor coupled to said chip, wherein said processor is programmed to aid in characterizing a nucleic acid sequence of said nucleic acid molecule based on electrical signals received from said plurality of discrete sites at an accuracy of at least about 97%.

In another aspect, a method for sequencing a nucleic acid sample comprises detecting one or more nucleic acid subunits of said nucleic acid sample upon the flow of said nucleic acid sample through or in proximity to a nanopore, and sequencing said nucleic acid sample at an accuracy of at least about 97%.

In another aspect, a method for sequencing a nucleic acid sample comprises detecting one or more nucleic acid subunits of said nucleic acid sample upon the flow of said nucleic acid sample through or in proximity to a nanopore, and sequencing said nucleic acid sample at an error rate less than about 3%.

In another aspect, a method for sequencing a nucleic acid sample comprises (a) facilitating, without the use of a molecular motor, the flow of said nucleic acid sample through a nanopore embedded in a membrane; (b) detecting one or more nucleic acid subunits of said nucleic acid sample upon the flow of said nucleic sample through said nanopore; and (c) sequencing said nucleic acid sample upon detecting said one or more nucleic acid subunits.

In another aspect, a method for sequencing a nucleic acid sample comprises: (a) sensing, with the aid of a sensing circuit adjacent to a nanopore, one or more nucleic acid subunits of said nucleic acid sample upon the flow of said nucleic acid sample or a portion thereof through said nanopore without the aid of an enzyme; and (b) sequencing said nucleic acid sample upon sensing said one or more nucleic acid submits.

In another aspect, a method for nucleic acid sequencing comprises: (a) anchoring a nucleic acid molecule to a membrane having a nanopore therein; (b) threading said nucleic acid molecule or a portion thereof through or in proximity to the nanopore; and (c) sensing one or more individual bases of said nucleic acid molecule during step (b), wherein anchoring the nucleic acid molecule to said membrane prevents the nucleic acid molecule from threading completely through the nanopore.

In another aspect, a system for sensing a biological sample from a subject comprises: (a) a housing; (b) a sensor within the housing, the sensor having an electrical circuit adjacent to a membrane with a nanopore therein, wherein the electrical circuit is adapted to generate an electrical signal in response to the biological sample flowing through or adjacent to the nanopore; and (c) an identification member on or within the housing, the identification member having a unique identifier associated with the system and adapted to aid in associating the electrical signal, or characteristic information derived from the electrical signal, with the subject.

In another aspect, a method for manipulating a fluid on a surface comprises: (a) providing a surface, an array of electrodes in proximity to the surface, and a fluid comprising a hydrophilic phase and a hydrophobic phase, wherein said hydrophobic phase is adjacent to said surface; and (b) energizing the electrodes in a spatial and/or temporal pattern, thereby decreasing a volume of said hydrophobic phase in relation to said hydrophilic phase in proximity to said electrodes.

In another aspect, a biochip comprises a nanopore in a membrane that is disposed within, adjacent to, or in proximity to a well, wherein the well comprises an electrode that is capable of detecting a change in the flow of ions through said nanopore in response to a species passing through, in proximity to, or adjacent to the nanopore, wherein said electrode is capable of detecting said change in the flow of ions for at least 1 hour without re-adjusting the ion concentrations on either side of the membrane.

In another aspect, a method for preparing a biochip comprises: (a) providing a semiconductor substrate; (b) forming a plurality of wells in said semiconductor substrate at a density of at least 500 wells/mm$^2$; (c) forming an electrode in an individual well of said plurality, wherein said electrode is capable of performing electrical measurements of detectable species that are disposed on or adjacent to the semiconductor substrate, and wherein said electrode has an operating life of at least 15 minutes with 40 mV applied potential; and (d) preparing the substrate for the formation of a membrane that seals the individual well at a resistivity of at least about 10 gigaohms.

In another aspect, a biochip comprises (a) a plurality of electrically isolated wells at a density of at least 500 wells per square millimeter; and (b) a membrane that is disposed in or adjacent to an individual well of said plurality, wherein said membrane comprises a nanopore, and wherein said individual well comprises an electrode that detects a signal in response to the flow of ions through said nanopore.

In another aspect, a method for preparing a biochip comprises: (a) depositing silicon dioxide on a semiconductor substrate; (b) etching wells into the silicon dioxide, thereby providing wells in said semiconductor substrate at a density of at least 500 wells/mm$^2$; (c) forming metal electrodes in the wells; (d) removing metal from all areas of the substrate except for the wells; and (e) coating the substrate with a layer suitable for adhesion of a membrane.

In some embodiments, the metal electrodes are formed in the wells by (a) depositing a protective layer onto the well surface, wherein the protective layer (i) provides electrical connectivity to an underlying conductor, (ii) protects the underlying conductor from attack by a reactive solution, (iii) provides an electron source and/or sink so that an electrode material is not consumed in redox reactions, or (iv) any combination thereof; and (b) depositing the electrode material adjacent to said protective layer.

In another aspect, a method for preparing a biochip comprises: (a) providing a silicon oxide layer adjacent to a substrate, wherein said silicon oxide layer has a plurality of wells formed therein at a density of at least 500 wells/mm$^2$; (b) depositing a protective layer adjacent to an exposed surface of an individual well of said plurality; and (c) depositing an electrode adjacent to said protective layer.

In another aspect, a method for forming a biochip comprises forming a membrane adjacent to a silanized semiconductor surface, wherein said membrane fluidically isolates a first fluid from a second fluid with a resistivity of at least 10 gigaohms.

In another aspect, a method for preparing a biochip comprises: (a) providing a packaged biochip or biochip precursor having a surface that comprises silicon dioxide and/or a metal; and (b) silanizing the surface with an organofunctional alkoxysilane molecule.

In another aspect, a method for preparing a biochip comprises: (a) depositing a gel into a well that is in proximity to an electrode, wherein said electrode is coupled to a sensing circuit for sensing a species in a solution adjacent to said electrode; and (b) forming a membrane over the well, wherein the membrane is at least partially supported by the gel.

In another aspect, a biochip comprises a silicon oxide layer disposed adjacent to a substrate, wherein said silicon oxide layer comprises a well formed therein, wherein said well comprises a first layer of a corrosion resistant material and an electrode adjacent to said first layer, wherein said electrode is exposed to a fluid space.

In another aspect, a biochip comprises a plurality of wells and a membrane disposed in or adjacent to an individual well of said plurality of wells, wherein said membrane comprises a nanopore, and wherein said individual well comprises an electrode that detects a signal upon ionic flow through said pore in response to a species passing through or adjacent to said nanopore without being depleted.

In another aspect, a biochip is used to sequence a nucleic acid sample.

The biochip can be made by any of the methods described herein.

In another aspect, a biochip comprises an electrolyte in contact with a plurality of wells having a membrane comprising a nanopore disposed over the well and an electrode in the well, wherein the electrolyte does not comprise potassium ion.

In another aspect, a biochip comprises an electrolyte in contact with a plurality of wells having a membrane comprising a nanopore disposed over the well and an electrode in the well, wherein the electrolyte comprises tetramethylammonium chloride, triethylammonium chloride, ammonium chloride, potassium chloride, sodium chloride, or any combination thereof.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

In FIG. 1A, the nanopore is disposed upon the electrode; in FIG. 1B, the nanopore is inserted in a membrane over a well; and in FIG. 1C; the nanopore is disposed over a protruding electrode;

FIG. 28 shows an example of a semiconductor substrate;

DETAILED DESCRIPTION

Figure 1A:
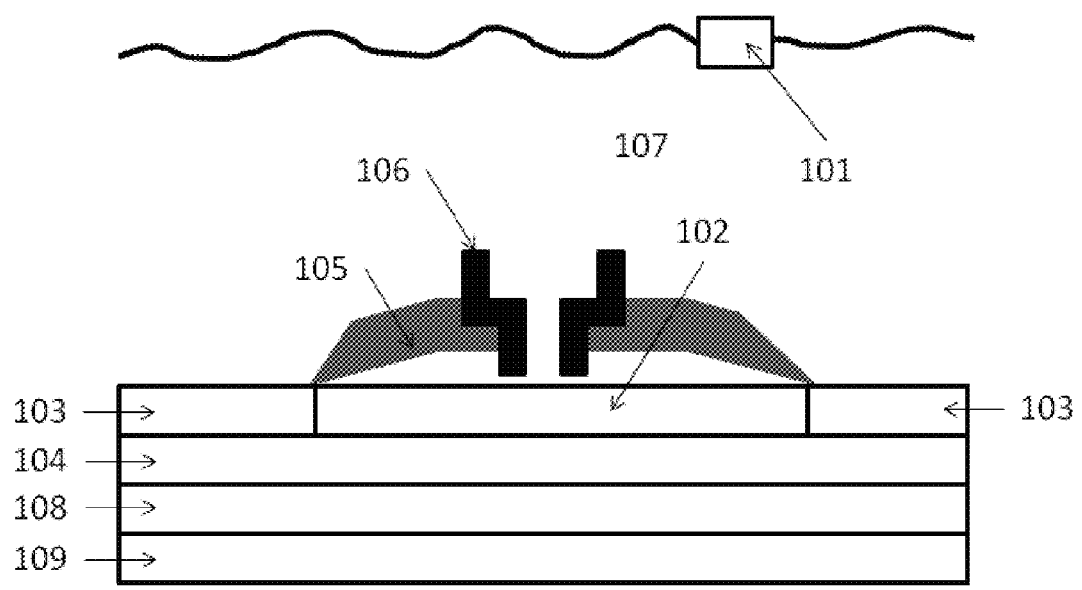
FIGS. 1A, 1B and 1C show examples of nanopore detectors.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nanopore," as used herein, generally refers to a pore, channel or passage formed or otherwise provided in a membrane. A membrane can be an organic membrane, such as a lipid bilayer, or a synthetic membrane, such as a membrane formed of a polymeric material. The membrane can be a polymeric material. The nanopore can be disposed adjacent or in proximity to a sensing circuit or an electrode coupled to a sensing circuit, such as, for example, a complementary metal-oxide semiconductor (CMOS) or field effect transistor (FET) circuit. In some examples, a nanopore has a characteristic width or diameter on the order of 0.1 nanometers (nm) to about 1000 nm. Some nanopores are proteins. Alpha hemolysin is an example of a protein nanopore.

The term "polymerase," as used herein, generally refers to any enzyme capable of catalyzing a polymerization reaction. Examples of polymerases include, without limitation, a nucleic acid polymerase or a ligase. A polymerase can be a polymerization enzyme.

The term "nucleic acid," as used herein, generally refers to a molecule comprising one or more nucleic acid subunits. A nucleic acid can include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid can be single-stranded or double stranded.

A "polynucleotide" or "oligonucleotide" is a polymer or oligomer comprising one or more nucleotide as defined herein. A polynucleotide or oligonucleotide can comprise a DNA polynucleotide or oligonucleotide, a RNA polynucleotide or oligonucleotide, or one or more sections of DNA polynucleotide or oligonucleotide and/or RNA polynucleotide or oligonucleotide.

As used herein, a "nucleotide" or "base" can be a primary nucleotide or a nucleotide analog. A primary nucleotide is deoxyadenosine mono-phosphate (dAMP), deoxycytidine mono-phosphate (dCMP), deoxyguanosine mono-phosphate (dGMP), deoxythymidine mono-phosphate (dTMP), adenosine mono-phosphate (AMP), cytidine mono-phosphate (CMP), guanosine mono-phosphate (GMP) or uridine mono-phosphate (UMP). A nucleotide analog is an analog or mimic of a primary nucleotide having modification on the primary nucleobase (A, C, G, T and U), the deoxyribose/ribose structure, the phosphate group of the primary nucleotide, or any combination thereof. For example, a nucleotide analog can have a modified base, either naturally existing or man-made. Examples of modified bases include, without limitation, methylated nucleobases, modified purine bases (e.g. hypoxanthine, xanthine, 7-methylguanine, isodG), modified pyrimidine bases (e.g. 5,6-dihydrouracil and 5-methylcytosine, isodC), universal bases (e.g. 3-nitropyrrole and 5-nitroindole), non-binding base mimics (e.g. 4-methylbezimidazole and 2,4-difluorotoluene or benzene), and no base (abasic nucleotide where the nucleotide analog does not have a base). Examples of nucleotide analogs having modified deoxyribose (e.g. dideoxynucleosides such as dideoxyguanosine, dideoxyadenosine, dideoxythymidine, and dideoxycytidine) and/or phosphate structure (together referred to as the backbone structure) includes, without limitation, glycol nucleotides, morpholinos, and locked nucleotides.

The present disclosure provides devices, systems and methods for species (e.g., atomic, molecular) detection and/or sequencing (e.g., nucleic acid sequencing). In some examples, a device of the present disclosure comprises an array of nanopores, such as at a density of at least about 100, 200, 300, 400, 500, 600, 700, 800, 900, 1000, 2000, 3000, 4000, 5000, 10000 sites per 1 $mm^2$. An individual site can include an individual nanopore sensor that can include one or more nanopores (e.g., 1, 2, 3, 4, 5, 6, 7, 8, 9, or 10 nanopores) in a membrane disposed adjacent to a sensing electrode. Such densities can be achieved by manufacturing methods provided herein. An individual nanopore can be in proximity to an electrode. The electrode can be independently addressable (e.g., addressed independently from another electrode), which can enable each nanopore to independently sense a different nucleic acid molecule. This can enable parallel sequencing (e.g., nucleic acid sequencing), which can provide for high accuracy sequencing, such as an accuracy of at least about 95%, about 95.5%, about 96%, about 96.5%, about 97%, about 97.5%, about 98%, about 98.5%, about 99%, about 99.5%, about 99.9%, about 99.99%, about 99.999%, or about 99.9999%.

For example, multiple copies of a nucleic acid molecule can be independently sequenced at a plurality of independently addressable nanopores to generate raw nucleic acid sequence data. The multiple copies can be generated, for example via nucleic acid amplification (e.g., polymerase chain reaction), from a single nucleic acid sample. Following sequencing, software executed by a computer processer of a system of the present disclosure can correct for errors in raw sequence data (e.g., by comparing the raw sequence data to detect abnormalities) and align the raw sequence data to generate a sequence of a nucleic acid sample. Under such an approach, a nucleic acid sample can be sequenced at an accuracy of at least about 95%, about 95.5%, about 96%, about 96.5%, about 97%, about 97.5%, about 98%, about 98.5%, about 99%, about 99.5%, about 99.9%, about 99.99%, about 99.999%, or about 99.9999%. Such accuracy can be achieved at a single pass of a nucleic acid molecule through or adjacent to a nanopore. In some cases, such accuracy can be achieved when identifying about 6, about 5, about 4, about 3, about 2 or about 1 nucleic acid bases. For example, a 97% accuracy is achieved when sequencing individual bases of a nucleic acid molecule using an nanopore sensor.

Using devices of the present disclosure, nucleic acid sample can be sequenced at an accuracy of at least about 95%, about 95.5%, about 96%, about 96.5%, about 97%, about 97.5%, about 98%, about 98.5%, about 99%, about 99.5%, about 99.9%, about 99.99%, about 99.999%, or about 99.9999% when sequencing a nucleic acid sample that has a lengths of at least about 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, or even 100000 or more bases. The determination of a nucleic acid sequence at such high accuracy, in some cases with the aid of redundant sequence information, can enable the nucleic acid sequence of a nucleic acid molecule to be determined substantially fast, such as in a time period that is less than or equal to about 1 day, 12 hours, 11 hours, 10 hours, 9 hours, 8 hours, 7 hours, 6 hours, 5 hours, 4 hours, 3 hours, 2 hours, 1 hour or less.

Nanopore devices of the present disclosure can generate redundant sequence information. In some examples, redundant sequence information can be generated by sequencing multiple copies of a nucleic acid molecule independently and in parallel, in some cases substantially simultaneously. Upon sequencing a given copy of the nucleic acid molecule, raw sequence information can be generated, which can be stored in a memory location of a system used to generate a nucleic acid sequence of the nucleic acid molecule. Raw sequences from other copies of the nucleic acid molecule can be stored in the memory location. An error correction algorithm (as may be implemented by software) can be used to compare the raw sequences to determine areas of overlap, and from the areas of overlap and sequences determine errors in the areas of overlap. In an example, the error is the actual sequence compared to the generated sequence. For example, if a given area in nine out of ten copies of the nucleic acid molecule has the generated sequence AAAAA, but one copy has AAAAT, then the AAAAT sequence can be deemed to be erroneous and discarded, and for the given area, the actual sequence can be determined to be AAAAA at high confidence (e.g., confidence of at least about 80%, 90%, 91%, 92%, 93%, 94%, 95%, or 99%). Such redundant sequence information can thus be used to decrease the error associated with a generated nucleic acid sequence. In some cases, redundant sequence information can decrease the error associated with a generated sequence even when an alignment algorithm (e.g., as implemented by alignment software) is used to generate a longer sequence of the nucleic acid molecule from individual smaller sequences.

Described herein are methods, devices and systems for sequencing nucleic acid molecules. In various aspects, the disclosure includes membranes and devices for use in molecular sensing comprising nanopores in a membrane. In some instances, it is advantageous to provide a biochip comprising a plurality of discrete sites (i.e., pixels). In some instances the sites are laid out in an array. In some instances, the biochip comprises nanopores, sensors, or any combination thereof, optionally embedded in or in proximity to a membrane as described herein.

Provided herein are systems and methods for sequencing a nucleic acid molecule with the aid of a nanopore. The nanopore can be formed or otherwise embedded in a membrane disposed adjacent to a sensing circuit, such as a field effect transistor or a complementary metal-oxide semiconductor (CMOS). In some cases, as a nucleic acid or tag flows through or adjacent to the nanopore, the sensing circuit detects an electrical signal associated with the nucleic acid or tag. The nucleic acid can be a subunit of a larger strand. The tag can be a byproduct of a nucleic acid incorporation event or other interaction between a tagged nucleic acid and the nanopore or a species adjacent to the nanopore, such as an enzyme that cleaves a tag from a nucleic acid.

In some embodiments, a detected signal can be collected and stored in a memory location, and later user to construct a sequence of the nucleic acid. The collected signal can be processed to account for any abnormalities in the detected signal, such as errors.

Methods for Sequencing a Nucleic Acid Sample

In an aspect, a method for sequencing a nucleic acid sample comprises directing the nucleic acid sample or a tag associated with the nucleic acid sample through or in proximity to a nanopore and sequencing nucleic acid bases of the nucleic acid sample at an accuracy of at least about 97%. In some embodiments, the nanopore is in a membrane. The nanopore can be a membrane protein, such as, for example, alpha hemolysin. In some embodiments, the membrane is a synthetic membrane. In some embodiments, the membrane is a lipid bilayer. The nanopore can be independently addressable.

In some instances, the determination of the nucleic acid sequence of a nucleic acid (e.g., DNA and RNA) includes errors. Example errors include, but are not limited to deletions (failing to detect a nucleic acid) insertions (detecting a nucleic acid where none are truly present) and substitutions (detecting the incorrect nucleic acid). In some embodiments, the accuracy of nucleic acid sequencing is determined by lining up the measured nucleic acid sequence with the true nucleic acid sequence (e.g., according to bioinformatics techniques) and determining the percentage of nucleic acid positions that are deletions, insertions and/or substitutions. The accuracy ranges from 0% to 100%, with 100% being a completely correct determination of the sequence of the nucleic acid. The error rate can be 100% minus the accuracy and can range from 0% to 100%, with 0% error rate being a completely correct determination of the sequence of the nucleic acid.

In various embodiments, the errors are any combination of deletions, insertions and substitutions. In some embodiments, the errors comprise few deletions. In some embodiments, about 70%, about 60%, about 50%, about 40%, about 30%, about 20%, about 10%, about 5%, or about 1% of the errors are deletions. In some embodiments, no more than 70%, no more than 60%, no more than 50%, no more than 40%, no more than 30%, no more than 20%, no more than 10%, no more than 5%, or no more than 1% of the errors are deletions.

In some embodiments, the accuracy of nucleic acid sequencing as performed according to the methods and/or using the devices described herein is high. The accuracy is any high value. In some instances, the accuracy is about 95%, about 95.5%, about 96%, about 96.5%, about 97%, about 97.5%, about 98%, about 98.5%, about 99%, about 99.5%, about 99.9%, about 99.99%, about 99.999%, about 99.9999%, and the like. In some instances, the accuracy is at least 95%, at least 95.5%, at least 96%, at least 96.5%, at least 97%, at least 97.5%, at least 98%, at least 98.5%, at least 99%, at least 99.5%, at least 99.9%, at least 99.99%, at least 99.999%, at least 99.9999%, and the like. In some instances, the accuracy is between about 95% and 99.9999%, between about 97% and 99.9999%, between about 99% and 99.9999%, between about 99.5% and 99.9999%, between about 99.9% and 99.9999%, and the like.

In some instances, high accuracy is achieved by performing multiple passes (i.e., sequencing a nucleic acid molecule a plurality of times, e.g., by passing the nucleic acid through or in proximity to a nanopore and sequencing nucleic acid bases of the nucleic acid molecule). In some cases, the data from multiple passes is combined (e.g., deletions, insertions and/or substitutions in a first pass are corrected using data from other repeated passes). In some embodiments, high accuracy is achieved with few passes (also referred to as reads, multiplicity of sequencing coverage). The number of passes is any number, and need not be an integer (e.g., 2.5 times). In some embodiments, the nucleic acid molecule is sequenced at least 1 time, 2 times, 3 times, 4 times, 5 times, 6 times, 7 times, 8 times, 9 times, 10 times, 12 times, 14 times, 16 times, 18 times, 20 times, 25 times, 30 times, 35 times, 40 times, 45 times, 50 times, and the like. In some embodiments, the nucleic acid molecule is sequenced at most 1 time, at most 2 times, at most 3 times, at most 4 times, at most 5 times, at most 6 times, at most 7 times, at most 8 times, at most 9 times, at most 10 times, at most 12 times, at most 14 times, at most 16 times, at most 18 times, at most 20 times, at most 25 times, at most 30 times, at most 35 times, at most 40 times, at most 45 times, at most 50 times, and the like. In some embodiments, the nucleic acid molecule is sequenced between about 1 time and 10 times, between about 1 time and 5 times, between about 1 time and 3 times, and the like. In some embodiments, the level of accuracy is achieved by combining data collected from at most 20 passes. In some embodiments, the level of accuracy is achieved by combining data collected from at most 10 passes. In some embodiments, the level of accuracy is achieved by combining data collected from at most 5 passes. In some embodiments, the level of accuracy is achieved in a single pass.

In some instances, groups of nucleic acids are identified using the methods and/or devices described herein. For example, a combination of three nucleic acids (e.g., adenine, cytosine and thymine) are determined by their characteristic effect on a voltage in a nanopore. In some instances, the accuracy of nucleic acid sequencing is high (e.g., at least 97%) when identifying about 6, about 5, about 4, about 3, about 2 or about 1 nucleic acid bases (i.e., as a group). In some instances, the accuracy of nucleic acid sequencing is high when identifying up to 6, up to 5, up to 4, up to 3, up to 2 or up to 1 nucleic acid bases (i.e., as a group). In some embodiments, the accuracy is at least about 97% when identifying single nucleic acid bases.

In an example, a method for sequencing a nucleic acid sample comprises detecting one or more nucleic acid subunits upon the flow of the nucleic acid sample through or in proximity to a nanopore at an error rate less than about 3%. In some instances, a low error rate is achieved with a low number of passes (e.g., 3% error rate in a single pass). The nucleic acid subunits comprise any suitable number of nucleic acids, for example about three nucleic acid bases or less. In some instances, the nucleic acid subunits comprise single nucleotides.

The error rate is any suitably low rate. In some instances, the error rate is about 10%, about 5%, about 4%, about 3%, about 2%, about 1%, about 0.5%, about 0.1%, about 0.01%, about 0.001%, about 0.0001%, and the like. In some instances, the error rate is at most 10%, at most 5%, at most 4%, at most 3%, at most 2%, at most 1%, at most 0.5%, at most 0.1%, at most 0.01%, at most 0.001%, at most 0.0001%, and the like. In some instances, the error rate is between 10% and 0.0001%, between 3% and 0.0001%, between 1% and 0.0001%, between 0.01% and 0.0001%, and the like.

In some instances, a nucleic acid molecule is sequenced by detecting signals from an electrode. The electrode can be part of a nanopore sensor. In some instances, the signals are electrical signals, which are generated upon the passage of a nucleic acid molecule through or in proximity to a nanopore. In some instances, tag molecules associated with the nucleic acid molecule (e.g., tags released upon nucleic acid polymerization events) pass into and out of, or through, the nanopore. In some instances, the signals are at least partially obscured by electrical noise. The ratio of the signal to the noise (e.g., ratio of their amplitudes) is any suitably high value (i.e., suitably high to achieve a certain accuracy). In some embodiments, the one or more nucleic acid subunits are detected at a signal to noise ratio of about 2 to 1, about 3 to 1, about 4 to 1, about 5 to 1, about 6 to 1, about 7 to 1, about 8 to 1, about 9 to 1, about 10 to 1, about 100 to 1, about 1,000 to 1, about 10,000 to one, and the like. In some embodiments, the one or more nucleic acid subunits are detected at a signal to noise ratio of at least about 10 to 1, at least about 100 to 1, at least about 1,000 to 1, at least about 10,000 to one.

The nucleic acid subunits can be detected within any suitable amount of time. In some embodiments, the one or more nucleic acid subunits are detected in a time period of about 1 second, about 1 milli-second (ms), about 1 micro-second ($\mu$s), and the like. In some embodiments, the one or more nucleic acid subunits are detected in a time period of at most 1 second, at most 1 milli-second, at most 1 micro-second, and the like. In some embodiments, the one or more nucleic acid subunits are detected in a time period of at least 1 second, at least 1 milli-second, at least 1 micro-second, and the like.

In some instances, the nucleic acid molecule and/or tag molecules associated with the nucleic acid molecule pass through the nanopore with a characteristic dwell time. In some instances, the dwell time is the average time at which a portion of a nucleic acid molecule (e.g., a single base, or a plurality of bases) or associated tag molecule is detectable in the nanopore (e.g., time period at which a signal is generated). In another aspect, the invention provides a method for sequencing a nucleic acid, the method comprising passing the nucleic acid through a nanopore at a dwell time, and detecting one or more nucleic acid subunits of the nucleic acid sample as it passes through the nanopore.

The dwell time can be any suitable amount of time (e.g., for achieving a certain accuracy). In some instances, the dwell time is about 100 milliseconds (ms), about 80 ms, about 60 ms, about 40 ms, about 20 ms, about 10 ms, about 1 ms, about 100 $\mu$s, about 80 $\mu$s, about 60 $\mu$s, about 40 $\mu$s, about 20 $\mu$s, about 10 $\mu$s, about 1 $\mu$s, and the like. In some instances, the dwell time is at least 100 ms, at least 80 ms, at least 60 ms, at least 40 ms, at least 20 ms, at least 10 ms, at least 1 ms, at least 100 microseconds ($\mu$s), at least 80 $\mu$s, at least 60 µs, at least 40 µs, at least 20 µs, at least 10 µs, at least 1 µs, and the like. In some instances, the dwell time is at most 100 ms, at most 80 ms, at most 60 ms, at most 40 ms, at most 20 ms, at most 10 ms, at most 1 ms, at most 100 µs, at most 80 µs, at most 60 µs, at most 40 µs, at most 20 µs, at most 10 µs, at most 1 µs, and the like. In some instances, the dwell time is between about 10 µs and 20 ms.

In some embodiments, the dwell time is sufficient to allow identification of subunits of up to about 5 bases. In some embodiments, the dwell time is sufficient to allow identification of subunits of up to about 3 bases. In some embodiments, the dwell time is sufficient to allow identification of subunits of up to about 1 base.

Another aspect of the present disclosure provides a method of obtaining sequence information of a nucleic acid. In some embodiments, the method comprises: (a) flowing the nucleic acid through a nanopore; (b) forming a speed bump-nucleic acid complex having at least one speed bump-nucleic acid duplex segment; (c) flowing the speed bump-nucleic acid complex through the nanopore until a speed bump-nucleic acid duplex segment is stopped before the constriction area of the nanopore; (d) obtaining electrical signals when the speed bump-nucleic acid duplex segment is stopped, and characterizing the nucleotide sequence that is adjacent to the first speed bump-nucleic acid duplex segment; and (e) dissociating the speed bump-nucleic acid complex and continuing the flow of the nucleic acid through the nanopore.

In this method, the speed bump-nucleic acid duplex comprises DNA or RNA base pair interactions between the speed bump oligonucleotide and the nucleic acid molecule. The duplex is dissociated by any suitable method including temperature, voltage, or any combination thereof. In some instances, voltage pulses are used to dissociate the speed bump molecules from the nucleic acid molecule.

In some instances, a high accuracy and/or low error rate is achieved by slowing the rate at which a nucleic acid molecule passes through or in proximity to a nanopore. In some instances, the nucleic acid molecule passes through the nanopore. In some instances, tag molecules released by nucleotide polymerization events pass through the nanopore. In some instances, the rate at which a nucleic acid molecule passes through or in proximity to a nanopore is sufficiently slow to achieve a certain dwell time (e.g., a dwell time sufficiently long to achieve a high signal to noise ratio and/or a high accuracy of nucleic acid sequencing).

In some instances, speed bump molecules are associated with the nucleic acid molecule to reduce or slow the rate at which a nucleic acid molecule passes through or in proximity to a nanopore. In some instances, the speed bump molecules comprise an oligonucleotide. In some embodiments, the speed bump molecules have a length of up to 2, 3, 4, 5, 6, 7, 8, 9, 10, 20, 30, 40, or 50 bases. In some embodiments, the oligonucleotides base-pair with the nucleic acid sequence. Such base pairing can involve covalent interactions between oligonucleotides. In some embodiments, the speed-bump molecule is dissociated from the nucleic acid as the nucleic acid passes through the nanopore.

Another aspect of the invention provides a method for sequencing a nucleic acid, the method comprising slowing the rate at which a nucleic acid passes through a nanopore by non-covalently associating a speed-bump molecule with the nucleic acid, where the nucleic acid is sequenced as the nucleic acid passes through the nanopore. Non-covalent associations can include, without limitation, ionic interaction and interactions due at least in part to London dispersion forces. The passage of the nucleic acid molecule through or in proximity to a nanopore is slowed by the non-covalently associated speed bump molecule.

Additional details can be found in PCT Patent Pub. No. WO/2012/088339 and PCT Patent Pub. No. WO/2012/088341, which are each herein incorporated by reference in their entirety.

Chip Set-Up

FIG. 1 shows an example of a nanopore detector (or sensor) having temperature control, as may be prepared according to methods described in U.S. Patent Application Publication No. 2011/0193570, which is entirely incorporated herein by reference. With reference to FIG. 1A, the nanopore detector comprises a top electrode 101 in contact with a conductive solution (e.g., salt solution) 107. A bottom conductive electrode 102 is near, adjacent, or in proximity to a nanopore 106, which is inserted in a membrane 105. In some instances, the bottom conductive electrode 102 is embedded in a semiconductor 103 in which is embedded electrical circuitry in a semiconductor substrate 104. A surface of the semiconductor 103 may be treated to be hydrophobic. A sample being detected goes through the pore in the nanopore 106. The semiconductor chip sensor is placed in package 108 and this, in turn, is in the vicinity of a temperature control element 109. The temperature control element 109 may be a thermoelectric heating and/or cooling device (e.g., Peltier device). In some instances, the bilayer spans and covers the electrode 102.

Multiple nanopore detectors may form a nanopore array. A nanopore array can include one or more nanopore detectors. In some cases, a nanopore array includes at least 1, 2, 3, 4, 5, 6, 7, 8, 9, 10, 100, 1000, 10000, or 100,000 nanopore detectors. An individual nanopore detector can include one or more nanopores adjacent to a sensing electrode (e.g., bottom conductive electrode 102). In some cases, an individual nanopore detector includes at least 1, 2, 3, 4, 5, 6, 7, 8, 9, 10, or 100 nanopores adjacent to a sensing electrode.

Figure 1B:
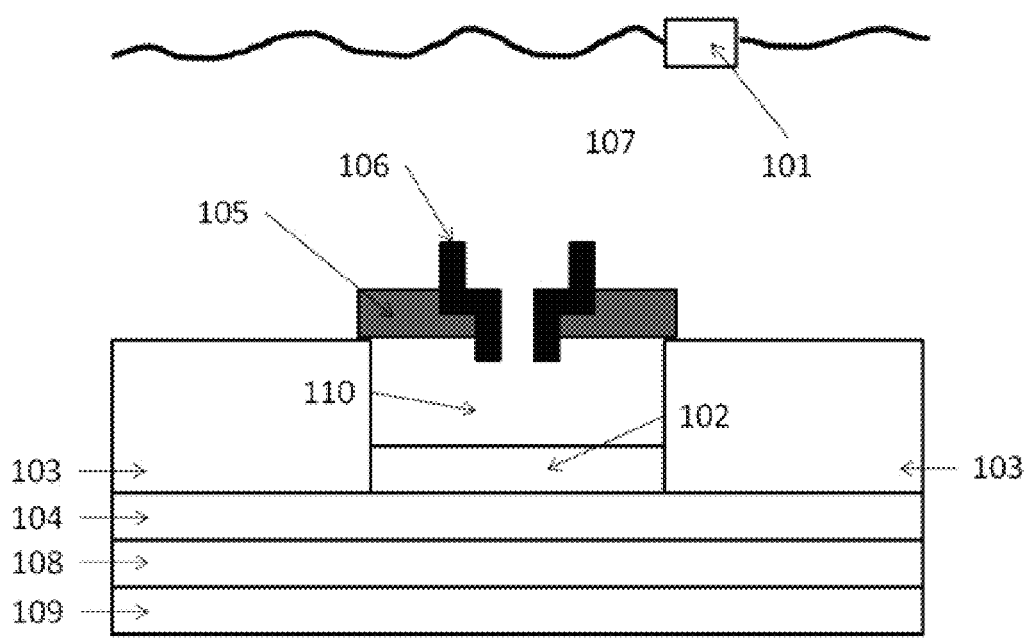
Figure 1C:
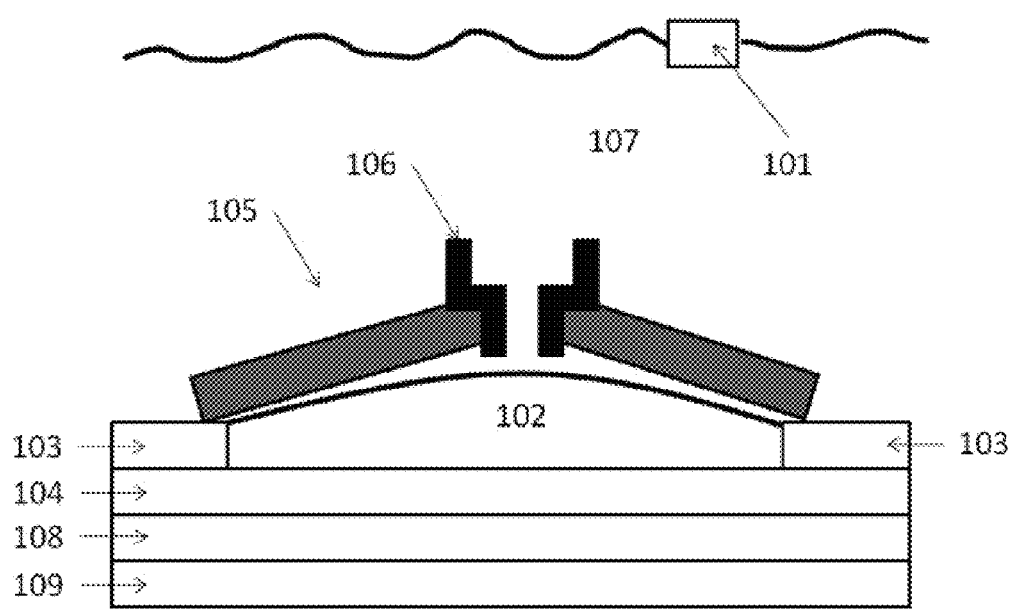

With reference to FIG. 1B, where like numerals represent like elements, the membrane 105 can be disposed over a well 110, where the sensor 102 forms part of the surface of the well. FIG. 1C shows an example in which the electrode 102 protrudes from the treated semiconductor surface 103.

In some examples, the membrane 105 forms on the bottom conductive electrode 102 and not on the semiconductor 103. The membrane 105 in such a case may form coupling interactions with the bottom conductive electrode 102. In some cases, however, the membrane 105 forms on the bottom conductive electrode 102 and the semiconductor 103. As an alternative, the membrane 105 can form on the semiconductor 103 and not on the bottom conductive electrode 102, but may extend over the bottom conductive electrode 102.

In some cases, the sensors and/or electrodes can be individually or independently addressed. Individually and/or independently addressable sensors can be controlled and/or have data read from each of the sensors and/or electrodes.

A given nanopore sensor can be independently addressable. This can provide for parallel sequencing and the generation of redundant sequence information, which can be used to generate nucleic acid sequence information at high accuracy (e.g., greater than or equal to about 97%). As an alternative, a group of nanopore sensors can be independently addressable. The group of nanopore sensors can include at least about 2, 3, 4, 5, 6, 7, 8, 9, 10, 20, 30, 40, 50, 100, 200, 300, 400, or 500 individual nanopore sensors. In such a case, a given group of nanopore sensors can be controlled independently from another group of nanopore sensors.

High Pixel Densities

In some instances, it is advantageous to provide a system comprising a high density of discrete sites. For example, a large number of sites per unit area (i.e., density) allows for the construction of smaller devices, which are portable, low-cost, or have other advantageous features. In some embodiments, provision of a high density of discrete sites allows for more sites upon which to perform reactions, make measurements, and the like. In one example, a large number of sites comprising a nanopore and a sensing circuit allows for a large number of nucleic acid molecules to be sequenced at once. Such a system can increase the through-put and/or decrease the cost of sequencing a nucleic acid sample.

In an aspect, a system comprises a substrate with a surface comprising discrete sites, an individual site of the discrete sites having a nanopore and a sensing circuit adjacent to the nanopore. Examples of suitable nanopores and sensing circuits are described herein. In some embodiments, the system further comprises a flow cell in fluid communication with the substrate, the flow cell adapted to deliver one or more reagents to the substrate.

The surface comprises any suitable density of discrete sites (e.g., a density suitable for sequencing a nucleic acid sample in a given amount of time or for a given cost). In one embodiment, the surface has a density of discrete sites greater than or equal to about 500 sites per 1 $mm^2$. In some embodiments, the surface has a density of discrete sites of about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 sites per 1 $mm^2$. In some embodiments, the surface has a density of discrete sites of at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000, at least 20000, at least 40000, at least 60000, at least 80000, at least 100000, or at least 500000 sites per 1 $mm^2$. Such pixel densities may be achieved using manufacturing methods of the present disclosure, as described below and elsewhere herein. In an example, a pixel density of at least about 500 sites per 1 $mm^2$ is achieved by forming wells at a density of at least about 500 sites per 1 $mm^2$, and forming nanopore sensors (e.g., membrane with a nanopore therein) in each well. Higher densities (e.g., at least 600, 700, 800, 900, 1000, 10000 sites per 1 $mm^2$) may be achieved by selecting processing conditions to form wells at higher densities.

In some embodiments, the nanopore is a protein. An example of a nanopore is alpha hemolysin. In some embodiments, the nanopore has a diameter of about 100 Å or less. In some embodiments, the nanopore has a diameter of about 50 Å or less. Thus, in some instances, the ability to achieve a high number of discrete sites per unit of area is determined by the size of the sensing circuit.

In some embodiments, the sensing circuit comprises few transistors. The sensor circuit can comprise any suitable number of transistors (e.g., as few as are needed to detect a signal). In some embodiments, the sensing circuit comprises 1, 2, 3, 4, 5, 6, 7, 8, 9, 10, 11, 12, 13, 14, 15, 16, 17, 18, 19, or 20 transistors. In some embodiments, the sensing circuit comprises at most 1, at most 2, at most 3, at most 4, at most 5, at most 6, at most 7, at most 8, at most 9, at most 10, at most 11, at most 12, at most 13, at most 14, at most 15, at most 16, at most 17, at most 18, at most 19, or at most 20 transistors. One suitable embodiment for providing a system comprising a substrate with a surface comprising a high density of discrete sites, where the sites comprise a sensing circuit is as follows.

Compact Sensing Circuitry

Figure 2:
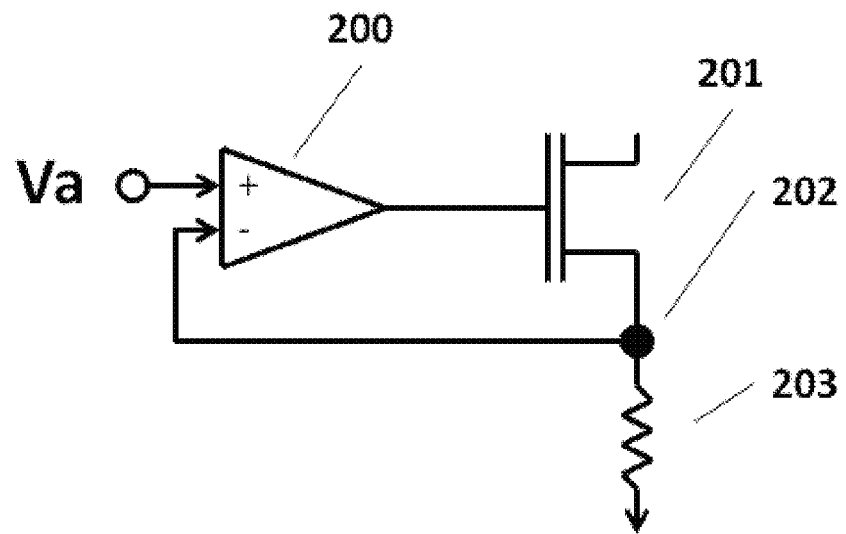
FIG. 2 shows an example of an ultra compact measurement circuit.

An example of cell circuitry is shown in FIG. 2. An applied voltage Va is applied to an opamp 1200 ahead of a metal-oxide-semiconductor field-effect transistor (MOSFET) current conveyor gate 201. Also shown here are an electrode 202 and the resistance of the nucleic acid and/or tag detected by the device 203.

An applied voltage Va can drive the current conveyor gate 201. The resulting voltage on the electrode sis then Va−Vt where Vt is the threshold voltage of the MOSFET. In some instances, this results in limited control of the actual voltage applied to the electrode as a MOSFET threshold voltage can vary considerably over process, voltage, temperature, and even between devices within a chip. This Vt variation can be greater at low current levels where sub-threshold leakage effects can come into play. Therefore, in order to provide better control of the applied voltage, an opamp can be used in a follower feedback configuration with the current conveyor device. This ensures that the voltage applied to the electrode is Va, independent of variation of the MOSFET threshold voltage.

Figure 3:
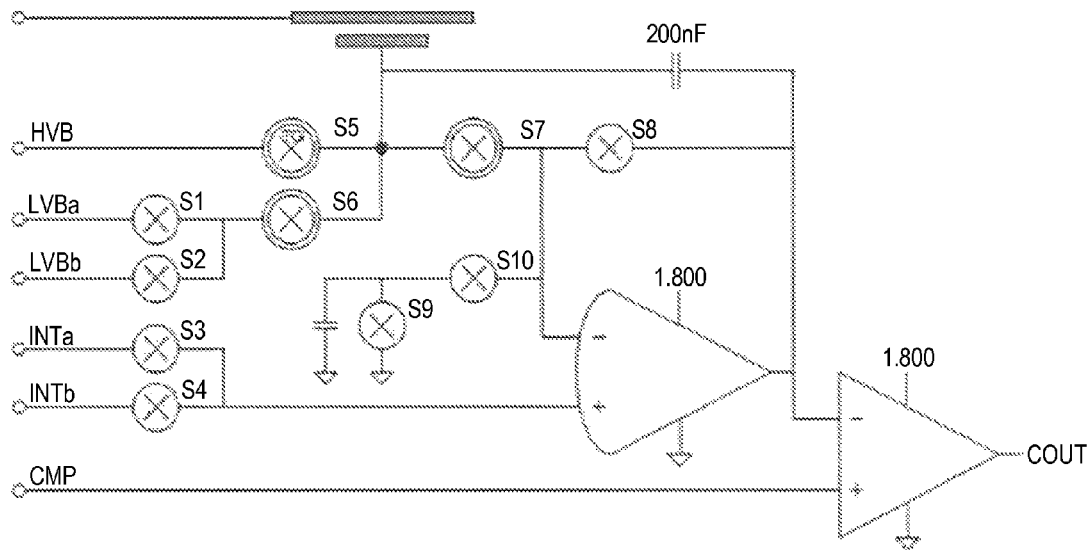
FIG. 3 shows an example of an ultra compact measurement circuit.
Figure 3:
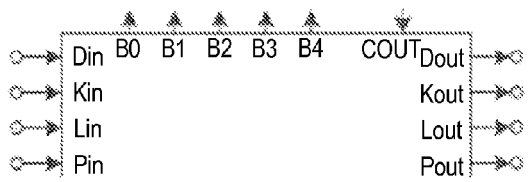

Another example of cell circuitry is shown in FIG. 3 and includes an integrator, comparator, and digital logic to shift in control bits and simultaneously shift out the state of the comparator output. The cell circuitry may be adapted for use with systems and methods provided herein. The B0 through B1 lines may come out of the shift register. The analog signals are shared by all cells within a bank while digital lines may be daisy-chained from cell to cell.

The cell digital logics comprises the 5 bit data shift register (DSR), 5 bit parallel load registers (PLR), control logic, and analog integrator circuit. Using the LIN signal, the control data shifted into the DSR is parallel loaded into the PLR. These 5 bits control digital "break-before-make" timing logic which controls the switches in the cell. In addition the digital logic has a set-reset (SR) latch to record the switching of the comparator output.

The architecture delivers a variable sample rate that is proportional to the individual cell current. A higher current may result in more samples per second than a lower current. The resolution of the current measurement is related to the current being measured. A small current may be measured with finer resolution than a large current, which may be a benefit over fixed resolution measurement systems. There is an analog input which allows the user to adjust sample rates by changing the voltage swing of the integrator. It may be possible to increase the sample rate in order to analyze biologically fast processes or to slow the sample rate (and thereby gain precision) in order to analyze biologically slow processes.

The output of the integrator is initialized to the voltage low voltage bias (LVB) and integrates up to the voltage chemical mechanical planarization (CMP). A sample is generated every time the integrator output swings between these two levels. Thus the greater the current the faster the integrator output swings and therefore the faster the sample rate. Similarly if CMP voltage is reduced the output swing of the integrator needed to generate a new sample is reduced and therefore the sample rate is increased. Thus simply reducing the voltage difference between LVB and CMP provides a mechanism to increase the sample rate.

A nanopore based sequencing chip may incorporate a large number of autonomously operating or individually addressable cells configured as an array. For example an array of one million cells could be constructed of 1000 rows of cells by 1000 columns of cells. This array enables the parallel sequencing of nucleic acid molecules by measuring the conductance difference when tags released upon nucleotide incorporation events are detected by the nanopore for example. Moreover this circuitry implementation allows the conductance characteristics of the pore-molecular complex to be determined which may be valuable in distinguishing between tags.

The integrated nanopore/bilayer electronic cell structures may apply appropriate voltages in order to perform current measurements. For example, it may be necessary to both (a) control electrode voltage potential and (b) monitor electrode current simultaneously in order to perform correctly.

Moreover it may be necessary to control cells independently from one another. The independent control of a cell may be required in order to manage a large number of cells that may be in different physical states. Precise control of the piecewise linear voltage waveform stimulus applied to the electrode may be used to transition between the physical states of the cell.

In order to reduce the circuit size and complexity it may be sufficient to provide logic to apply two separate voltages. This allows two independent grouping of cells and corresponding state transition stimulus to be applied. The state transitions are stochastic in nature with a relatively low probability of occurrence. Thus it may be highly useful to be able to assert the appropriate control voltage and subsequently perform a measurement to determine if the desired state transition has occurred. For example the appropriate voltage may be applied to a cell and then the current measured to determine whether a bilayer has formed. The cells are divided into two groups: (a) those which have had a bilayer form and no longer need to have the voltage applied. These cells may have a 0V bias applied in order to effect the null operation (NOP)—that is stay in the same state and (b) those which do not have a bilayer formed. These cells will again have the bilayer formation electric voltage applied.

A substantial simplification and circuit size reduction may be achieved by constraining the allowable applied voltages to two and iteratively transitioning cells in batches between the physical states. For example, a reduction by at least a factor of 1.1, 2, 3, 4, 5, 6, 7, 8, 9, 10, 20, 30, 40, 50, or 100 may be achieved by constraining the allowable applied voltages.

In some examples, a test chip includes an array of 264 sensors arranged in four separate groups (aka banks) of 66 sensor cells each. Each group is in turn divided into three "columns" with 22 sensors "cells" in each column. The "cell" name is apropos given that ideally a virtual cell consisting of a bi-lipid layer and inserted nanopore is formed above each of the 264 sensors in the array (although the device may operate successfully with only a fraction of the sensor cells so populated).

There is a single analog I/O pad which applies a voltage potential to the liquid contained within a conductive cylinder mounted to the surface of the die. This "liquid" potential is applied to the top side of the pore and is common to all cells in a detector array. The bottom side of the pore has an exposed electrode and each sensor cell may apply a distinct bottom side potential to its electrode. The current is then measured between the top liquid connection and each cell's electrode connection on the bottom side of the pore. The sensor cell measures the current traveling through the pore as modulated by the tag molecule passing within the pore.

Figure 4:
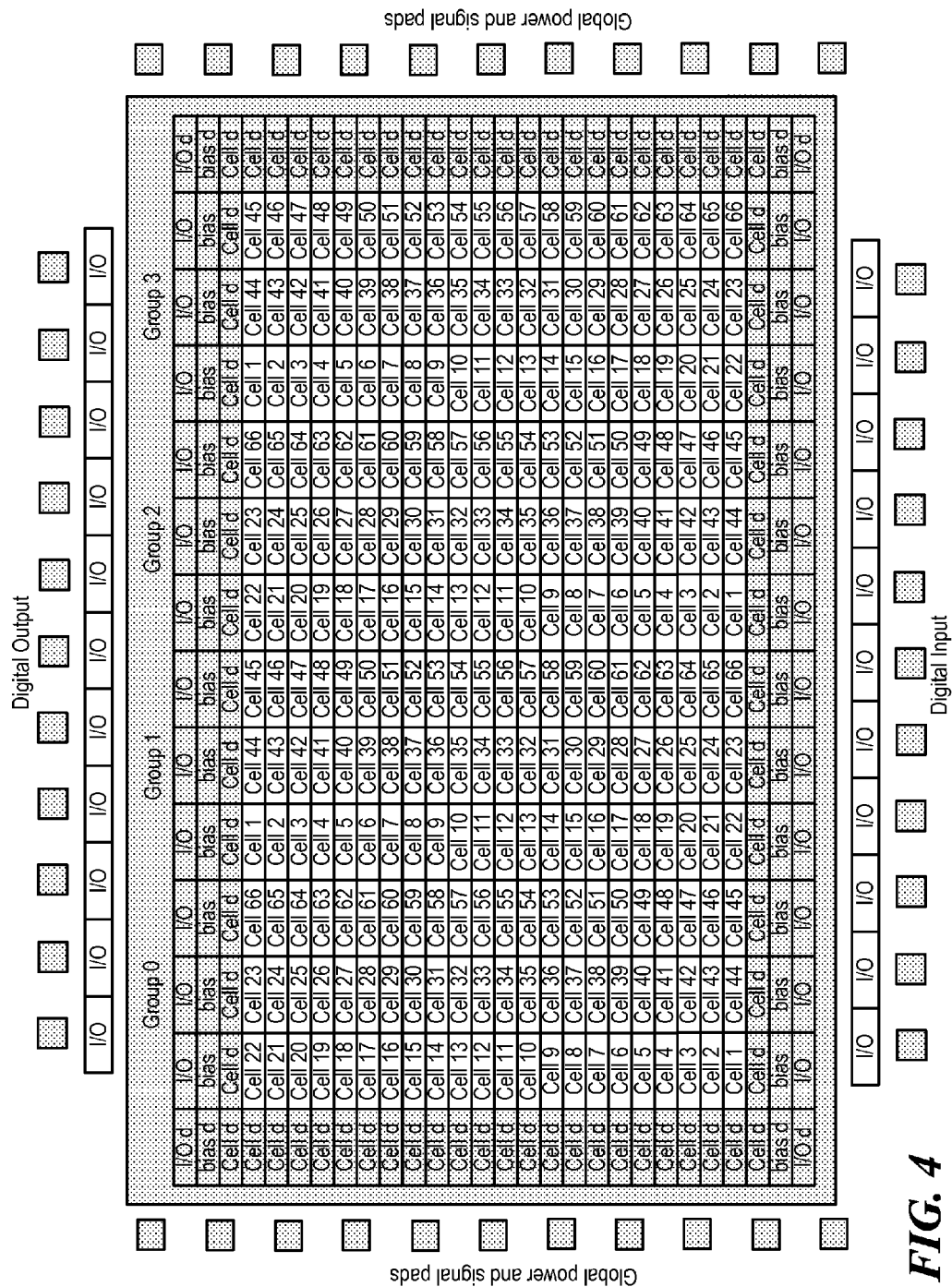
FIG. 4 shows an example of a test chip cell array configuration.

In some cases, five bits control the mode of each sensor cell. With continued reference to FIG. 4, each of the 264 cells in the array may be controlled independently. Values are applied separately to a group of 66 cells. The mode of each of the 66 cells in a group is controlled by serially shifting in 330 (66* 5bits/cell) digital values into a DataShiftRegister (DSR). These values are shifted into the array using the KIN (clock), and DIN (dat in) pins with a separate pin pair for each group of 66 cells.

Thus 330 clocks are used to shift 330 bits into the DSR shift register. A second 330 bit Parallel Load Register (PLR) is parallel loaded from this shift register when the corresponding LIN<i> (Load Input) is asserted high. At the same time as the PLR is parallel loaded the status value of the cell is loaded into the DSR.

A complete operation may consist of 330 clocks to shift in 330 data bits into the DSR, a single clock cycle with LIN signal asserted high, followed by 330 clock cycles to read the captured status data shifted out of the DSR. The operation is pipelined so that a new 330 bits may be shifted into the DSR simultaneously while the 330 bits are being read out of the array. Thus at 50 MHz clock frequency the cycle time for a read is 331/50 MHz=6.62 us.

Combined AC and DC Stimulus

As described herein, the electrical stimulus can be various electrical stimuli, such as an applied current and an applied voltage. The current can be a direct current (DC) and/or an alternating current (AC). The electrical stimulus can constitute a series of electrical pulses. An electrical stimulus can be applied via an electrode, such as an electrode of a nanopore.

In some instances, the stimulus is a varying electrical stimulus (e.g., the electrical stimulus changes over time). In some instances, the stimulus comprises pulses (e.g., rapid and transient changes from a baseline). In some instances, the stimulus is a waveform (e.g., a sine wave, square wave, triangular wave, or saw tooth wave).

In some embodiments, the electrical stimulus is the combination of an AC pulse and a DC bias. In some instances, AC pulses are applied on top of a DC stimulus. In some instances, the DC stimulus does not vary (i.e., is constant).

Non-Sacrificial Electrodes

In some embodiments, the electrodes described herein are sacrificial electrodes. Sacrificial electrodes may be depleted when they are used (e.g., when they are detecting signals). Silver chloride (AgCl) is one example of a sacrificial electrode. In some instances, the amount of time that an electrode can be used is limited by the sacrificial nature of the electrode material. In some embodiments, the electrode is replenished after a period of use. Replenishment can comprise reversing the direction of flow of an electrochemical reaction that leads to the depletion of the electrode, such as by reversing the voltage applied to an electrode.

In some embodiments, the electrodes described herein are not sacrificial (or non-sacrificial) electrodes. In some instances, the electrodes are not depleted or substantially depleted when they are used (e.g., when they are detecting signals). Electrodes comprising platinum are one example of a non-sacrificial electrode. A non-sacrificial electrode may not need to be replenished during an operating lifetime of a nanopore detector, which can be at least about 5 minutes, 10 minutes, 30 minutes, 1 hour, 2 hours, 3 hours, 4 hours, 5 hours, 6 hours, 12 hours, or 1 day.

In some instances, the electrodes have a low signal to noise ratio. For example, some non-sacrificial electrodes have a low signal to noise ratio. In some embodiments, the electrodes described herein are used to detect signals for nucleic acid sequencing. The signal to noise ratio for nucleic acid sequencing can be increased (e.g., when using non-sacrificial electrodes) by using ferrocyanide tags. Ferrocyanide ($[Fe(CN)_6]^{4-}$) and its oxidized product ferricyanide ($[Fe(CN)_6]^{3-}$) are mostly impermeable to membranes (e.g., lipid bilayers). In some embodiments, nucleotides are tagged with molecules comprising ferrocyanide and a nucleic acid molecule is replicated (e.g., by DNA polymerase), whereby the ferrocyanide tags are released from the nucleotide and pass through a nanopore, where they are detected by the sensors (e.g., non-sacrificial electrodes) as described herein.

Ionic and Non-Ionic Chemistry

The operating voltages for operation of the chip may be at least partially determined by the salt concentration. In general, higher salt concentration results in higher current for the same applied voltage. In some embodiments, a +/−320 mV range is used for a salt concentration (e.g., KCl) of approximately 1 M. If the salt concentration is about 0.3 M the working voltages may be about +/−500 mV. The particular voltage and salt concentrations described herein are illustrative and not limiting.

The electrodes may be silver electrodes. For example, KCl passes an ionic current by the silver electrode, turning it from silver to AgCl at the positive electrode and at the negative electrode turning AgCl to silver. In the case of silver electrodes, the electrodes themselves are affected by the operation of the nanopore system.

In some cases, the system and/or chip does not use a conductive salt solution. Some redox molecules may be substituted for salts. For example, the redox molecule may be ferrocene carboxylate. In this case, the redox molecule changes to an oxidized state (e.g., $Fe^{+3}$) at a first electrode and gives up an electron at a second electrode, where the redox molecule is reduced (e.g., to $Fe^{+2}$). The concentration of the redox molecule is any suitable concentration. In an embodiment, ferrocene carboxylate is used at a concentration between about 100 mM and 1M. In some embodiments, the concentration of the redox molecule is at least about 10 mM, at least about 20 mM, at least about 40 mM, at least about 60 mM, at least about 80 mM, at least about 100 mM, at least about 200 mM, at least about 500 mM, at least about 1 M, or at least about 10 M.

In the redox molecule system, the electrodes can be a platinum sense electrode and a silver or platinum reference electrode. In the redox set-up the electrodes may not be affected by the operation of nanopore set-up and/or the passing of the current (e.g., the electrodes are not sacrificial). In some embodiments, the redox molecule system can lead to longer electrode life.

In some cases, the downside of using redox molecules rather than ions can be lower current readings than the silver electrode system. In some embodiments, the current readings are sufficiently high for the nanopore to detect the cleaved tags that pass through the pore (e.g., from the synthesis of an antisense strand with tagged-nucleotides).

Functional Membranes

In an aspect, described herein are "functional membranes". Functional membranes can have a certain resistance, capacitance and/or conductance per mol of electrolyte. In some instances, functional membranes comprise nanopores. In some instances, functional membranes do not comprise nanopores (e.g., is nanopore-less). In some embodiments, functional membranes are disposed upon a membrane-incompatible surface. There is no covalent bond between the membrane and the surface in some instances. The membrane or membrane material (e.g., lipids) can adhere to the surface. In some embodiments, the membrane can be tethered to the surface (i.e., covalently through a linking moiety), however tethered membranes should generally be constructed so as to prevent leakage of electrolyte between the membrane and the surface. In some embodiments, functional membranes are disposed in sensing proximity to an integrated circuit, as described below. The membrane incompatible surface and the integrated circuit are essentially planar (comprise a common plane) in some instances. In some embodiments, the integrated circuit sensor is hydrophilic and a lipid bilayer forms over the sensing circuit while a lipid monolayer forms over the membrane incompatible surface with the lipid tails oriented toward the membrane incompatible surface.

The functional membrane has any suitable capacitance. In some embodiments, the membrane has a capacitance of about 0.1, about 0.5, about 1, about 2, about 3, about 4, about 5, about 6, about 7, about 8, about 9, about 10, about 20, or about 50 fF/μm². In some embodiments, the membrane has a capacitance of greater than about 0.1, greater than about 0.5, greater than about 1, greater than about 2, greater than about 3, greater than about 4, greater than about 5, greater than about 6, greater than about 7, greater than about 8, greater than about 9, greater than about 10, greater than about 20, or greater than about 50 fF/μm². In some embodiments, the membrane has a capacitance of less than about 0.1, less than about 0.5, less than about 1, less than about 2, less than about 3, less than about 4, less than about 5, less than about 6, less than about 7, less than about 8, less than about 9, less than about 10, less than about 20, or less than about 50 fF/μm². The functional membrane can have no nanopores (i.e., the functional membrane is nanopore-less), or at least 1, 2, 3, 4, 5, 6, 7, 8, 9, 10 nanopores. The capacitance can be as measured by an electrode under an applied voltage of at least about 50 mV.

The functional membrane has any suitable resistance. In some embodiments, the membrane has a resistance of about 100 mega-ohms (MΩ), about 200 MΩ, about 300 MΩ, about 400 MΩ, about 500 MΩ, about 1 giga-ohm (GΩ), about 5 GΩ, about 10 GΩ, about 50 GΩ, about 100 GΩ, or about 500 GΩ. In some cases, the membrane has a resistance of at least about 100 at least mega-ohms (MΩ), at least about 200 MΩ, at least about 300 MΩ, at least about 400 MΩ, at least about 500 MΩ, at least about 1 giga-ohm (GΩ), at least about 5 GΩ, at least about 10 GΩ, at least about 50 GΩ, at least about 100 GΩ, or at least about 500 GΩ. In some cases, the membrane has a resistance of at least about 100 at most mega-ohms (MΩ), at most about 200 MΩ, at most about 300 MΩ, at most about 400 MΩ, at most about 500 MΩ, at most about 1 giga-ohm (GΩ), at most about 5 GΩ, at most about 10 GΩ, at most about 50 GΩ, at most about 100 GΩ, or at most about 500 GΩ. In some cases, a membrane that has no nanopore has a resistance of at least 10 GΩ, a membrane that has one nanopore has a resistance from 1 GΩ to 10 GΩ and a membrane that has two or more nanopores has a resistance from 500 MΩ to 1 GΩ inclusive. The resistance can be as measured by an electrode under an applied voltage of at least about 50 mV.

The functional membrane has any suitable conductance. In some instances, the conductance is measured per mole of electrolyte. In some embodiments, the membrane has a conductance of about 0.02, about 0.05, about 0.1, about 0.25, about 0.5, about 1, about 2, or about 5 nano Siemens per mole of electrolyte. In some embodiments, the membrane has a conductance of greater than about 0.02, greater than about 0.05, greater than about 0.1, greater than about 0.25, greater than about 0.5, greater than about 1, greater than about 2, or greater than about 5 nano Siemens per mole of electrolyte. In some embodiments, the membrane has a conductance of less than about 0.02, less than about 0.05, less than about 0.1, less than about 0.25, less than about 0.5, less than about 1, less than about 2, or less than about 5 nano Siemens per mole of electrolyte. The conductance can be as measured by an electrode under an applied voltage of at least about 50 mV.

In some embodiments, the membranes have any capacitance selected from the list above or any conductance selected from the list above. In some embodiments, the membranes have any capacitance selected from the list above and any conductance selected from the list above.

In an example, a nanopore device comprises a membrane disposed upon a membrane-incompatible surface in sensing proximity to an integrated circuit. The membrane, as measured by the integrated circuit, can exhibit (i) a capacitance greater than about 5 $fF/\mu m^2$ or a conductance less than about 0.25 nano Siemens per mole of electrolyte or (ii) a capacitance greater than about 5 $fF/\mu m^2$ per square micron and a conductance less than about 0.25 nano Siemens per mole of electrolyte.

In some examples, a device for molecular sensing comprises one or more nanopores in a membrane disposed upon at least one membrane incompatible surface in sensing proximity to an integrated circuit. Examples of membranes, membrane incompatible surfaces, optional tethers, integrated circuits and nanopores are described herein. In some instances, the device comprises a functional membrane (e.g., as described herein) in sensing proximity to an integrated circuit. As used herein, "sensing proximity" means that the membrane is sufficiently close to the sensor such that the sensor is capable of detecting a signal originating from the membrane. Nucleic acid sequencing is one example of molecular sensing.

In some embodiments, the integrated circuit is an individually addressable integrated circuit. That is, data can be collected from and/or signals can be sent to each integrated circuit of a plurality of integrated circuits. The ultra compact integrated circuit described above is one example of an acceptable integrated circuit. In some embodiments, the integrated circuit comprises a logic controller. Examples of logic controllers are described in U.S. Patent Pub. No. 2011/0192723, which is entirely incorporated by reference herein, and may include any controller suitable for nucleic acid sequencing, for example.

In some examples, a nanopore device for use in molecular sensing comprises one or more nanopores in a membrane disposed upon at least one membrane incompatible surface in sensing proximity to an integrated circuit, the membrane having the one or more nanopores exhibiting (i) a capacitance greater than about 5 $fF/\mu m^2$ per square micron or a conductance less than about 10 nano Siemens per mole of electrolyte per nanopore as measured by the sensing integrated circuit, or (ii) a capacitance greater than about 5 $fF/\mu m^2$ and a conductance less than about 10 nano Siemens per mole of electrolyte per nanopore as measured by the sensing integrated circuit. An individual nanopore can be independently addressable.

Cross-Linked and Other Membranes

Devices of the present disclosure can include membranes. A membrane can be an organic or inorganic membrane. In some examples, a membrane is a lipid bilayer. In some embodiments, the membrane is any membrane suitable for the insertion of a protein (e.g., alpha hemolysin). During set up or use of the device, the membrane can be in contact with an ionic solution (e.g., for inserting proteins as described herein). In some instances, the membrane is flexible (i.e., is not brittle and/or can be deformed without breaking) In some instances, the membrane comprises a plurality of molecules and/or modules that can expand, deform, re-arrange relative to one another, and the like (e.g., to accommodate insertion of a protein into the membrane). In some instances, the membrane is below its glass transition temperature.

In some instances, the membrane is hydrophobic. The membrane can comprise hydrophobic portions (e.g., the tails of phospholipids facing the inside of a lipid bilayer) and hydrophilic portions (e.g., the phospholipid heads facing the outside of a lipid bilayer).

In some cases, the membrane is thin (e.g., the width of two lipid molecules). The membrane has any suitable thickness (e.g., a thickness suitable for inserting a protein and/or for performing nucleic acid sequencing). In some embodiments, the membrane is about 2, about 3, about 4, about 5, about 6, about 7, about 8, about 9, about 10, about 15, about 20, about 25, about 30, about 50, about 100, about 200, about 300, about 400, about 500, or about 1000 nanometers (nm) thick. In some embodiments, the membrane is at most 2, at most 3, at most 4, at most 5, at most 6, at most 7, at most 8, at most 9, at most 10, at most 15, at most 20, at most 25, at most 30, at most 50, at most 100, at most 200, at most 300, at most 400, at most 500, or at most 1000 nm thick. In some instances, the membrane has a thickness between about 1 nm and 50 nm, or 2.5 nm and about 10 nm.

In some embodiments, the membrane comprises polymers. In some instances, the polymers are a minor component (e.g., incorporated into a lipid bilayer at any suitable proportion including at most 1%, at most 5%, at most 10%). In some embodiments, the majority (e.g., at least 70%, at least 80%, at least 90%, at least 99%) of the membrane comprises polymer by mass. In some instances, the membrane comprises polymer and membrane proteins.

The polymer can be naturally sourced, man-made, or a combination thereof. Examples of man-made polymers include neoprene, polyvinylchloride, polystyrene, polyethylene, polypropylene, polyacrylonitrile, silicone, and many more. In some instances the polymer is a block co-polymer. In some instances, the polymer is branched.

In some instances, the membrane is a lipid bilayer. In some instances, the membrane is not a lipid bilayer. In some embodiment, the membrane comprises lipids. In some instances, the membrane comprises analogs of lipids, chemically modified lipids, or derivatized lipids.

In some instances, the membrane comprises a long carbon chain. The length of the carbon chain is any suitable number of carbons, including 2, 3, 4, 5, 6, 7, 8, 9, 10, 11, 12, 13, 14, 15, 16, 17, 18, 19, 20, 21, 22, 23, 24, 25, 30, 35, 40, 45, or 50 carbons. In some instances, the carbon chain comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 35, at least 40, at least 45, or at least 50 carbons. In some instances, the carbon chain is branched. In some instances, the carbon chain is not branched.

In some embodiments, the membrane comprises cross-linked lipids. The lipids can be polymerizable. In an example of a cross-linked lipid, pairs of phosphatidylcholine lipids are designed to cross-link at the termini of their 2-position acyl chain upon the formation of lipid bilayers. In some instances, the cross-linked lipids span the lipid bilayer, resembling naturally occurring bolaamphiphiles that stabilize archaebacterial membranes against high temperatures.

Three example cross-linking reactions include the acyl chain cross-linking between thiol and bromine groups, thiol and acryloyl groups, and cyclopentadiene and acryloyl groups. Examples of cross-linked lipids are described in Halter, et. al. Langmiur, Mar. 16, 2004 20(6), pgs 2416-2423, which is hereby incorporated by reference in its entirety.

Anchoring Nucleic Acids

In some embodiments, the methods described herein comprise trapping the nucleic acid molecule in the nanopore without using hairpin structures. In some embodiments, the nucleic acid molecule is anchored to the membrane to trap the nucleic acid molecule in the nanopore (e.g., to prevent the nucleic acid from passing completely through the nanopore).

The present disclosure provides a method for nucleic acid sequencing, comprising: (a) anchoring a nucleic acid molecule to a membrane having a nanopore therein; (b) threading the nucleic acid molecule or a portion thereof through or in proximity to the nanopore; (c) sensing one or more individual bases of the nucleic acid molecule during step (b); and (d) optionally reversing the direction of threading, where anchoring the nucleic acid molecule to the membrane prevents the nucleic acid molecule from threading completely through the nanopore.

Figure 5:
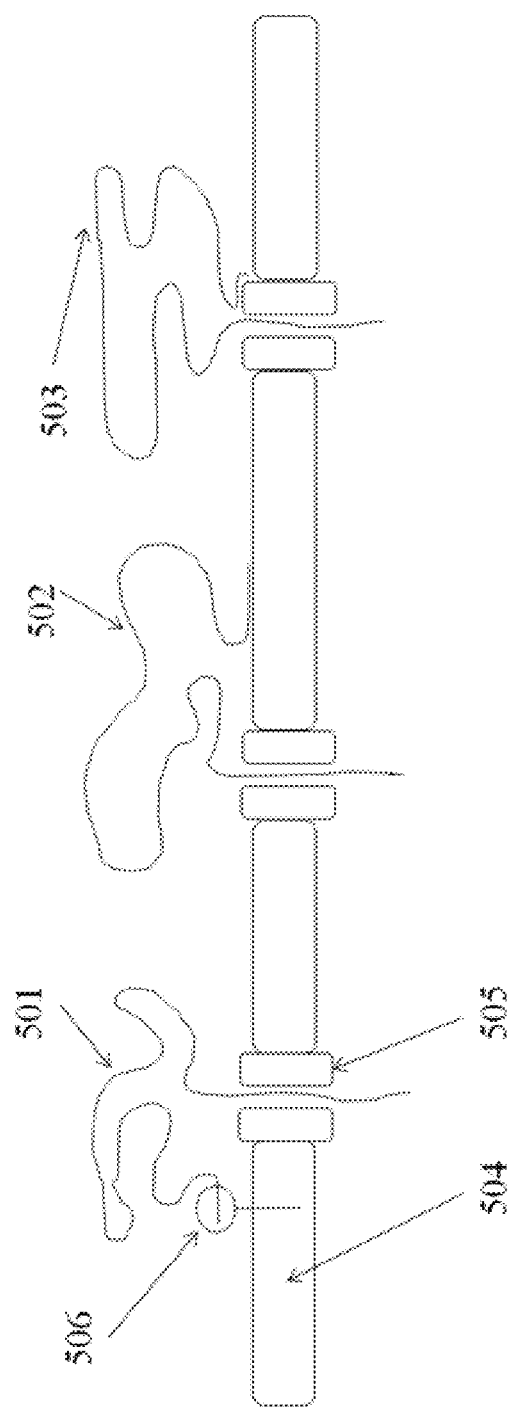
FIG. 5 shows examples of a nucleic acid molecule anchored to a membrane.

Referring to FIG. 5, nucleic acid molecules 501, 502 and 503 are anchored to a membrane 504. In some embodiments, the membrane comprises one or more nanopores 505. Alpha hemolysin is an example nanopore. In some instances, the membrane is a lipid bilayer.

In some embodiments, the membrane further comprises a nucleic acid binding protein 506 and the nucleic acid molecule 501 is anchored to the nucleic acid binding protein. In some embodiments, the nucleic acid binding protein comprises a trans-membrane that interact with (e.g., are embedded into) the membrane (e.g., a lipid bilayer). In some instances, trans-membrane domains comprise hydrophobic amino acids. Nucleic acid binding proteins are known in the art and include proteins that have specific (i.e., bind only some nucleic acid sequences) or general (i.e., bind many or all nucleic acid sequences) affinity for either single or double stranded nucleic acid molecules. Examples include transcription factors, polymerases, nucleases, leucine zippers, among others. In some instances, the nucleic acid binding protein is a fusion protein comprising a trans-membrane domain.

In some embodiments, the nucleic acid molecule 502 is anchored directly to the membrane (e.g., without a nucleic acid binding protein). The membrane can be modified or derivatized to form covalent or non-covalent bonds with the nucleic acid molecule. In some instances, the nucleic acid molecule 502 is modified or derivatized to form covalent or non-covalent bonds with the membrane. The nucleic acid molecule 503 can be anchored to the nanopore. The attachment between the nucleic acid molecule and the nanopore can be covalent or non-covalent. In some instances, the nanopore is a fusion between a nanopore protein (e.g., alpha hemolysin) and a nucleic acid binding protein.

Method for Manipulating Lipids on a Surface

The present disclosure provides methods for manipulating membrane subunits, such as lipids, on a surface. Such manipulation can aid in the formation of a membrane as part of a nanopore detector.

Figure 6:
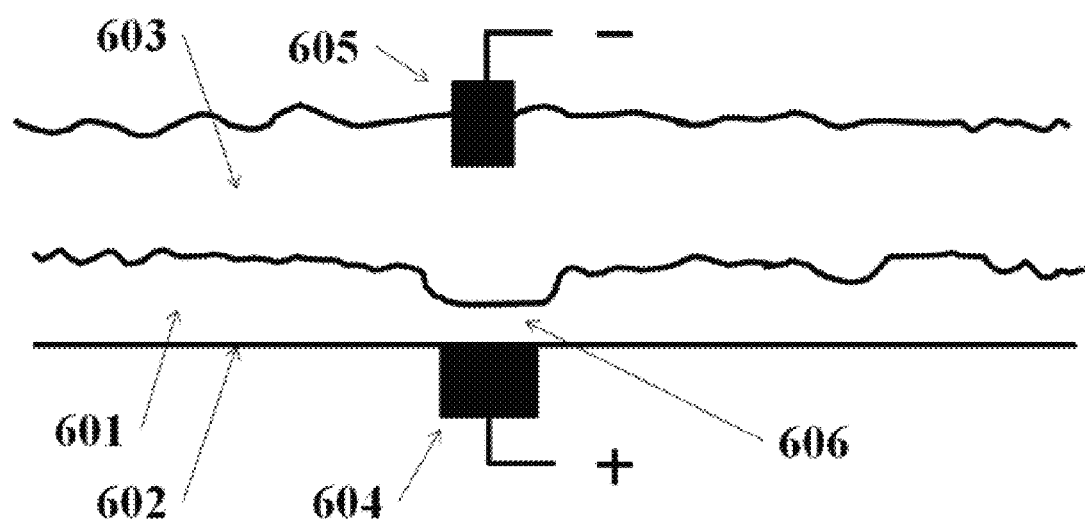
FIG. 6 shows an example of a fluid comprising an ionic phase and a hydrophobic phase in contact with a surface comprising a sensor.

With reference to FIG. 6, a hydrophobic phase 601 (e.g., diphytanoylphosphatidyl-choline (DPhPC) in decane at 15 mg/mL) deposits onto a surface 602 (e.g., a planar hydrophobic surface). In some instances, when a hydrophilic phase is added 603, all or most of the hydrophobic phase forms a pool on the surface. The hydrophilic phase may comprise an electrolyte (e.g., a salt such as KCl) and/or a redox active molecule (e.g., ferrocene carboxylate where the molecule is capable of cycling between the $Fe^{+2}$ and $Fe^{+3}$ redox states). In some cases, electrodes on the surface 604 are sealed under these pools of hydrophobic phase and are not in direct contact with the hydrophilic phase. The sealed electrodes do not generally complete an electrical circuit with a reference electrode 605 in contact with the hydrophilic phase. In some instances, the electrodes remain sealed and do not conduct even when an electrical potential is applied to the electrode. In some cases, applying a voltage to the electrodes thins the hydrophobic phase above the electrode and the hydrophobic phase is pushed to the sides of the electrode 606. In some cases, the hydrophilic phase displaces a portion of the hydrophobic phase in the vicinity of the electrode, thereby thinning the hydrophobic phase in relation to the ionic phase in proximity to the electrode.

Figure 7:
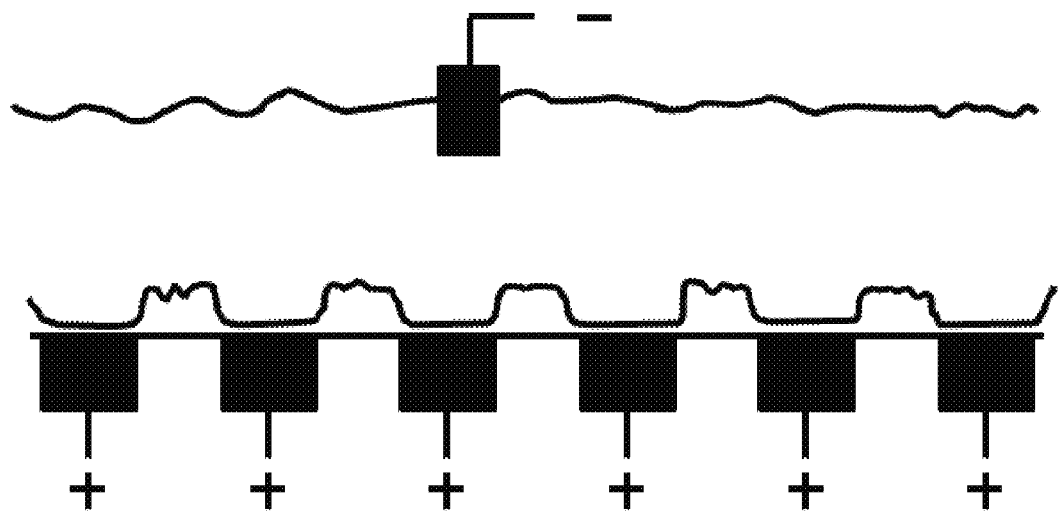
FIG. 7 shows an example of a fluid comprising an ionic phase and a hydrophobic phase in contact with a surface comprising a plurality of sensors.
Figure 8:
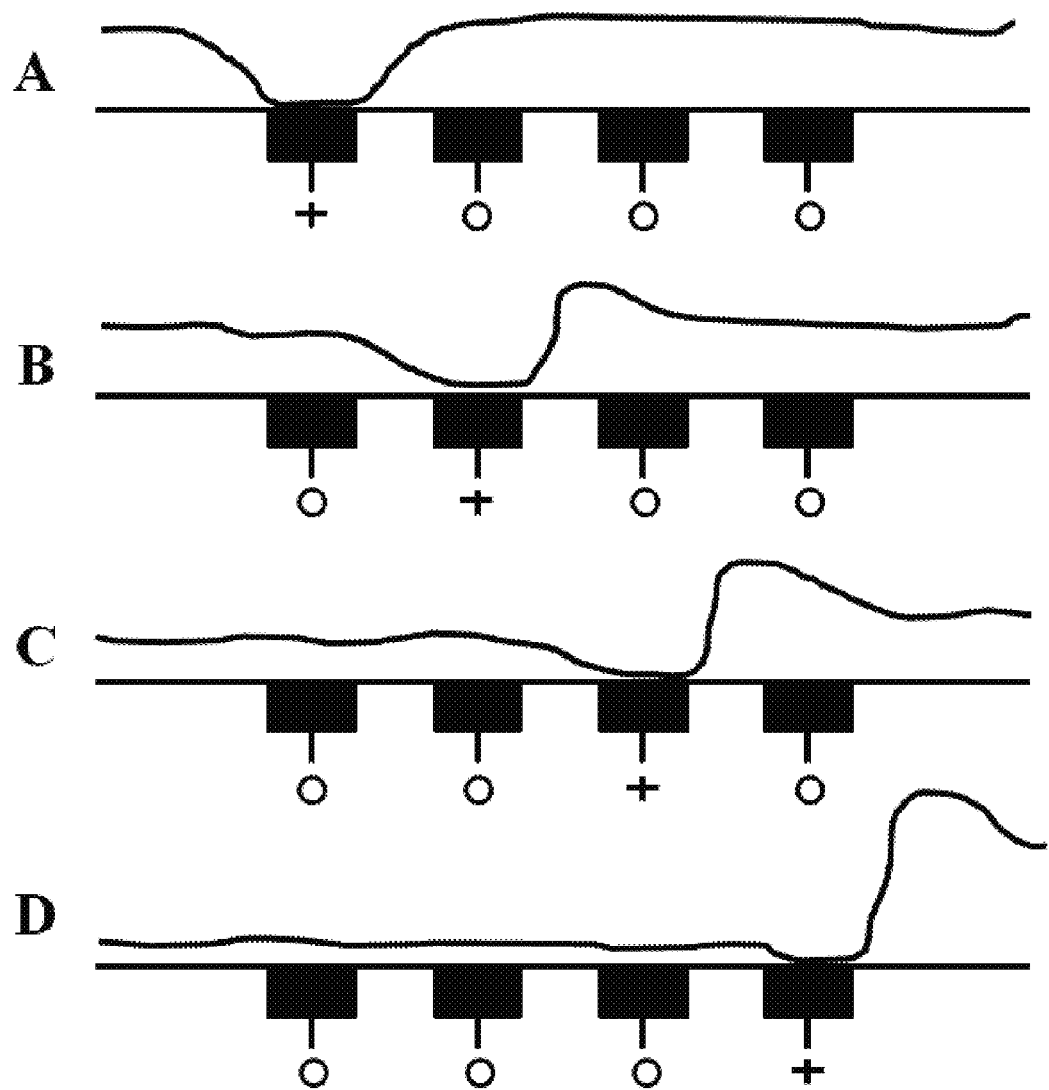
FIG. 8 shows an example of thinning of a hydrophobic phase by energizing a plurality of electrodes in a spatial and/or temporal pattern.

FIG. 7 depicts a volume of fluid comprising an ionic phase and a hydrophobic phase where the hydrophobic phase thins out in the regions above a plurality of electrodes. As shown in FIG. 8, in some embodiments, a plurality of electrodes are energized in a spatial and/or temporal (i.e., time series) pattern to move the hydrophobic phase across the surface.

In another aspect, provided herein is a method for manipulating a fluid on a surface, the method comprising: (a) providing a surface, an array of electrodes in proximity to the surface, and a fluid comprising an ionic phase and a hydrophobic phase, where the hydrophobic phase is adjacent to the surface; and (b) energizing the electrodes in a spatial and/or temporal pattern, thereby decreasing a volume of the hydrophobic phase in relation to the ionic phase in proximity to the electrodes. In some embodiments, energizing the electrodes in (b) effects a thinning of the hydrophobic phase in contact with the surface For example, as shown in FIG. 8, a series of electrodes are energized in sequence such that a wave of the hydrophobic phase is moved across the surface. A thinning depression in the hydrophobic phase is created above the first positively charged electrode in FIG. 8A. In some embodiments, the charge on the first electrode is then set to neutral and a second electrode is positively charged (FIG. 8B). In some cases, this pushes a leading wave of hydrophobic phase in the direction away from the first electrode (to the right in FIG. 8) and thins out the hydrophobic phase in the direction toward the first electrode (to the left in FIG. 8). FIGS. 8C and 8D show that the wave can be further moved across subsequent electrodes, further pushing the leading wave and further thinning the hydrophobic phase in the trailing direction.

In some embodiments, the electrodes are closely spaced. The space between the electrodes is any suitable distance (e.g., a distance suitable for forming a wave). In some instances, the distance between the electrodes is less than the width of the electrodes. In some instances, the distance between the electrodes is about the same as the width of the electrodes. In some instances, the distance between the electrodes is about twice, about three times, about 4 times, about 5 times, about 6 times, about 7 times, about 8 times, about 9 times, or about 10 times the width of the electrodes.

In some instances, the electrodes are individually controllable and/or individually addressable. As used herein for example, one is able to determine a state of a controllable electrode and one is able to take measurement signals from an addressable electrode. One is able to set the voltage and/or choose between voltage states (i.e., neutral or charged) for each electrode in an array of individually controllable electrodes. In some instances, groups of electrodes comprising an array of electrodes are separately controllable from other groups of electrodes. In some embodiments, the electrodes are further capable of sensing (e.g., sensing current changes associated with the passage of a nucleic acid molecule through a nanopore).

Figure 9:
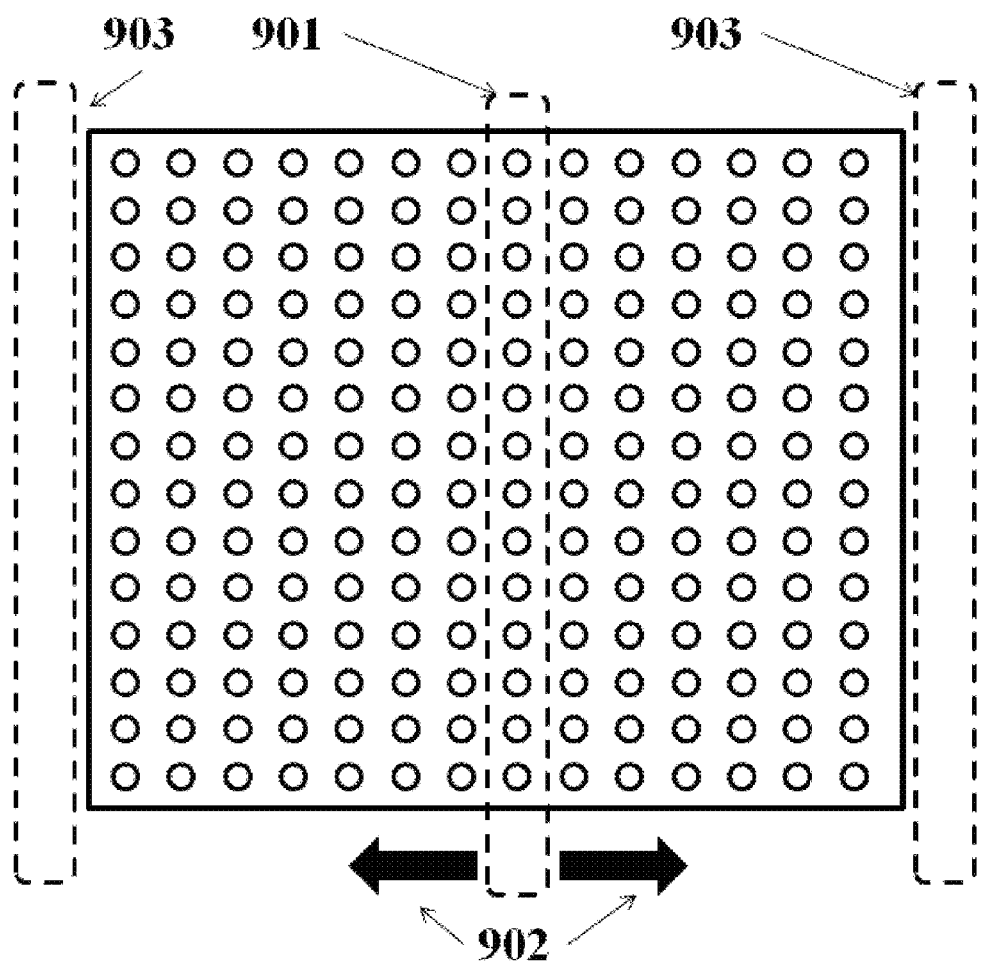
FIG. 9 shows an example of a top view of an array of electrodes, wherein groups of electrodes are energized in a spatial and/or temporal pattern to move a fluid to the edges of a surface.
Figure 10:
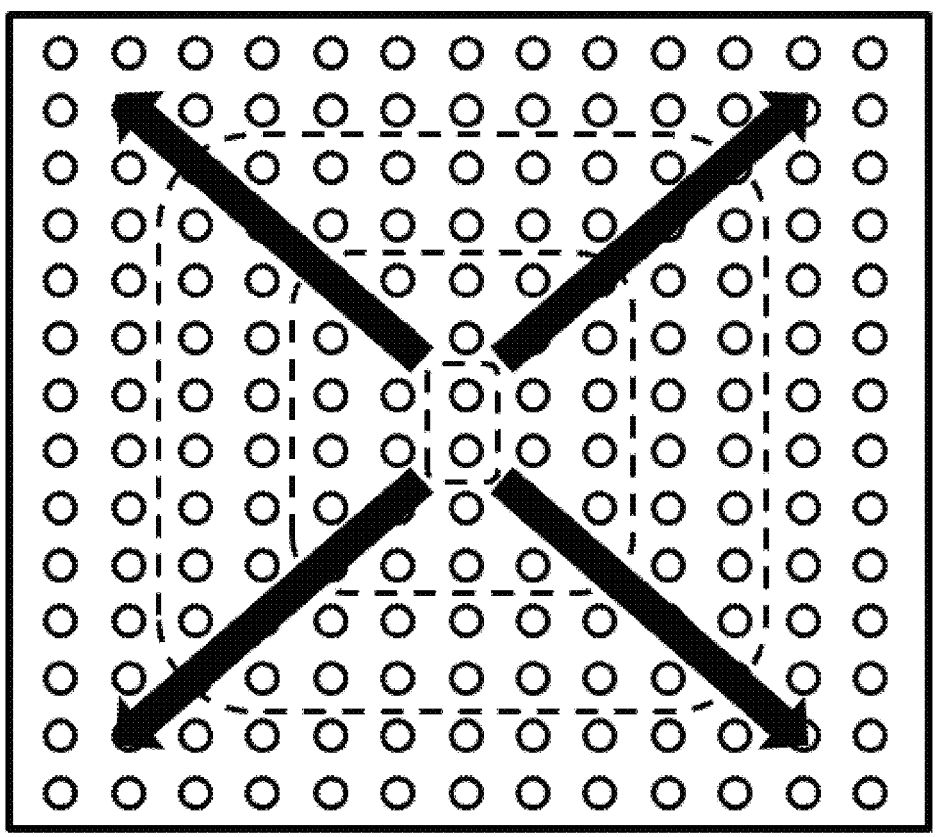
FIG. 10 shows an example of a top view of an array of electrodes where fluid is moved as described herein.

In some embodiments, the hydrophobic phase can be redistributed across the surface. With reference to FIG. 9, in an example, a first group of electrodes 901 are initially positively charged. Subsequently, electrodes in a second group adjacent to the first group of electrodes are positively charged, followed by those in a third group and so on 902 until a volume of the hydrophobic phase is moved to the periphery of the surface 903. The lipid phase can be moved in any direction (e.g., FIG. 10).

Figure 11:
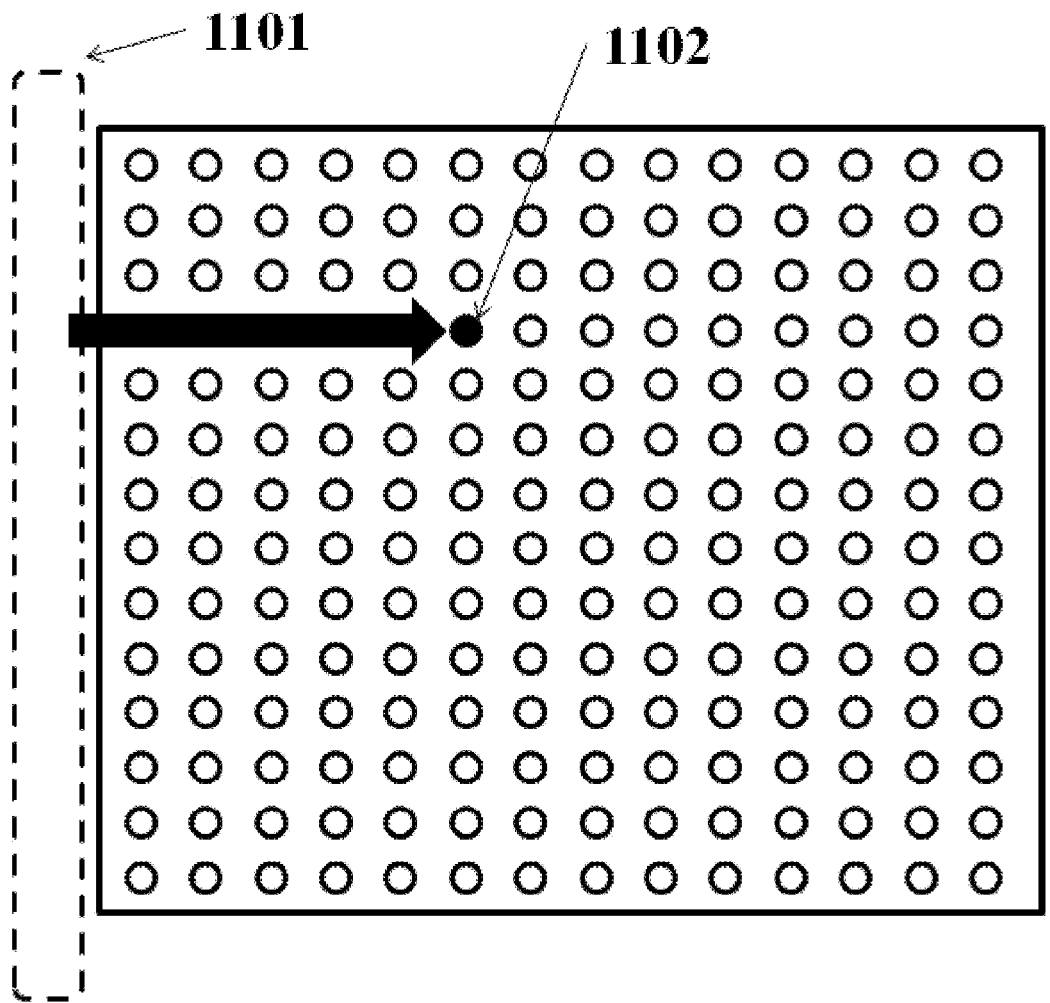
FIG. 11 shows an example of the methods described herein being used to draw fluid from the periphery of a surface and direct it to a position on the surface.

In some instances, the method draws hydrophobic phase from the periphery of the surface. For example, as shown in FIG. 11, the method is capable of retrieving hydrophobic phase from the periphery of the surface 1101 and directing it to an appropriate location on the surface 1102. In some instances, nucleic acid molecules are sequenced on the surface. In some cases, the surface comprises nanopores suitable for nucleic acid sequencing. In some cases, the method further comprises sequencing a nucleic acid molecule with the aid of nanopores on the surface. In some instances, the method directs the hydrophobic phase on the surface such that nucleic acid molecules are capable of being sequenced at the location on the surface (e.g., by reforming a lipid bilayer).

In some embodiments, the hydrophobic phase comprises lipid. In some examples, the lipid is DPhPC. In some instances, the lipid is solubilized in an organic solvent (e.g., decane). The concentration of lipid in the solvent can be any suitable value, including about 1 mg/mL, about 5 mg/mL, about 10 mg/mL, about 15 mg/mL, about 20 mg/mL, about 25 mg/mL, about 50 mg/mL, about 100 mg/mL, and the like. In some embodiments, the hydrophobic phase comprises a lipid that is thinned to form a bilayer on the surface.

In some embodiments, method redistributes lipid across the surface. In various instances, the surface is hydrophobic, essentially (or substantially) planar (e.g., a perfectly flat plane, or a surface having a certain amount of variation from an idealized plane), or both hydrophobic and essentially planar.

Stimulus-Assisted Flow Through Nanopore

The present disclosure provides stimulus-assisted methods for sequencing a nucleic acid sample using a nanopore. In some example, a nucleic acid sample can be sequenced without the aid or use of a molecular motor (e.g., enzyme). In some embodiments, the flow of the nucleic acid sample though the nanopore is facilitated by a series of electrical pulses.

Molecular motors are biological molecular machines that are agents of movement in living organisms. In general terms, a motor may be defined as a device that consumes energy in one form and converts it into motion or mechanical work; for example, many protein-based molecular motors harness the chemical free energy released by the hydrolysis of ATP in order to perform mechanical work. In some embodiments, the method does not use a nucleic acid motor. Examples of nucleic acid motors include RNA polymerase, DNA polymerase, helicases, topoisomerases, proteins that remodel chromatin, proteins that condense chromosomes, viral nucleic packaging motors, and the like.

In an aspect, described herein is a method for sequencing a nucleic acid sample, comprising: (a) facilitating, without the use of a molecular motor, the flow of the nucleic acid sample through a nanopore embedded in a membrane; and (b) detecting one or more nucleic acid subunits of the nucleic acid sample upon the flow of the nucleic sample through the nanopore.

The nucleic acid sample is sequenced with any suitable accuracy. In some embodiments, the nucleic acid is sequenced with an accuracy of at least 90%. In some embodiments, the nucleic acid is sequenced with an accuracy of at least 95%. In some embodiments, the nucleic acid is sequenced with an accuracy of at least 99%.

In some embodiments, the flow of the nucleic acid sample through a nanopore is facilitated by a series of electrical pulses. In some embodiments, the series of electrical pulses have a voltage between about 10 mV and 1000 mV, or 100 mV and 500 mV, or 200 mV and 400 mV. In some embodiments, the series of electrical pulses comprise an asymmetric reverse "V" time profile progression. Suitable electrical pulses are described below.

The operating voltages for operation (e.g., electrical pulses) of the chip may be at least partially determined by the salt concentration. In general, higher salt concentration results in higher current for the same applied voltage. In some embodiments, a +/−320 mV range is used for a salt concentration (e.g., KCl) of approximately 1 M. If the salt concentration is about 0.3 M the working voltages may be about +/−500 mV. The particular voltage and salt concentrations described herein are illustrative and not limiting.

Enzyme-Less Sequencing with Nanopore

Described herein are methods for sequencing a nucleic acid sample using a nanopore without the aid of an enzyme. Such methods may be used to sequence a nucleic acid without the use of sequencing by synthesis (SBS) methods. In some embodiments, methods for sequencing a nucleic acid molecule do not use a nucleic acid polymerase (e.g., RNA polymerase and/or DNA polymerase).

Described herein is a method for sequencing a nucleic acid sample, comprising sensing, with the aid of a sensing circuit adjacent to a nanopore, individual nucleic acid bases of the nucleic acid sample upon the flow of the nucleic acid sample or a portion thereof through the nanopore without the aid of an enzyme.

The nucleic acid sample is sequenced with any suitable accuracy. In some embodiments, the nucleic acid is sequenced with an accuracy of at least about 50%, 60%, 70%, 80%, 90%, 95%, 96%, 97%, 98%, 99%, 99.5%, or 99.9%, when identifying up to 5, 4, 3, 2, or 1 nucleic acid bases.

Described are example methods, devices and systems that are suitable for (a) providing the functional membranes as described here, (b) providing the device for use in molecular sensing as described here, (c) performing the method for sequencing a nucleic acid molecule by stimulus-assisted flow through a nanopore as described here, and/or (d) performing the method for enzymeless sequencing as described here.

Use of Nucleic Acid Binding Proteins

In some cases, the nucleic acid binding protein is free-floating and not anchored to the membrane as depicted in FIG. 5. The nucleic acid molecule may wrap around the nucleic acid binding protein. The nucleic acid molecule unwinds from the nucleic acid binding protein as it is pulled through a nanopore in some instances. The interaction between the nucleic acid and the nucleic acid binding protein may slow the rate of passage of the nucleic acid through the nanopore and increase the accuracy of nucleic acid sequencing. In some embodiments, electrical stimuli (e.g., high frequency pulses in some cases) are used to unwind the nucleic acid from the binding protein in a step-wise manner (i.e., at a rate suitable for sequencing the nucleic acid molecule).

Rolling Circle Nanopore Sequencing

Described herein is a method for nucleic acid sequencing where a single stranded nucleic acid is threaded through a nanopore while repeat units of nucleic acid sequence are extended onto the nucleic acid strand (e.g., by using a circular nucleic acid as a template). In some instances, the method is highly accurate (e.g., accuracy of at least about 90%, 91%, 92%, 93%, 94%, 95%, or 99%). In rolling circle sequencing, a nucleic acid molecule can be sequenced and re-sequenced multiple times to generate redundant nucleic acid sequence information. In some embodiments, the nucleic acid molecule is sequenced until the entire repeat unit is accurately determined (e.g., by sequencing the repeat unit a plurality of times). In some instances, the rate of extension at least partially determines the rate at which the nucleic acid is sequenced.

Another aspect of the invention provides a method for sequencing a nucleic acid, the method comprising (a) threading a single stranded nucleic acid molecule through a nanopore from a first end of the single stranded nucleic acid molecule and (b) extending the single stranded nucleic acid molecule from a second end of the single stranded nucleic acid molecule using a circular nucleic acid molecule as a template.

In some embodiments, the single stranded nucleic acid molecule is sequenced in the nanopore. In some embodiments, byproducts of nucleotide incorporation events (e.g., release of tags from tagged nucleotides upon nucleotides being incorporated into a growing chain by a polymerase) are sensed (e.g., by a nanopore) to determine the sequence.

Figure 12:
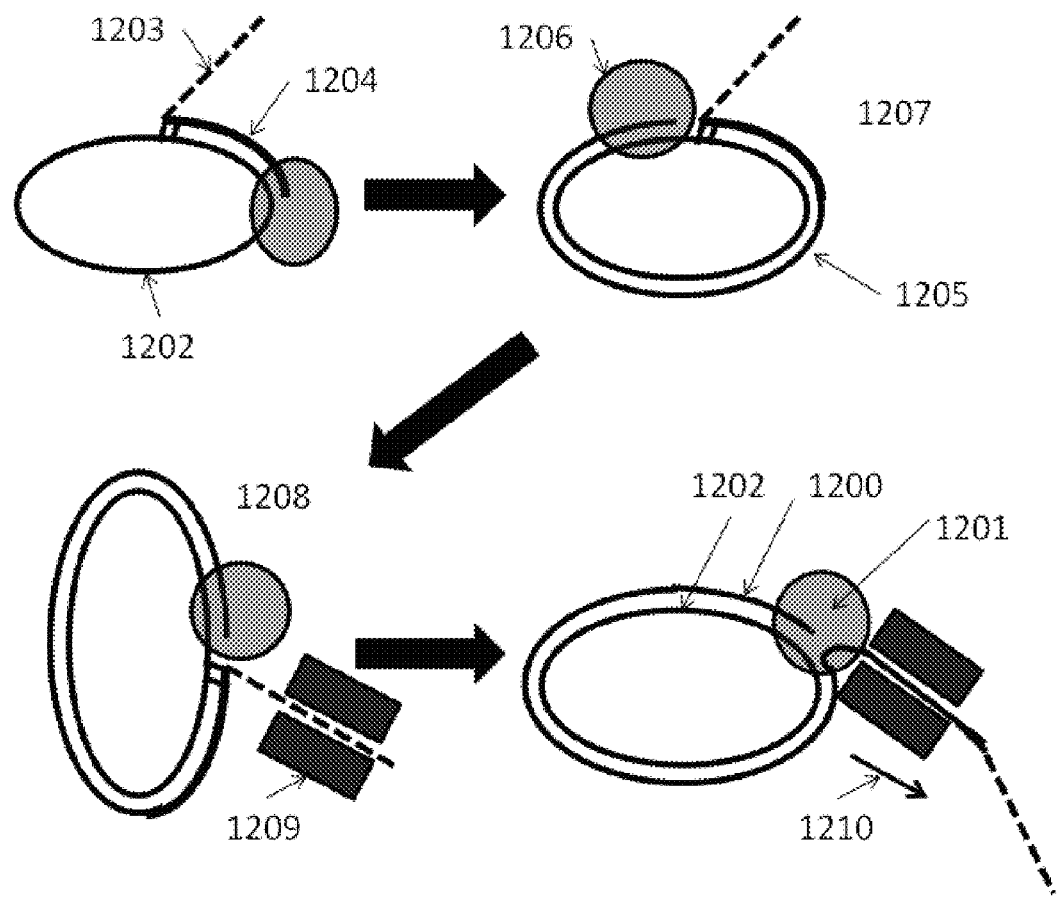
FIG. 12 illustrates an example method of nucleic acid sequencing using a nanopore.

With continued reference to FIG. 12, in some embodiments, the nucleic acid molecule 1200 is extended using an enzyme 1201 and a circular nucleic acid molecule 1202 as a template. In some embodiments, the speed of the enzyme (e.g., nucleic acid polymerase) at least partially determines the speed at which the single stranded nucleic acid molecule threads through the nanopore.

The method is performed in any one of a number of ways, examples of which are described here. In some embodiments, a first single-stranded nucleic acid molecule is circularized 1202. The nucleic acid is circularized by ligation in some instances. In some instances, a primer annealing sequence is inserted into the first single stranded nucleic acid molecule when it is circularized. In some instances, the primer annealing sequence is identical or nearly identical in all molecules to be sequenced. In some instances, the primer annealing sequence is different, and optionally used to identify from which sample a particular nucleic acid molecule originated. In some instances, the circular nucleic acid molecule is constructed from double stranded sample DNA or RNA. In one embodiments, the ends of the sense and antisense strands of a double stranded sample are ligated together (e.g., with linkers) such that the resulting circular nucleic acid comprises the sense and antisense strand, optionally comprising linkers and/or a primer binding site. In some embodiments, a hairpin is ligated onto an end (e.g., 3' end) of a single stranded nucleic acid molecule and an antisense strand is synthesized that is complimentary to the single stranded template. Following synthesis of the antisense strand, circularization is completed by ligation (e.g., blunt end ligation) of a loop of nucleic acid (e.g., DNA). In some embodiments, the sense strand comprises nucleic acid analogs.

In some instances, circular single stranded template molecules 1202 comprising both a sense and antisense strand are advantageous because (a) sequencing both the sense and anti-sense strand at a genomic position increases the accuracy of base calling, (b) allows for identification of mismatched bases, and (c) allows for positional double checking of reads.

Following circularization, a primer is annealed to the circularized molecule in some instances. In some embodiments, the primer comprises a nanopore capture region 1203 and a hybridization region 1204, where the hybridization region anneals to the circularized molecule. The capture region extending from the primer can be constructed of any molecule including abasic nucleic acids, PEG molecules, or any other of a variety of man-made polymers that are optimized to be captured into a nanopore. The capture region may be highly negatively or positively charged for example depending on the particular nanopore set-up or the type of sample being processed. The charge status of the capture region can also affect the electrophoretic pulling force exerted by an electrical potential. In some embodiments, optimization of this charge may improve the removal of a blocker molecule (e.g., blocking the procession of a polymerase). The composition of the capture region of the primer can be selected to give a unique signal that can designate the sample pool from which the sample originated. Multiple samples, each with their own identifier or capture region barcode, can be included in the same nanopore sequencing run. In some embodiments, the use of speed bumps is used to decode the capture thread.

In some instances, the primer comprises a pool of oligonucleotides all with a common nanopore capture region. In some instances, the nanopore capture region is ligated onto an oligonucleotide. In some embodiments, the sequence of the nanopore capture region indicates the sample from which the first nucleic acid molecule originated.

Following primer annealing, in some instances, the primer is extended from the end of the hybridization region using the first nucleic acid molecule as a template to create a second nucleic acid molecule 1205 (e.g., base paired to the first nucleic acid molecule). In some instances, the extension is performed by an enzyme (e.g., DNA polymerase, phi29 polymerase). In some embodiments, extension proceeds until the enzyme is blocked by the primer 1206. At this point, a stalled complex 1207 comprising an enzyme, a nanopore capture region and a circular double stranded nucleic acid molecule is formed in some instances.

In some embodiments, the formation of the stalled complex 1207 has certain advantages. In some embodiments, the nucleic acid comprising the stalled complex is less likely to form 3D structures or bind to itself or other nucleic acid molecules than may be the case without the formation of stalled complexes. In some embodiments, the formation of stalled complexes makes it more likely that all or substantially all of the nucleic acid molecules will be sequenced. In some embodiments, the formation of stalled complexes improves the efficiency of capture of the nanopore capture region by the nanopore.

Following formation of stalled complexes, in some instances, the stalled complexes 1208 are inserted into a nanopore 1209. In some embodiments, the nanopore capture region of the second nucleic acid molecule is inserted into a nanopore. The insertion can be performed in any suitable manner. In some instances, an electrical field is used to insert the nanopore capture region of the second nucleic acid molecule into a nanopore.

Following insertion of stalled complexes, in some instances, the second nucleic acid molecule is passed through the nanopore 1210. In some embodiments, the second nucleic acid molecule is passed through the nanopore while further extending the second nucleic acid molecule using the first nucleic acid molecule as a template. In some embodiments, the second nucleic acid molecule is sequenced as it passes through the nanopore.

In some embodiments, the nucleic acid sequence of the first nucleic acid molecule is determined by passing the second nucleic acid molecule through the nanopore until the sequence of the repeat unit is accurately determined. The accuracy is any suitable level, including any level of accuracy described herein, such 99.99%. In some embodiments, the second nucleic acid molecule comprises repeat units complimentary to the sequence of the first nucleic acid molecule Any suitable number of copies of the repeat unit are sequenced. In some embodiments, 1, 2, 3, 4, 5, 6, 7, 8, 9, 10, about 12, about 14, about 16, about 18, about 20, about 25, about 30, about 40, or about 50 copies of the repeat unit are sequenced.

In some instances, the primer performs several roles. With reference to FIG. 12, in some embodiments, the primer (i) primes synthesis 1204; (ii) blocks the progression of a nucleic acid polymerase 1206; and (iii) is inserted into the nanopore 1209. In some embodiments, having the primer perform several roles simplifies the chemistry and makes the method more robust and/or inexpensive.

In some embodiments, the composition of the primer is matched to the primer binding site so that the primer will preferentially bind to only the primer binding site. In some embodiments, synthetic nucleic acid analogs are used as part of the primer/primer-binding-site sequence (e.g., isodG and isodC).

In some embodiments, the nucleotide mix from which the polymerase draws nucleotides contains any natural or any synthetic nucleic acid analogs. In some embodiments, these analogs are selected to give a larger or a specific level of signal in the nanopore. In some embodiments, these analogs slow the transit of a nucleic acid strand through the nanopore (e.g., to make base reading easier). In some embodiments, the analogs allow for easier, more consistent threading into the pore.

Figure 13:
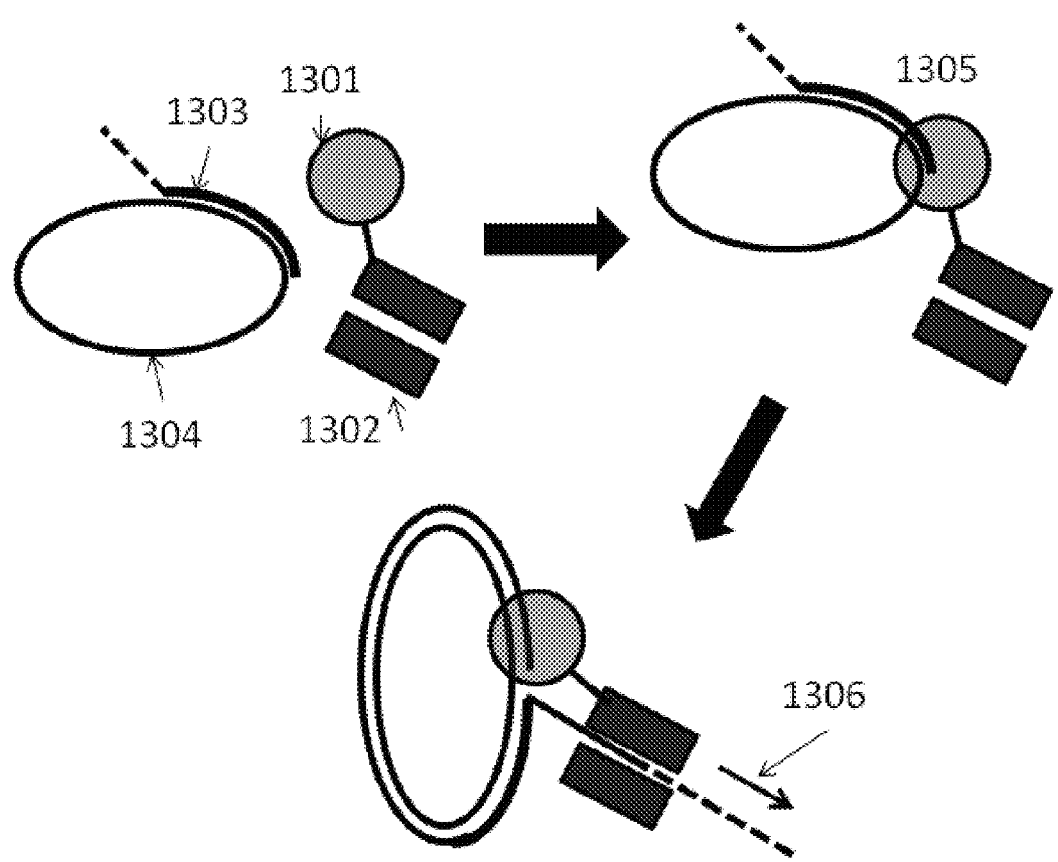
FIG. 13 shows an example method of nucleic acid sequencing using a circular nucleic acid molecule template.

Another embodiment of rolling circle nanopore sequencing is shown in FIG. 13. Here, a nucleic acid polymerase 1301 (e.g., DNA polymerase) is attached to a nanopore 1302. In some instances, the attachment is a disulfide bond or a fusion protein comprising the nanopore and the polymerase. The method also provides a circular nucleic acid molecule 1304 and a primer that at least partially anneals to the circular nucleic acid molecule 1303.

The method includes extending the primer from a first end 1305 using the nucleic acid polymerase and the circular nucleic acid molecule as a template. The extended primer can be passed through the nanopore 1306 from a second end while further extending the primer from the first end. The extended primer can be sequenced as it passes through the nanopore. In some embodiments, the primer is extended and passed through the nanopore until the sequence of the circular nucleic acid molecule is determined.

In some cases, the second end of the primer (dashed line) does not anneal to the circular nucleic acid molecule, but this is not required. At least part of the sequence of the primer may indicate the sample from which the circular nucleic acid originated.

Figure 14:
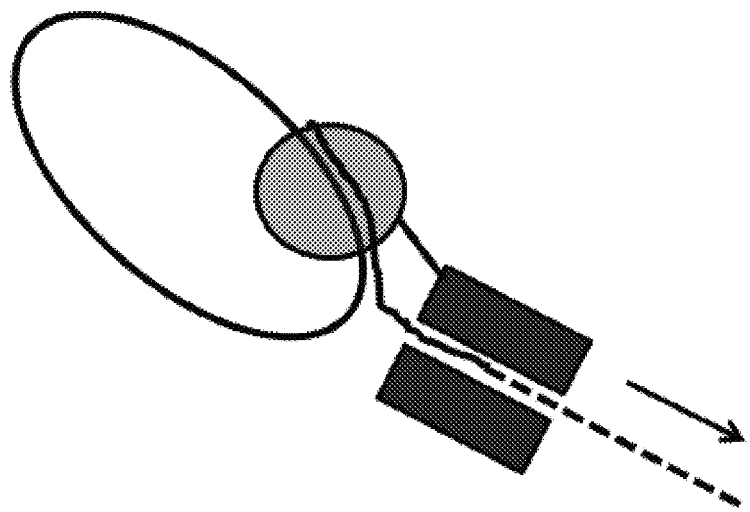
FIG. 14 shows another example method of nucleic acid sequencing using a circular nucleic acid molecule template.

Any suitable fraction of the extended primer can be annealed to the circular nucleic acid molecule. FIG. 13 shows an example where the circular nucleic acid molecule is mostly annealed to the extended primer. FIG. 14 shows an example where the circular nucleic acid molecule is mostly not annealed to the extended primer.

Locked Enzyme Unzipping

Figure 15:
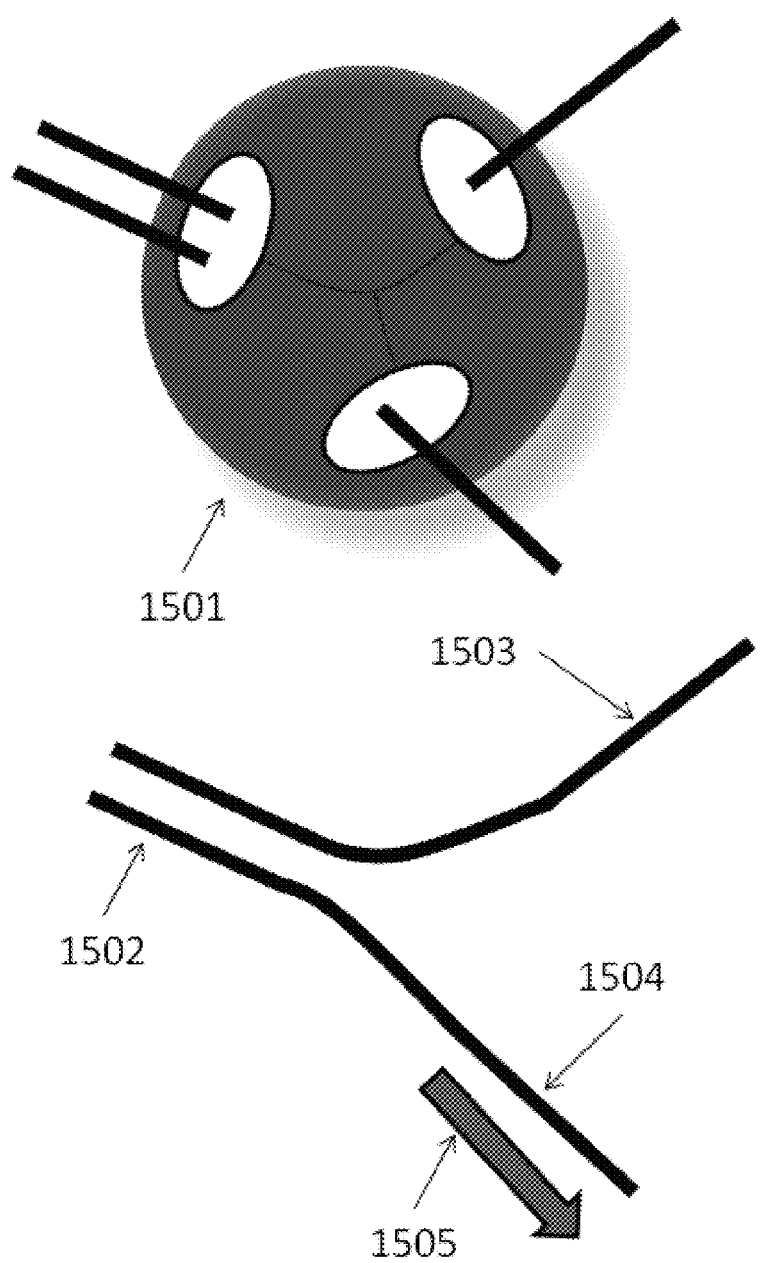
FIG. 15 illustrates an example method for unzipping a double stranded nucleic acid molecule.

Described herein are methods for unzipping double stranded nucleic acid and methods for nucleic acid sequencing. With reference to FIG. 15, in some instances, the method comprises (a) locking a protein 1501 around the junction formed by a segment of double stranded nucleic acid 1502 and the dissociated sense 1503 and anti-sense strands 1504 comprising the double stranded nucleic acid and (b) providing a pulling force 1505 on at least one of the sense and anti-sense strand.

Figure 16:
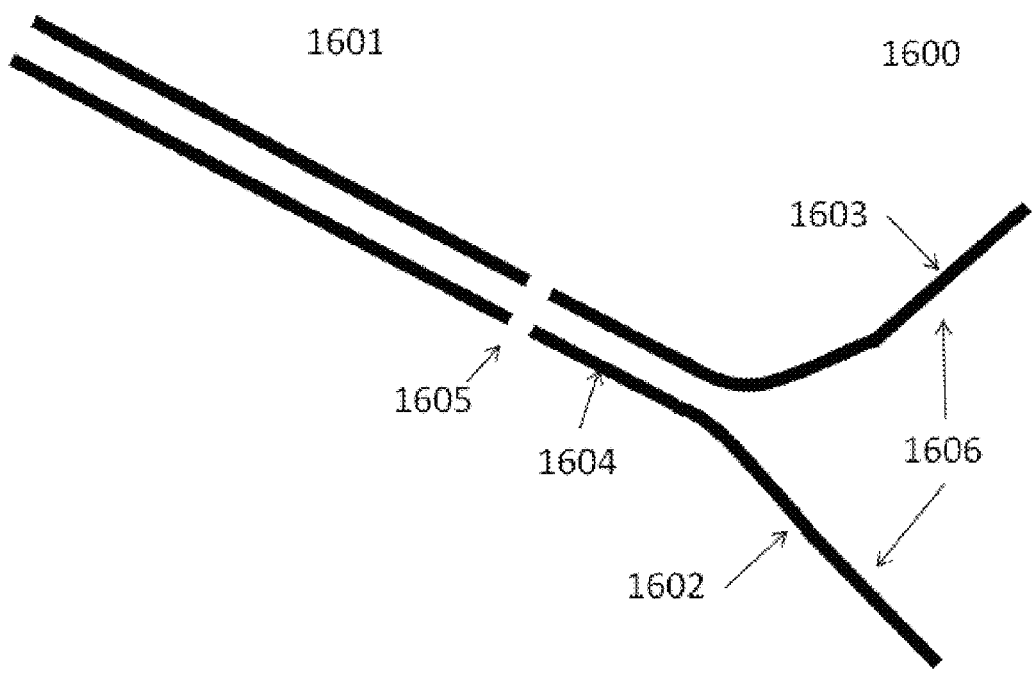
FIG. 16 illustrates an example step of a method for sequencing a nucleic acid molecule using a nanopore and a locked protein.
Figure 17:
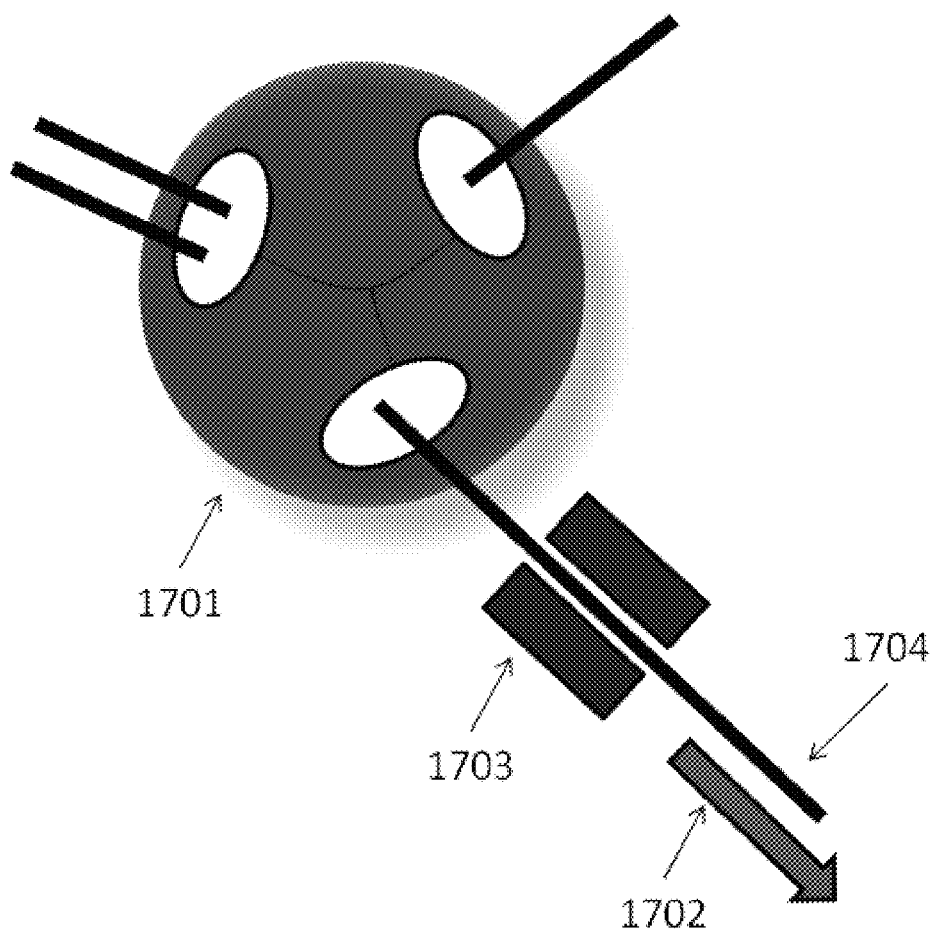
FIG. 17 illustrates a method for sequencing a nucleic acid molecule using a nanopore and a locked protein.

In another aspect, provided herein is a method for nucleic acid sequencing, the method comprising: with reference to FIG. 16, (a) ligating a duplex nucleic acid 1600 to an end of a double stranded nucleic acid 1601, where the duplex nucleic acid comprises a sense strand 1602 and an anti-sense strand 1603, where the sense strand and the anti-sense strand are base paired at the first end of the duplex nucleic acid 1604 and the first end is ligated to the double stranded nucleic acid 1605, and where the sense strand and the anti-sense strand are not base paired at the second end of the duplex nucleic acid 1606. The method further comprises, with reference to FIG. 17, (b) locking a protein 1701 around the junction where the sense strand and the anti-sense strand are base paired and where they are not base paired; (c) threading 1702 the sense strand or the anti-sense strand through a nanopore 1703, where the strand 1704 is sequenced with aid of the nanopore.

Figure 18:
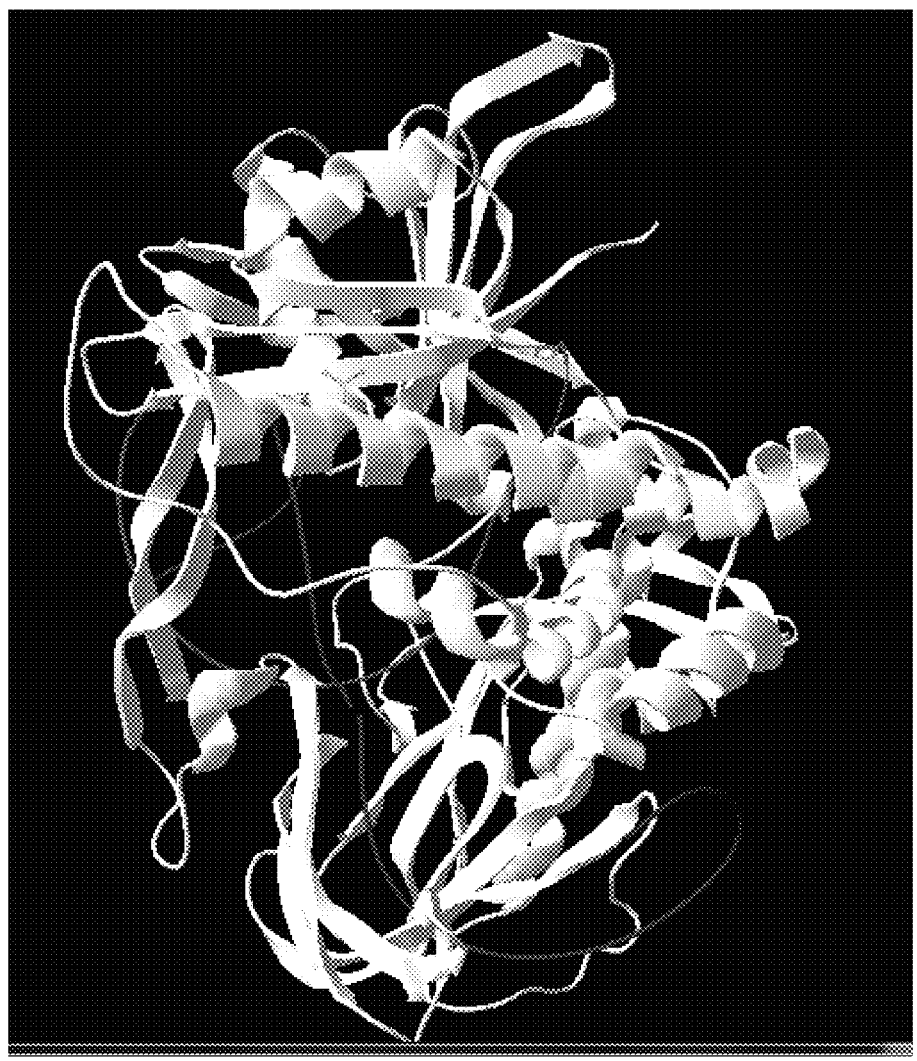
FIG. 18 shows a ribbon diagram of a phi29 polymerase.
Figure 19:
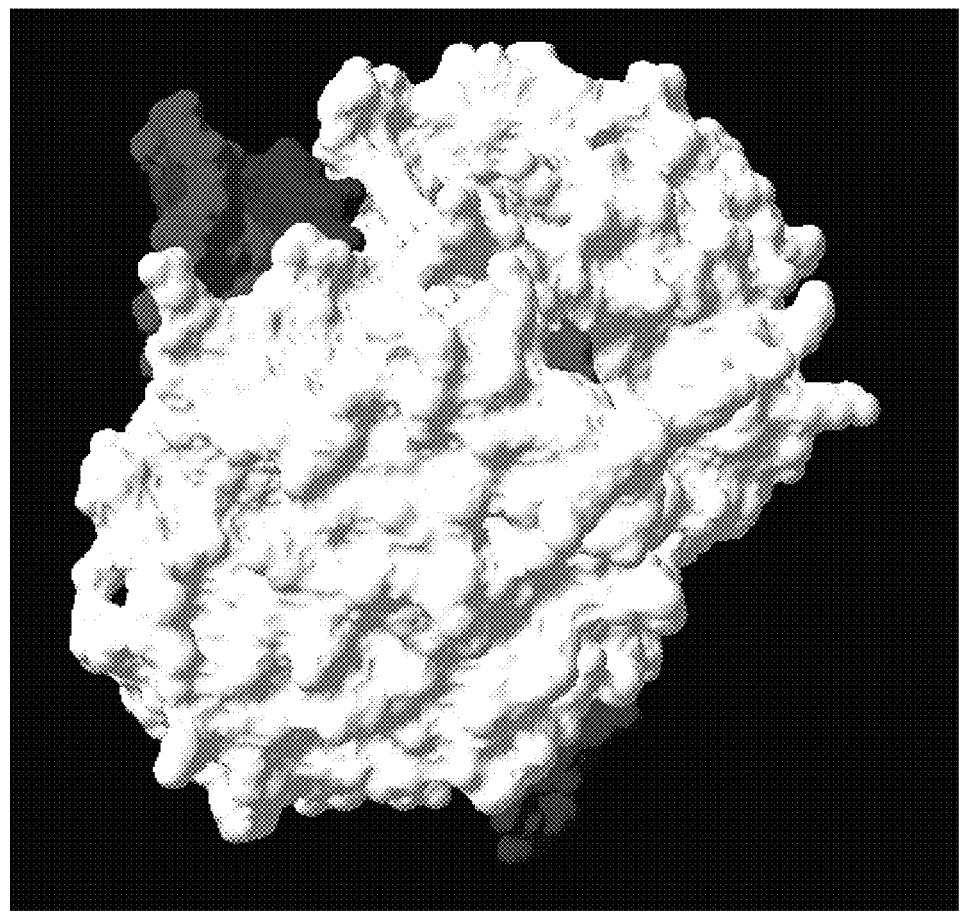
FIG. 19 shows a space filling diagram of a phi29 polymerase.

The protein can be any suitable protein. In some embodiments, the protein is phi29 polymerase. FIGS. 18 and 19 depict phi29 polymerase. In some embodiments, the polymerase is mutated to provide locations for the formation of cross-links suitable for locking the polymerase around the junction. In some embodiments, the mutations comprise substituting an amino acid for cysteine, where disulfide cross-links are formed between cysteine amino acids.

In some embodiments, the protein is locked by cross-linking the protein. Cross-links are formed between any suitable entities, optionally between amino acids comprising the protein. Another suitable method for locking the protein is to incorporate non-natural amino acids into the protein and form cross-links from the non-natural amino acid. The non-natural amino acid can have any suitable cross-linkable chemical group or adapter. Methods for incorporating non-natural amino acids into proteins are known and include the use of suppressible stop codons. In some instances, the cross-links are disulfide bonds. In some instances, the formation of cross-links is initiated by light (e.g., ultraviolet light). In some instances, formation of cross-links is initiated by light or chemical agents. Formaldehyde is one suitable chemical agent. Formaldehyde cross-links primary amino groups in proteins with other nearby nitrogen atoms through a $CH_2$— linkage.

In some embodiments, the locked protein unzips the double stranded nucleic acid. In some embodiments, the locked protein at least partially determines the rate at which the strand is threaded through the nanopore. In some instances, the rate is suitably slow to obtain highly accurate nucleic acid sequences. In some embodiments, the rate is suitably slow such that each nucleic acid position is sequenced with suitable accuracy (e.g., about 90%, about 95%, about 97%, about 99%, or about 99.5%) in a single pass.

Controlled Strand Passage with Biotinylated Nucleic Acids

Described herein are methods for at least partially reducing the rate at which a nucleic acid molecule passes through or passes in proximity to a nanopore. In some instances, the methods are used to increase the accuracy of nucleic acid sequencing using a nanopore and/or to determine the sequence of a nucleic acid molecule by sequencing it few times (e.g., a single time).

Figure 20:
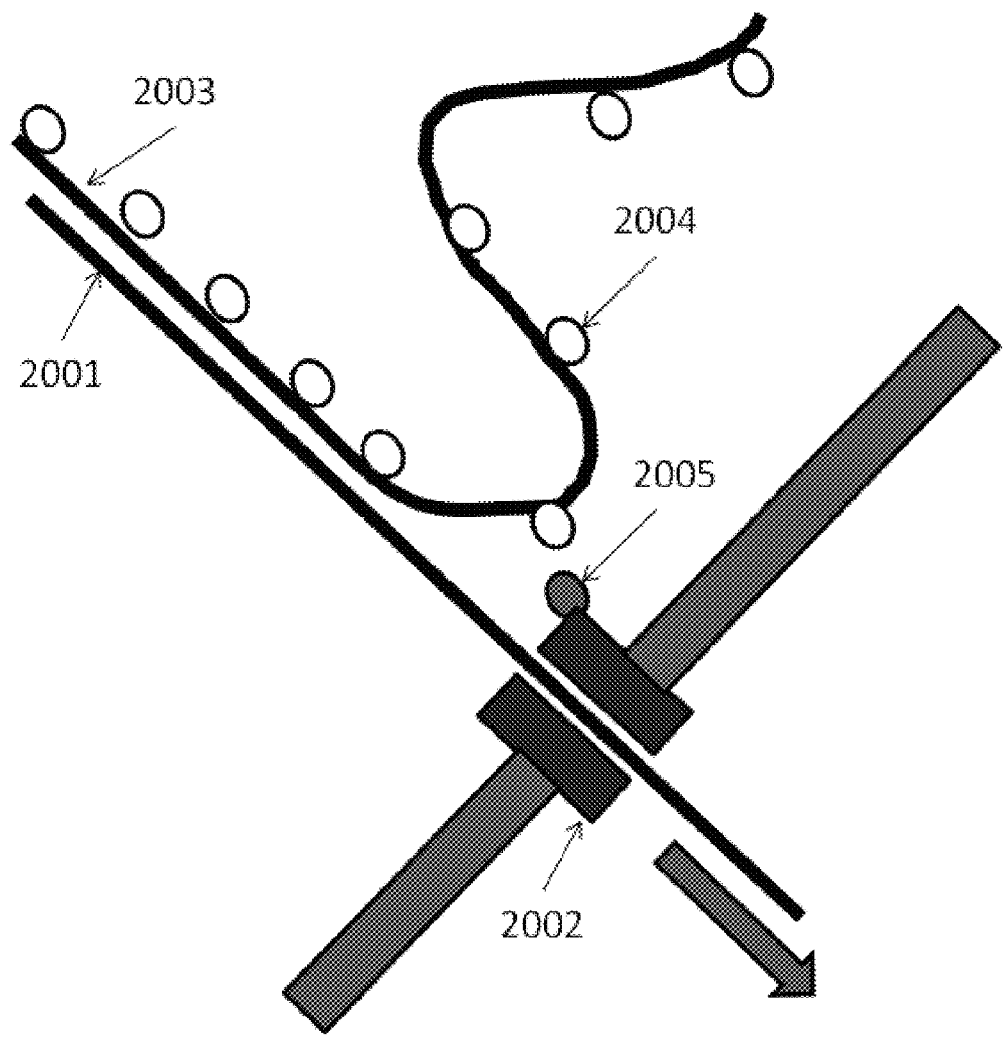
FIG. 20 shows an example method for sequencing a nucleic acid molecule using a nanopore, where the rate of passage through the nanopore is at least partially determined by interactions between binding partners.

With reference to FIG. 20, in another aspect, provided herein is a method for nucleic acid sequencing, the method comprising passing a first single stranded nucleic acid molecule 2001 through or in proximity to a nanopore 2002, where the first molecule is base paired with a second single stranded nucleic acid molecule 2003 comprising first binding molecules 2004, and where the first binding molecules interact with the nanopore or a second binding molecule attached to the nanopore 2005.

In some embodiments, the first nucleic acid molecule is sequenced with aid of the nanopore. In some instances, passage of the first single stranded nucleic acid molecule through the nanopore generates nucleotide-specific current blockages detectable as described herein.

In some embodiments, the rate at which the first nucleic acid molecule passes through or in proximity to the nanopore is at least partially determined by the interaction between the first and second binding molecules. In some embodiments, the interaction comprises the formation of non-covalent bonds between the first and second binding molecules.

The binding molecules are any two molecules capable of interacting (e.g., forming a non-covalent bond). In some embodiments, the first binding molecule is biotin and the second binding molecule is streptavidin or avidin.

System with Bar-Code

Devices and systems described herein can be configured for sensing a biological sample (e.g., blood, saliva, tissue) from a subject (e.g., an individual person). An example of sensing is sequencing genomic information and/or the genome of a subject. In some embodiments, each subject uses a unit (e.g., of the device or system described herein) that is dedicated to the subject. In some embodiments, the biological sample of each subject is sensed on a different unit than other subjects. In some embodiments, an identification member (e.g., bar code) is used to match the subject to a unit.

In some examples, a system for sensing a biological sample from a subject comprises (a) a housing; (b) a sensor within the housing, the sensor having an electrical circuit adjacent to a membrane with a nanopore therein, where the electrical circuit is adapted to generate an electrical signal in response to the biological sample flowing through or adjacent to the nanopore; and (c) an identification member on or within the housing, the identification member having a unique identifier associated with the system and adapted to aid in associating the electrical signal, or characteristic information derived from the electrical signal, with the subject.

The identification member is any device or component capable of being identified. In some embodiments, the identification member is selected from the group consisting of electrically erasable programmable read-only memory, a radiofrequency identification tag, flash memory, barcode and serial number. In some embodiments, the identification member is identified by sight. In some embodiments, the identification member is ready by a scanner, machine, or the like.

In some instances the housing is small. In some instances, the system is portable. In some embodiments, the housing has a volume of at most 27,000 $cm^3$. In some embodiments, the housing has a volume of at most 10,000 $cm^3$. In some embodiments, the housing has a volume of at most 5,000 $cm^3$. In some embodiments, the housing has a volume of at most 500 $cm^3$. In some instances the system is hand-held and/or capable of being carried by hand.

The identification member can be provided in or on the housing. The identification member can permit the subject to be anonymous, which may be preferable in instances in which anonymity is of concern. The identification member can link the a system or device (e.g., nanopore detector) to the subject.

The system is capable of sensing any suitable characteristic of the biological sample. In some embodiments, the system is capable of sequencing the genome of the individual in at most 10 hours. In some embodiments, the system is capable of sequencing the genome of the individual in at most 1 hour. In some embodiments, the system is capable of sequencing the genome of the individual in at most 10 minutes.

Membrane Protein Assays and Other Uses

Devices of the present disclosure can be used for any suitable purpose. In some cases, the devices are not used for nucleic acid sequencing. Without limitation, the devices can be used to detect single nucleotide polymorphisms (SNPs), genetic insertions, deletions or other genetic mutations or markers, protein sequencing, sequencing of any other polymer, and the like.

Methods of the present disclosure can be used to construct membranes that mimic biological membranes. In some embodiments, the composition of the membrane and/or membrane proteins comprising the membrane are substantially similar to the composition of a cellular membrane of an organism. In some instances, the membrane and/or membrane proteins comprising the membrane are substantially similar if they comprise similar types, identities, and/or proportions of membrane proteins and/or lipids. In some embodiments, the proportion of proteins comprising the membrane is within about 50%, within about 40%, within about 30%, within about 20%, within about 10%, or within about 5% of the proportion of proteins in a biological membrane.

Biological cells can have various membranes including a cellular membrane that encloses the cells and various membranes that enclose organelles (e.g., endoplasmic reticulum, nucleus, golgi apparatus, mitochondria, lysosome, peroxisome, vacuole). In some instances, the membrane comprises a lipid bilayer. The composition of lipids in the bilayer is variable depending on the species, the type of membrane, or even the developmental state of the organism or the environmental conditions surrounding the organism. Lipid bilayers often comprise two layers of phospholipids with the hydrophobic tails of the two layers facing each other. Any lipid or combination of lipids are suitable for forming the biological membrane mimics as described herein including for example phosphatidylcholine. In some embodiments, the membranes created according to the methods described here comprise sterols (e.g., cholesterol).

Biological membranes also generally comprise membrane proteins, but this is not required. Membrane proteins comprise a large fraction of the mass of a biological membrane in some instances (e.g., at least 20%, at least 30%, at least 40%, at least 50%, or at least 60%). In one aspect, the methods described herein are used to insert membrane proteins into a membrane.

There are many examples of membrane proteins. Membrane proteins include transporters, linkers, channels, receptors, enzymes, structural proteins, proteins involved in accumulation and transduction of energy, proteins responsible for cell adhesion, and the like. Some examples include alpha hemolysin, insulin receptor, integrins, cadherins, glycophorin, rhodopsin, among many others. Some membrane proteins are monomeric (comprise a single polypeptide chain) and some membrane proteins comprise a plurality of polypeptide chains (of one or more types).

An aspect of the present disclosure provides a method for performing a membrane protein assay, the method comprising: (a) applying an electrical stimulus to at least one membrane formed over an electrode such that a membrane protein is attracted to and inserted into the membrane; and (b) assaying a property of the membrane and/or the membrane protein.

Methods for forming membranes over electrodes are provided herein. Methods for applying an electrical stimulus suitable for attracting and inserting membrane proteins (e.g., alpha hemolysin) into a membrane are also provided above. In some embodiments, the membrane protein comprises a trans-membrane domain. Trans-membrane domains comprise hydrophobic amino acids (e.g., leucine, isoleucine, valine, phenylalanine, and tryptophan) in some instances. In some cases, the hydrophobic amino acids are contiguous. In some instances, the trans-membrane domains at least partially insert into the lipid bilayer. In some instances, the trans-membrane domains completely span the lipid bilayer. The membrane protein can have any number of trans-membrane domains (e.g., 1, 2, 3, 4, 5, 6, 7, 8, 9, 10, or more trans-membrane domains).

In some embodiments, a plurality of different membrane proteins are inserted into the membrane. In some embodiments, the plurality of different membrane proteins comprise mutants of a library of proteins. In some embodiments, the plurality of different membrane proteins comprise different types of membrane proteins (e.g., porins, adhesins, receptors, and the like). In some embodiments, membranes are formed over a plurality of conductive electrodes, a library of mutant membrane proteins are distributively inserted into the membranes over the plurality of electrodes, and the library of membrane proteins are assayed.

The assay can be different in various embodiments. In some embodiments, the assay is a test of function (e.g., the translocation rate of a porin or the specificity of a receptor). The assay uses any suitable reagents, times, temperatures, detection mechanisms (e.g., electronic detection, fluorescent detection), and the like. In some embodiments, the assay comprises determining the effect of drug compounds on the membrane and/or membrane protein. In some embodiments, the assay comprises determining the effect of a chemical compound on the membrane and/or membrane protein.

In some embodiments, membrane bound proteins and pores can be electrically attracted to and inserted into an artificial lipid bilayer membrane, or possibly other forms of membranes representing all known living and non-living species. In some instances, a lipid bilayer or other membrane that mimics the membrane of a living organism is first created over a conductive electrode. A potential can then be applied to the electrode such that membrane protein(s) floating free in solution above the artificial membranes are attracted to and inserted into the membrane. The insertion of these proteins can be detected by changes in electrical properties as measured by the electrode.

In one aspect, an intact membrane is detected versus a broken membrane. In some embodiments, the method further comprises detecting the insertion of the membrane protein by measuring the electrical properties of the electrode. The total conductivity and capacitance of a normal membrane with protein inserted can be detected. In some embodiments, the method further comprises measuring the total conductivity and/or capacitance with the electrode to determine one or more defects in the membrane.

In some embodiments, the membrane protein inserts one or more trans-membrane domains into the membrane. In some instances, the membrane protein does not form a pore when it is inserted into the membrane (e.g., so insertion thereof may not be detectable by a change in capacitance or conductivity of the membrane). A reporter moiety and/or label can be attached to the membrane protein in order to determine whether the protein has been inserted. The reporter moiety and/or label can be chemically or biologically reactive (e.g., can be a fusion protein of the membrane protein and a reporter enzyme, a biotinylated membrane protein, etc.). Following insertion of the protein, a reagent may be contacted with the membrane protein to generate a signal (i.e., optionally generated by an interaction between the reagent and the reporter moiety and/or label). Suitable signals include pH changes, electrical changes and/or capacitive changes (e.g., detectable by the sensor). In some instances, light is emitted (e.g., fluorescence) and the presence of the membrane protein is imaged.

In some examples, a nanopore detector can be used to test the affect of drug compounds on membranes. The affects of chemical compounds on membranes can also be determined. In some instances, the technique is powerful when multiple membranes comprising proteins are tested in parallel, or when multiple membrane/protein combinations are tested at once. In some cases, with a nanopore based massively parallel set of electrode/detectors one can test the same membrane/protein set representing one organism multiple times, and/or with separate wells on one sensor chip one can test many different kinds of membrane/protein combinations representing many different kinds of organisms at one time.

In some embodiments, the at least one membrane comprises a plurality of membranes formed over a plurality of conductive electrodes, where the electrodes are selectively energized to insert a subset of membrane proteins from a mixture comprising a plurality of membrane proteins into the membranes at the electrode positions, and where the membranes and/or membrane proteins are assayed at the electrode positions.

In some embodiments (e.g., because the membrane proteins only insert when induced to do so), different proteins can be flowed across a massively parallel array of electrode sensors separated in time, and by coordinating the application of electrical pulses with presence of a particular protein, each electrode detector can create its own population of particular proteins. Thus, the proteins that are known to reside in the membrane of a zebra fish can be created on electrode membranes 1-10, while a mimic of a human lung cell membrane wall with its appropriate proteins can be created on electrode membranes 11-20, soybean membrane and appropriate proteins on electrodes 30-40, and so on. In some embodiments, this programmable creation of artificial cellular membranes allows unprecedented visibility into the character of organisms.

Systems of the present disclosure can be used to select for membrane bound proteins or for porin proteins of interest. For example, by populating a massively parallel set of individually controlled electrode/membrane sensors with unknown pores and then testing them all for preferred responses to reagents or stimulus voltages and/or currents, the presence of a unique, preferred protein can be determined. In some instances, further screenings with limited proportions of the original testing mix allows a user to determine which exact porin is his molecule of interest. In some embodiments, this system allows for rapid selection for, or screening of, large numbers of mutations in membrane associated proteins.

Computer Systems

Figure 21:
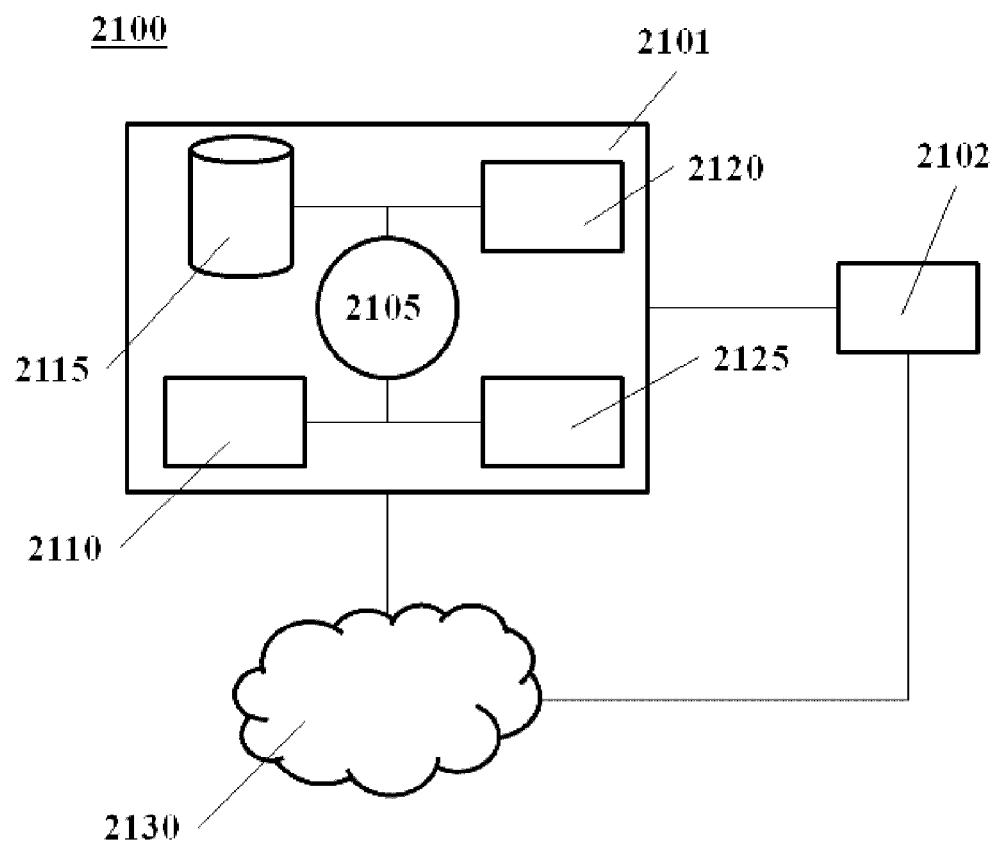
FIG. 21 shows a computer system configured to control a sequencer.

The devices, systems and methods of the disclosure may be regulated with the aid of computer systems. FIG. 21 shows a system 2100 comprising a computer system 2101 coupled to a nanopore detection and/or nucleic acid sequencing system 2102. The computer system 2101 may be a server or a plurality of servers. The computer system 2101 may be programmed to regulate sample preparation and processing, and nucleic acid sequencing by the sequencing system 2102. The sequencing system can be a nanopore device comprising a plurality of independently addressable nanopore sensors, as described elsewhere herein. The sequencing system 2102 can be a chip (or biochip). The computer system 2101 can include machine-executable code (e.g., software) that can be used to perform error detection in nucleic acid sequence information generated by the sequencing system 2102, and perform alignment of nucleic acid sequence data (also "reads" herein). The nanopore detection and/or sequencing system 2102 may be a nanopore-based sequencer (or detector), as described herein.

The computer system 2101 may be programmed to implement the methods of the disclosure. The computer system 2101 includes a central processing unit (CPU, also "processor" herein) 2105, which can be a single core or multi core processor, or a plurality of processors for parallel processing. The processor 2105 can be part of a circuit, such as an integrated circuit. In some examples, the processor 2105 can be integrated in an application specific integrated circuit (ASIC). The computer system 2101 also includes memory 2110 (e.g., random-access memory, read-only memory, flash memory), electronic storage unit 2115 (e.g., hard disk), communications interface 2120 (e.g., network adapter) for communicating with one or more other systems, and peripheral devices 2125, such as cache, other memory, data storage and/or electronic display adapters. The memory 2110, storage unit 2115, interface 2120 and peripheral devices 2125 are in communication with the CPU 2105 through a communications bus (solid lines), such as a motherboard. The storage unit 2115 can be a data storage unit (or data repository) for storing data. The computer system 2101 may be operatively coupled to a computer network ("network") with the aid of the communications interface 2120. The network can be the Internet, an internet and/or extranet, or an intranet and/or extranet that is in communication with the Internet. The network can include one or more computer servers, which can enable distributed computing.

In some examples, the computer system 2101 includes a field-programmable gate array (FPGA). The processor 2105 in such a case may be excluded.

Methods of the disclosure can be implemented by way of machine (or computer processor) executable code (or software) stored on an electronic storage location of the computer system 2101, such as, for example, on the memory 2110 or electronic storage unit 2115. During use, the code can be executed by the processor 2105. In some cases, the code can be retrieved from the storage unit 2115 and stored on the memory 2110 for ready access by the processor 2105. In some situations, the electronic storage unit 2115 can be precluded, and machine-executable instructions are stored on memory 2110.

The code can be pre-compiled and configured for use with a machine have a processer adapted to execute the code, or can be compiled during runtime. The code can be supplied in a programming language that can be selected to enable the code to execute in a pre-compiled or as-compiled fashion.

The computer system 2101 can be adapted to store user profile information, such as, for example, a name, physical address, email address, telephone number, instant messaging (IM) handle, educational information, work information, social likes and/or dislikes, and other information of potential relevance to the user or other users. Such profile information can be stored on the storage unit 2115 of the computer system 2101. The nanopore detection and/or nucleic acid sequencing system 2102 can be directly coupled to the computer system 2101 or go through the cloud (e.g., internet) 2130.

Aspects of the systems and methods provided herein, such as the computer system 2101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., ROM, RAM) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Biochips and Methods for Forming Biochips

Nanopores can be used to detect various molecules, including but not limited to sequencing polymers such as nucleic acid molecules. Recognized herein is the need for improved biochips and methods for making biochips (e.g., comprising nanopores). In some cases, conventional semiconductor processing techniques are deficient in producing a silicon device for use as a biochip. The present disclosure provides methods that can produce a biochip that withstands (e.g., is operable during or after contact with) highly corrosive environments such as aqueous solutions, optionally comprising ions. Such methods can be used to form biochips at high (e.g., at least about 500, 600, 700, 800, 900, 1000, 2000, 3000, 4000, 5000, 6000, 7000, 8000, 9000, or 10000 sites per mm$^2$). Each site can be an independently addressable site. In another aspect, the methods described herein create a biochip surface conducive to the formation of organic membranes (e.g., lipid bilayers). In another aspect, the methods provide electrochemical electrodes needed to perform electrical measurements of ionic current flows in the biochip.

Amongst other things, the biochips produced according to the methods described herein can be used for nucleic acid molecule identification and polymer (e.g., nucleic acid) sequencing. In some instances, the polymer is passed through the nanopore and various subunits of the polymer (e.g., adenine (A), cytosine (C), guanine (G), thymine (T) and/or uracil (U) bases of the nucleic acid) affect the current flowing through the nanopore. As described herein, the various subunits can be identified by measuring the current at a plurality of voltages applied across the nanopore and/or membrane. In some cases, the polymerization of tagged nucleotides releases and/or presents tag molecules to the nanopore that can be identified by measuring the current at a plurality of voltages applied across the nanopore and/or membrane.

Pore based sensors (e.g., biochips) can be used for electro-interrogation of single molecules. A pore based sensor of the present disclosure can include a nanopore formed in a membrane that is disposed adjacent or in proximity to a sensing electrode. The sensor can include a counter electrode. The membrane includes a trans side (i.e., side facing the sensing electrode) and a cis side (i.e., side facing the counter electrode).

Reference will now be made to the figures, wherein like numerals refer to like parts throughout. It will be appreciated that the figures and features therein are not necessarily drawn to scale.

Figure 22:
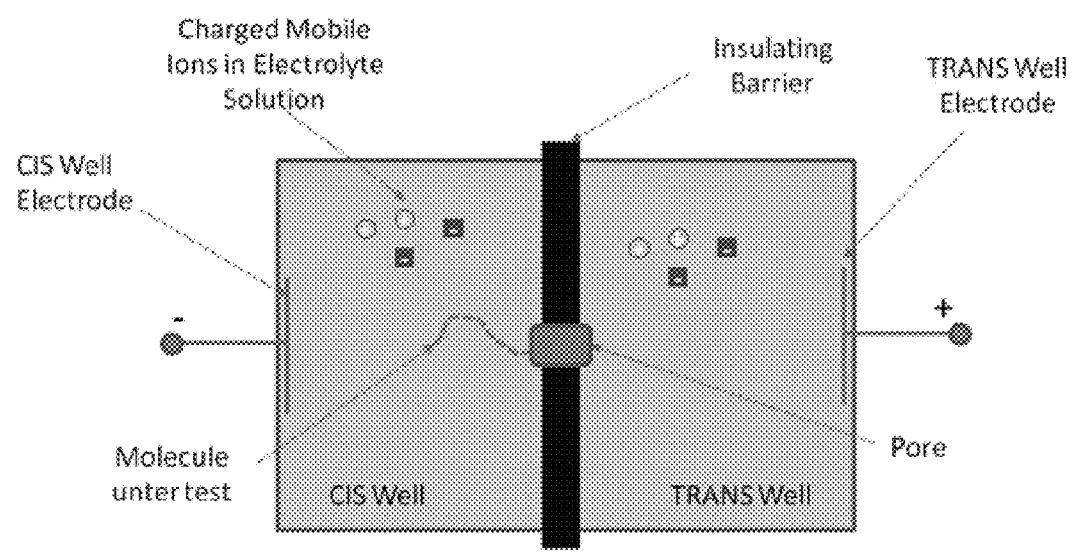
FIG. 22 shows a pore-based electrosensor.

With reference to FIG. 22, a typical electrical measurement can operate on a molecule under test that is closely associated with a pore (e.g., binding can be chemical, mechanical, electrical, or electrochemical). The system can apply a stimulus (voltage or current) across the molecule/pore complex and measure the response. In order to isolate the measurement to the pore/molecule complex the two sides of the pore are generally separated by a highly insulating material (e.g., a lipid bilayer).

The volumes enclosed on the opposite sides of the insulating barrier are referred to as the cis well and the trans well with the general definition that the species of interest (e.g., the nucleic acid molecule or tag molecule) moves from cis to trans during detection. The trans well is generally the side of the insulating membrane proximal to and electrically connected to the chip electrodes.

Figure 23:
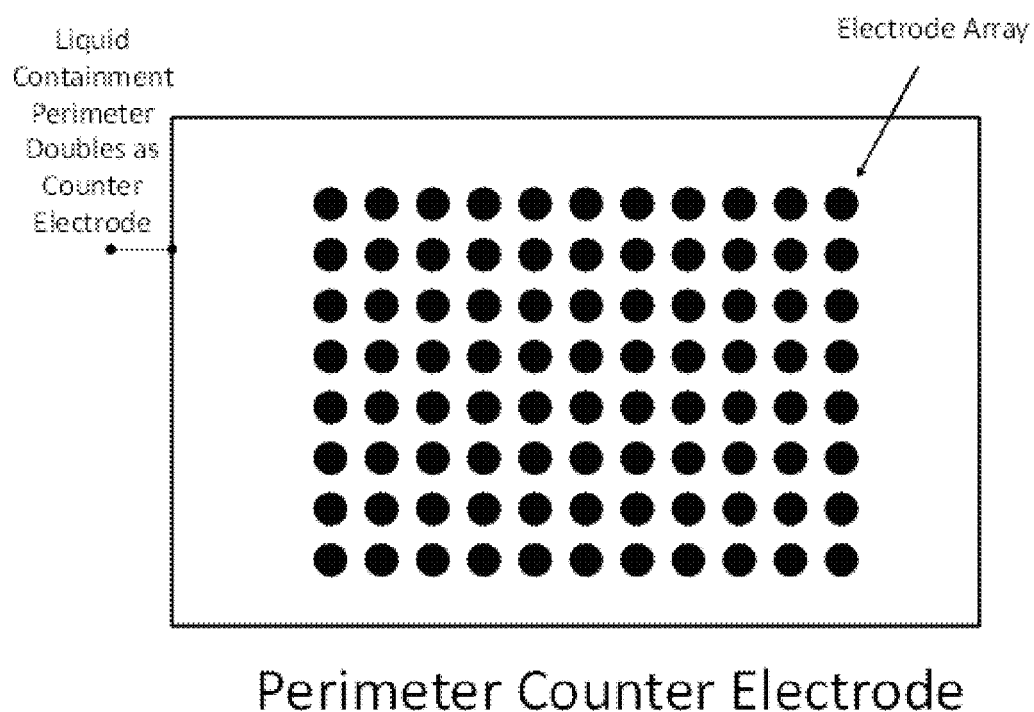
FIG. 23 shows an electrode array where the container doubles as a counter electrode.
Figure 24:
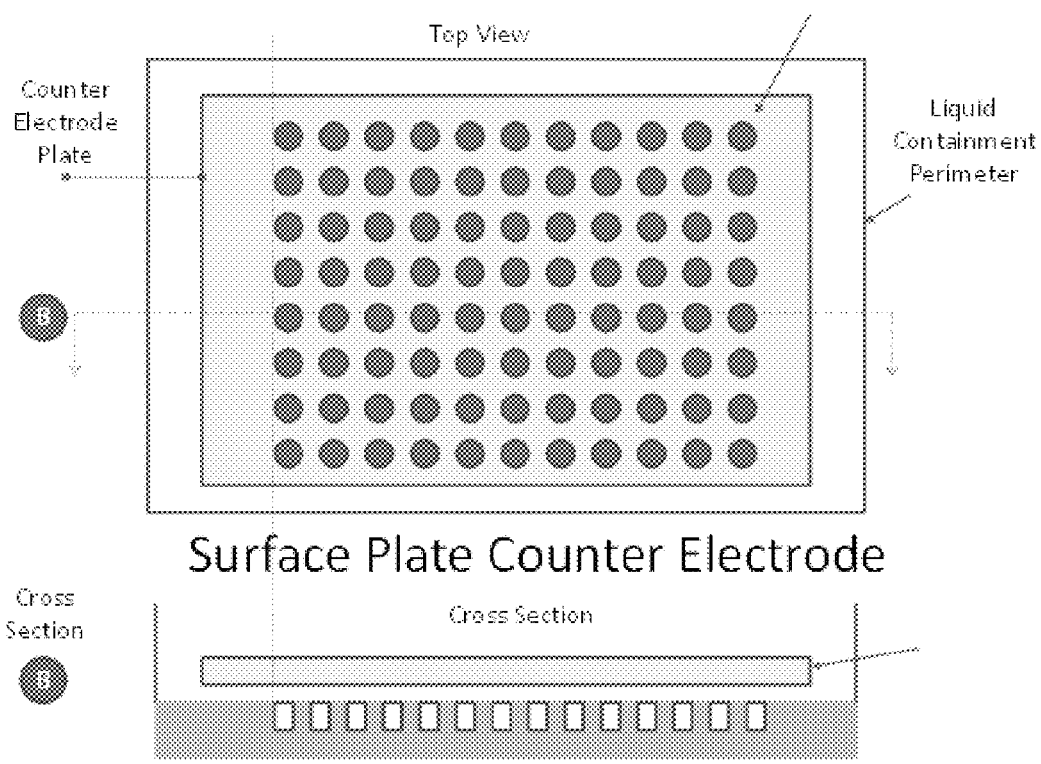
FIG. 24 shows an electrode array with a common counter electrode.
Figure 25:
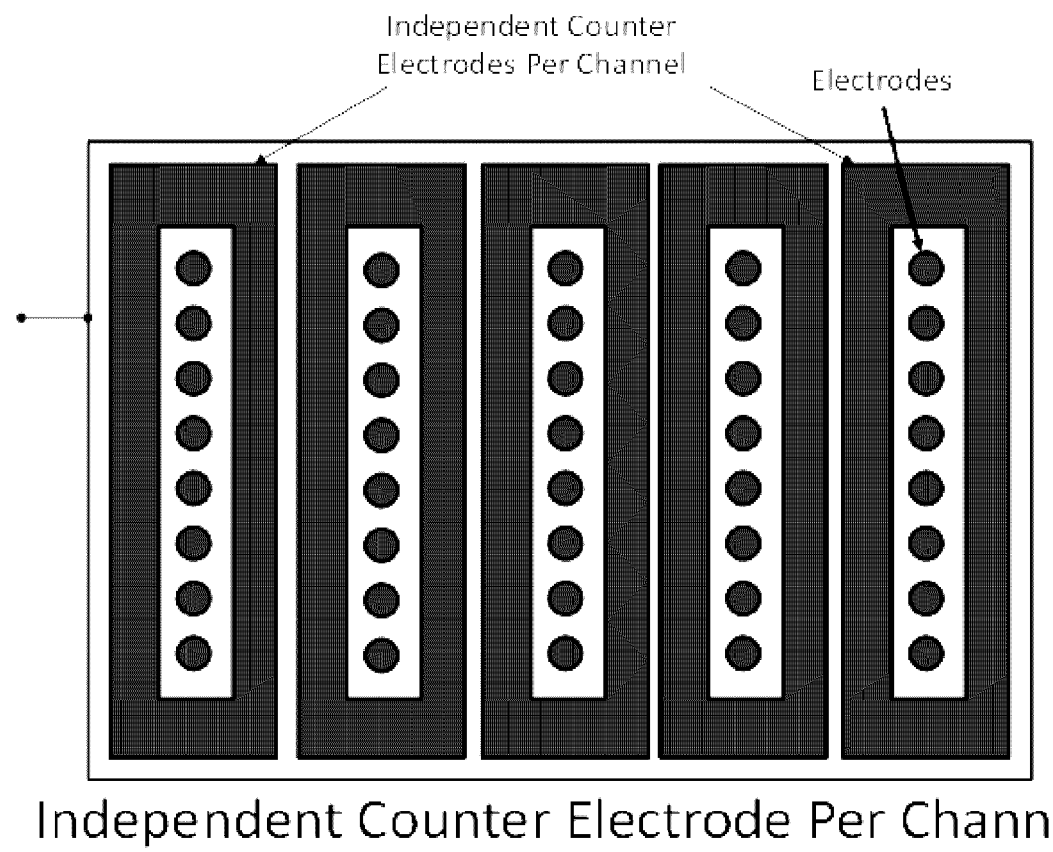
FIG. 25 shows an electrode array where strips of sensors share a common counter electrode.
Figure 26:
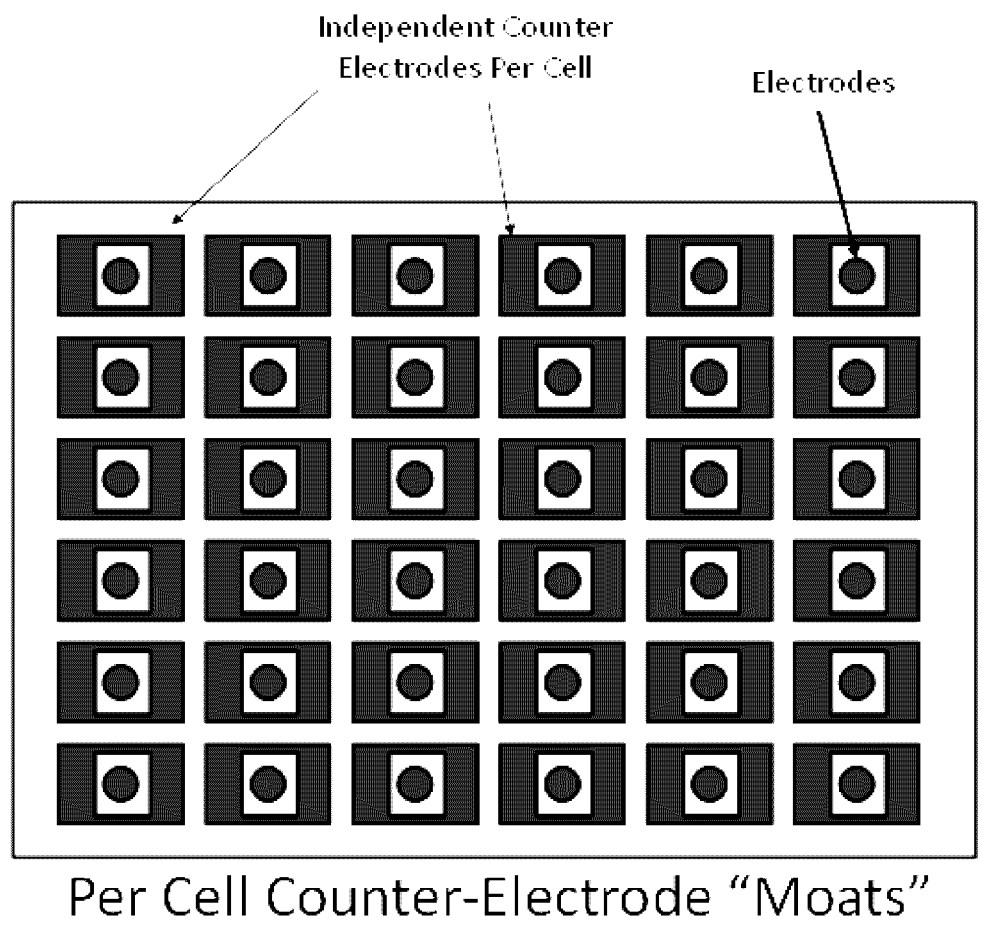
FIG. 26 shows and electrode array where each electrode has an independent counter electrode.

In some embodiments, the biochip comprises a counter electrode capable of forming an electrical circuit with the electrode in the well. In some cases, the plurality of electrodes in the plurality of wells share a common counter electrode. FIG. 23 shows an electrode array having a common counter electrode where the liquid containment perimeter (e.g., container) acts as a counter electrode (e.g., is conductive and forms a circuit). Another embodiment of a counter electrode is shown in FIG. 24, where the counter electrode is a plate (e.g., made of a conducting metal) over top of the nanopores. As shown in FIG. 25 and FIG. 26, the plurality of electrodes in the plurality of wells can be organized into groups that share a common counter electrode. In some cases, (e.g., FIG. 26), the plurality of electrodes in the plurality of wells each have a dedicated counter electrode. In some cases, having a plurality of counter electrodes can allow the sensing electrodes to be addressed individually (or in groups in the case of groups of electrodes sharing a common counter electrode).

Figure 27:
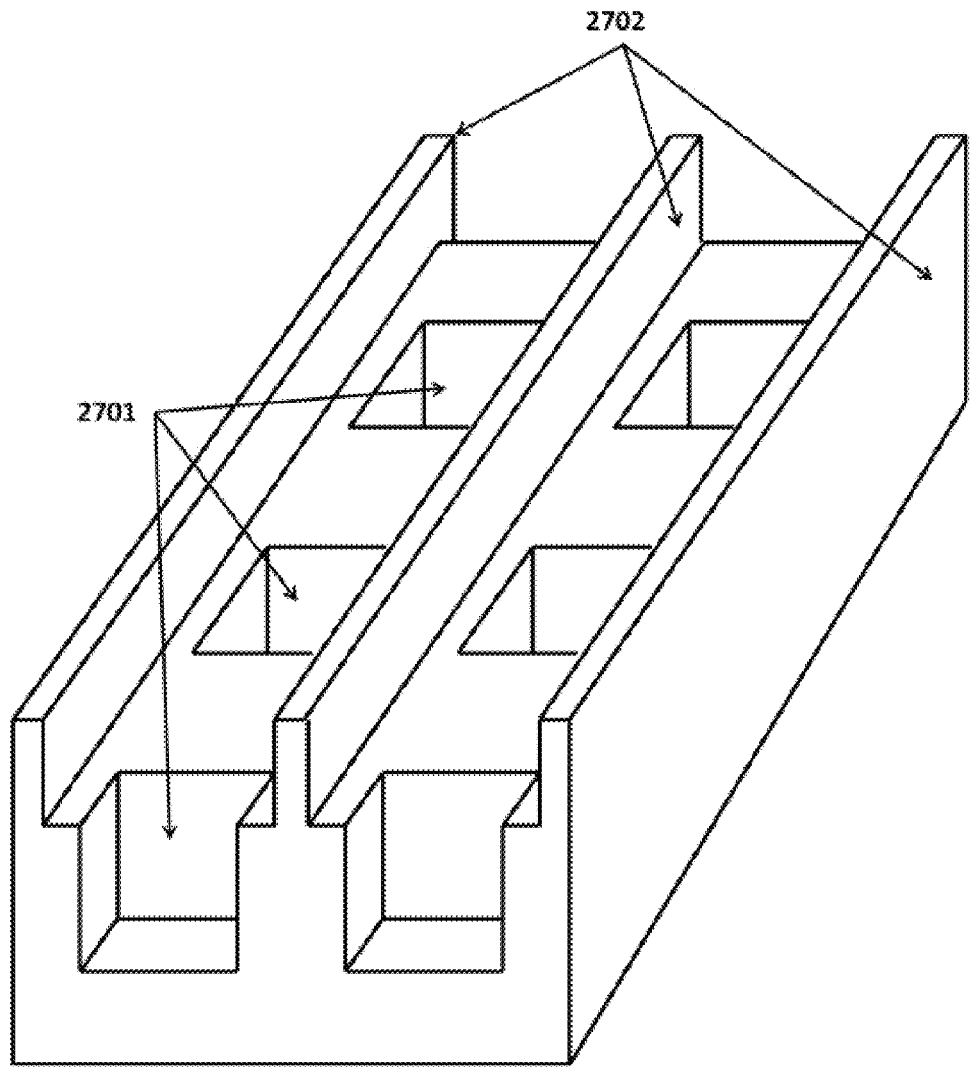
FIG. 27 shows an example of rows of sensor wells sharing a common electrolyte pool.

In some cases, a plurality of wells (including any subset of the total number of wells) comprise a common electrolyte pool. As shown in FIG. 27, the wells 2701 can be separated into rows by walls 2702 such that the row of wells share a common electrolyte pool above the wells. Separating the biochip into sections as described here can allow multiple samples to be analyzed on a single biochip (e.g., by putting different samples in different sections of the chip).

A nanopore sensor can include at least 1, 2, 3, 4, 5, 6, 7, 8, 9, 10, 20, 30, 40, 50, 100, or 1000 nanopores adjacent to a electrode (e.g., the bottom conductive electrode 202 of FIG. 1B). A nanopore sensor can include a top electrode (e.g., the top electrode 201 of FIG. 1B) that is for sole use by the nanopore sensor (and not other sensors), or as an alternative, a top electrode can be provided for use by multiple nanopore sensors.

Biochip Processing

Controlling surface characteristics, well cavity volume, and electrode composition and volume can be performed as described herein to produce a scalable semiconductor based planar array of microwells (e.g., for the purpose of nanopore sensing). In some instances, the nanopore based semiconductor array sensing platform achieves the following goals: (1) chip surface characteristics that support a planar insulating membrane, (2) differentiated surface characteristics that result in a well-defined and well controlled planar membrane surface, (3) large trans-well electrolyte volume, (4) large electrode volume, (5) low electrical cross-talk between adjacent sensor electrodes on the array, (6) high cell density in order to achieve very large array sizes, and (7) stable measurements of very long duration during which the key parameters (voltage, resistance, etc.) remain nearly constant.

For example meeting goals (1) & (2) can be difficult to ensure that a highly insulating (resistive) barrier is formed with well controlled membrane areas and trans-well volumes.

In the case of forming a lipid bilayer membrane, the design and processing of the chip can account for the hydrophilic head and hydrophobic tail of the phospholipid molecules. Careful control of the chip surface allows well defined hydrophilic and hydrophobic areas to be defined. In turn this can control the structure and characteristics of the lipid bilayer membranes formed.

Goal (3) can ensure that trans-well electrolytic ions are sufficiently abundant so as not to affect the results during the duration of a typical measurement. This can occur either by depleting one or the other of the ions entirely or shifting the relative concentration of the various ions to such a degree that they change the measurement results substantially (i.e. through shifts in concentration gradient and/or resulting Nernst potential).

Achieving Goal (4) can be of some importance in the case of a sacrificial electrode that is consumed or converted as part of the electro-chemical reaction that supports the measurement (e.g. silver being converted to silver-chloride oxidation reaction). Having a high electrode volume can be of some importance both to: (i) increase the time that a measurement can be continuously performed without intervening "recharging" measurements which can disrupt the experiment completely or result in gaps in the measured data and (ii) reduce electrochemical potential shifts caused by the change in relative concentrations of the oxidized and reduced electrode components. In some cases, complete depletion of the electrode material (silver) sets a theoretical upper boundary on practical continuous measurement duration.

In some cases, several of these goals can result in conflicts where meeting one goal comes at the expense of another. For example, etching a deep cavity in the silicon surface and filling completely with silver can achieve a planar membrane at the metal/silicon surface, thereby achieving goals (1), (2), and (4) however can leave little remaining volume available for trans-well electrolyte. Similarly, minimizing electrical cross-talk (goal 5) can be achieved by spacing adjacent cells far apart; however this can come at the expense of achieving goal (6).

In various aspects, the biochips and methods for making biochips described herein can achieve goals (1) to (6) in a way that is capable of sequencing nucleic acid molecules. For example, development of a deep well vertical cavity structure to support both electrolyte and electrode material can meet goals (3) and (4); a hybrid wet/dry etch can increase the lateral dimensions and thus trans well volume can meet goals (1), (2), (3), and (4); selective silanization of oxide surfaces can achieve goals (1) and (2); utilization of a gel can be used to balance goals (3) and (4) while simultaneously achieving goals (1) and (2); implementation of distributed counter electrode can simultaneously achieve goals (5) and (6); use of electrode replenishment (recharging) can achieve goal (7); use of non-sacrificial electrodes can achieve goal (7); electro-plating can increase electrode material to meet goal (4); or any combination thereof.

Biochip Characteristics

In an aspect, a biochip comprises a semiconductor substrate and a layer of silicon dioxide disposed on the substrate. A well can be formed into the silicon dioxide. A corrosion resistant material can coat the inside of the well. An electrode material can be in the well. An organofunctional alkoxysilane layer can coat the silicon dioxide. In some cases, the biochip further comprises a membrane isolating a first fluid in the well from a second fluid outside the well. Also encompassed within the present disclosure are the biochips made by any of the methods described herein and the use of any of the biochips described herein or biochips produced by the methods described herein to sequence polymers, including but not limited to nucleic acid molecules.

In some cases, electrode material is not depleted during operation of the biochip. In an aspect, a biochip comprises a plurality of wells having a membrane disposed over the well and an electrode in the well that is capable of detecting changes in the flow of ions through a pore in the membrane in response to entities passing through the pore. The electrode is not depleted during detection in some instances.

The electrode (e.g., silver or platinum material) can have any suitable mass or volume. In some cases, the volume of the electrode is about 0.1 femto-liter (fL), about 0.5 fL, about 1 fL, about 5 fL, or about 10 fL. In some instances, the volume of the electrode is at least about 0.1 femto-liter (fL), at least about 0.5 fL, at least about 1 fL, at least about 5 fL, or at least about 10 fL. In some embodiments, the volume of the electrode is at most about 0.1 femto-liter (fL), at most about 0.5 fL, at most about 1 fL, at most about 5 fL, or at most about 10 fL.

The electrode can be made of any suitable material, including mixtures and alloys of materials. Some examples include platinum, ferrocene, ferricyanide, or any combination thereof. In some cases, the electrode material is not consumed during operation of the electrode. The electrode can comprise a material that has at least two oxidation states and/or a material that is capable of both accepting and donating electrons.

Chip with Deep, Closely Packed Wells

Having a high density of nanopore sensors on the biochip can be desirable for having a small device and/or sensing or sequencing a large number of molecules with a small biochip device. The surface comprises any suitable density of discrete sites (e.g., a density suitable for sequencing a nucleic acid sample in a given amount of time or for a given cost). In an embodiment, the surface has a density of discrete sites greater than or equal to about 500 sites per 1 $mm^2$. In some embodiments, the surface has a density of discrete sites of about 100, about 200, about 300, about 400, about 500, about 600, about 700, about 800, about 900, about 1000, about 2000, about 3000, about 4000, about 5000, about 6000, about 7000, about 8000, about 9000, about 10000, about 20000, about 40000, about 60000, about 80000, about 100000, or about 500000 sites per 1 $mm^2$. In some embodiments, the surface has a density of discrete sites of at least about 200, at least about 300, at least about 400, at least about 500, at least about 600, at least about 700, at least about 800, at least about 900, at least about 1000, at least about 2000, at least about 3000, at least about 4000, at least about 5000, at least about 6000, at least about 7000, at least about 8000, at least about 9000, at least about 10000, at least about 20000, at least about 40000, at least about 60000, at least about 80000, at least about 100000, or at least about 500000 sites per 1 $mm^2$.

A biochip with a high density of discrete sites generally results in a well with a small area. In some instances, the well is suitably deep (e.g., such that the well has a suitably large volume). In an aspect, the volume of the well is suitably large such that an ion is not fully depleted in the well before recharging the electrode. In an aspect, the electrode can be a sacrificial electrode (e.g., an electrode that decreases and/or increases in volume during detection, such as silver) and the volume of the well is suitably large such that the electrode is not fully depleted before recharging the electrode. In some embodiments, the well contains a sufficiently large volume of electrode material such as silver. In these aspects, amongst others, the volume of the well can limit the time for which the electrode is capable of detecting a current (i.e., before an ion is depleted and/or the electrode material is depleted).

In some cases, the wells have a suitably large volume such that the electrode can detect ion flow (e.g., current) for about 1 millisecond (ms), about 5 ms, about 10 ms, about 50 ms, about 100 ms, about 500 ms, about 1 s, about 5 s, about 10 s, about 50 s, about 100 s, about 500 s, about 1000 s, or about 5000 s. In some embodiments, the wells have a suitably large volume such that the electrode can detect ion flow (e.g., current) for at least about 1 ms, at least about 5 ms, at least about 10 ms, at least about 50 ms, at least about 100 ms, at least about 500 ms, at least about 1 s, at least about 5 s, at least about 10 s, at least about 50 s, at least about 100 s, at least about 500 s, at least about 1000 s, or at least about 5000 s.

The time of detection can depend at least in part on the magnitude of the voltage applied across the nanopore and/or membrane (e.g., with higher voltage magnitudes resulting in higher ion current, faster depletion of electrodes and therefore relatively shorter detection periods). In some embodiments, the voltage difference across the membrane is about 40 milli-volts (mV), about 60 mV, about 80 mV, about 100 mV, about 120 mV, about 140 mV, about 160 mV, about 180 mV, about 200 mV, about 300 mV, about 400 mV, or about 500 mV. In some embodiments, the voltage difference across the membrane is at most about 40 mV, at most about 60 mV, at most about 80 mV, at most about 100 mV, at most about 120 mV, at most about 140 mV, at most about 160 mV, at most about 180 mV, at most about 200 mV, at most about 300 mV, at most about 400 mV, or at most about 500 mV. In some embodiments, the voltage difference across the membrane is at least about 40 mV, at least about 60 mV, at least about 80 mV, at least about 100 mV, at least about 120 mV, at least about 140 mV, at least about 160 mV, at least about 180 mV, at least about 200 mV, at least about 300 mV, at least about 400 mV, or at least about 500 mV. The voltage can be constant or variable (e.g., varying over any periodic waveform).

In some situations, the electrode has an operating life of at least about 1 minute ("min"), 2 min, 3 min, 4 min, 5 min, 6 min, 7 min, 8 min, 9 min, 10 min, 15 min, 20 min, 30 min, 40 min, 50 min, 1 hour, 2 hours, 3 hours, 4 hours, 5 hours, 6 hours, or 12 hours under an applied potential of at least about 40 mV, about 60 mV, about 80 mV, about 100 mV, about 120 mV, about 140 mV, about 160 mV, about 180 mV, about 200 mV, about 300 mV, about 400 mV, or about 500 mV. In some examples, the electrode has an operating life of at least about 15 min under an applied potential of about 80 mV.

The operating life of the electrode can be assessed based upon the depletion (e.g., rate of depletion) of the electrode during use. In some cases, the electrode material is depleted by at most about 50%, 40%, 30%, 20%, 10%, 9%, 8%, 7%, 6%, 5%, 4%, 3%, 2%, 1%, 0.1%, or 0.01% within a time period that is less than or equal to about 60 minutes, 30 minutes, 20 minutes, 15 minutes, 10 minutes, 5 minutes, 4 minutes, 3 minutes, 2 minutes, or 1 minute during use of the electrode.

The wells can have any suitable depth. In some cases, the depth of the well is measured from the surface of the biochip and/or bottom of the membrane to the top of the electrode and/or bottom of the electrode. In some cases, the depth of the well is approximately equal to the thickness of an oxide layer (e.g., 103 in FIG. 1B). In some embodiments, the wells are about 0.5 micrometers (μm), about 1 μm, about 1.5 μm, about 2 μm, about 2.5 μm, about 3 μm, about 3.5 μm, about 4 μm, about 4.5 μm, about 5 μm, about 6 μm, about 7 μm, about 8 μm, about 9 μm, about 10 μm, or about 20 μm deep. In some embodiments, the wells are at least about 0.5 micrometers (μm), at least about 1 μm, at least about 1.5 μm, at least about 2 μm, at least about 2.5 μm, at least about 3 μm, at least about 3.5 μm, at least about 4 μm, at least about 4.5 μm, at least about 5 μm, at least about 6 μm, at least about 7 μm, at least about 8 μm, at least about 9 μm, at least about 10 μm, or at least about 20 μm deep.

In an aspect, a biochip comprises a plurality of wells having a membrane disposed over the well and an electrode in the well that is capable of detecting changes in the flow of ions through a pore in the membrane in response to entities passing through the pore. The biochip can comprise at least 500 wells per square millimeter and the wells can have a suitably large volume such that the electrode can detect at least 100 entities without recharging the electrode.

In some embodiments, the entities are tag molecules released upon nucleotide incorporation events. In some instances, a polymer passes through the pore and the entities are subunits of the polymer. In some cases, the polymer is a nucleic acid and the subunits of the polymer are nucleobases.

The biochip can detect any suitable number of entities without recharging the electrode. In some cases, about 10, about 50, about 100, about 500, about 1000, about 5000, about 10000, about 50000, about 100000, about 500000, about 1000000, about 5000000, or about 10000000 entities are detected. In some cases, at least about 10, at least about 50, at least about 100, at least about 500, at least about 1000, at least about 5000, at least about 10000, at least about 50000, at least about 100000, at least about 500000, at least about 1000000, at least about 5000000, or at least about 10000000 entities are detected.

Chip with Closely Packed Wells and Minimum Cross-Talk

In an aspect, the wells are closely packed and have a low amount of cross-talk (e.g., the electrodes derive all or most of their signal from the nanopore and/or membrane nearest to the electrode). In an aspect, a biochip comprises a plurality of wells having a membrane disposed over the well and an electrode in the well that detects a signal in response to the flow of ions. The biochip can comprise at least 500 wells per square millimeter and the electrodes are electrically isolated from each other. The biochip can comprise any suitable number of wells per area as described herein.

In some cases, an electrode detects about 80%, about 90%, about 95%, about 99%, about 99.5%, or about 99.9% of its signal from the flow of ions through a nanopore in the membrane. In some instances, the electrode detects at least about 80%, at least about 90%, at least about 95%, at least about 99%, at least about 99.5%, or at least about 99.9% of its signal from the flow of ions through a nanopore in the membrane. In some cases, an electrode detects no more than 20%, no more than 10%, no more than 5%, no more than 1%, no more than 0.5%, or no more than 0.1%, of its signal from the flow of ions through nanopores in adjacent wells.

Methods for Making Biochips

The methods can be used to make high quality biochips that are capable of withstanding corrosive solutions and forming a membrane on the biochip that has a high resistivity. In an aspect, a method for preparing a biochip comprises providing a semiconductor substrate and forming a plurality of wells containing electrodes capable of performing electrical measurements on or adjacent to the substrate. In some cases, the method further comprises treating the substrate to withstand corrosive solutions and preparing the substrate for the formation of a membrane that seals the well with a high resistivity.

The membrane can have any suitably high resistivity. In some cases, the resistivity is about 10 mega-ohms (MΩ), about 50 MΩ, about 100 MΩ, about 500 MΩ, about 1 giga-ohm (GΩ), about 5 GΩ, or about 10 GΩ. In some cases, the resistivity is at least about 10 mega-ohms (MΩ), at least about 50 MΩ, at least about 100 MΩ, at least about 500 MΩ, at least about 1 giga-ohm (GΩ), at least about 5 GΩ, or at least about 10 GΩ.

In some embodiments, the semiconductor substrate comprises silicon. In some instances, the membrane is a lipid bilayer. The electrodes can be capable of measuring ionic current flows through a nanopore embedded in the membrane.

The device can withstand any suitable corrosive solution. In some cases, the corrosive solutions are aqueous (include water) and comprise ions (e.g., $Na^+$, $Cl^-$). In some cases, the biochip is operable after contacting for 10 hours with 1 M NaCl.

In some examples, a method for preparing a biochip comprises depositing a material having reactive oxide groups on a semiconductor substrate, etching wells into the silicon dioxide, forming metal electrodes in the wells, removing metal from all areas of the substrate except for the wells, and coating the substrate with a layer suitable for adhesion of a membrane. In some cases, the semiconductor substrate comprises silicon. The method can prepare the biochip for use in nucleic acid sequencing using a nanopore.

In some cases, the material having reactive oxide groups is silicon dioxide. The material can present a hard, planar surface that exhibits a uniform covering of reactive oxide (—OH) groups to a solution in contact with its surface. These oxide groups can be the attachment points for the subsequent silanization process. Alternatively, a lipophillic and hydrophobic surface material can be deposited that mimics the etching characteristics of silicon oxide.

In some embodiments, a passivation layer is deposited on the semiconductor substrate, which may or may not have reactive oxide groups. The passivation layer can comprise silicon nitride ($Si_3N_4$) or polymide. In some instances, a photolithographic step is used to define regions where membranes form on the passivation layer. The photolithographic step can be used to define the regions using a photoresist and exposing portions of the photoresist through a mask. The density of sites (e.g., 500 sites per $mm^2$) in the biochip can be defined by selecting the density of features (e.g., holes representing cross-sections of wells) in the mask and the exposed portions of the photoresist.

FIG. 28 to FIG. 41 show an example of steps that can result in biochips. All figures are not necessarily drawn to scale.

With reference to FIG. 28, the method for producing a biochip can start with a semiconductor substrate. The semiconductor (e.g., silicon) can have any number of layers disposed upon it, including but not limited to a conducting layer such as a metal. The conducting layer is aluminum in some instances. In some cases, the substrate has a protective layer (e.g., titanium nitride). The layers can be deposited with the aid of various deposition techniques, such as, for example, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD) and physical vapor deposition (e.g., sputter deposition, evaporative deposition).

Figure 29:
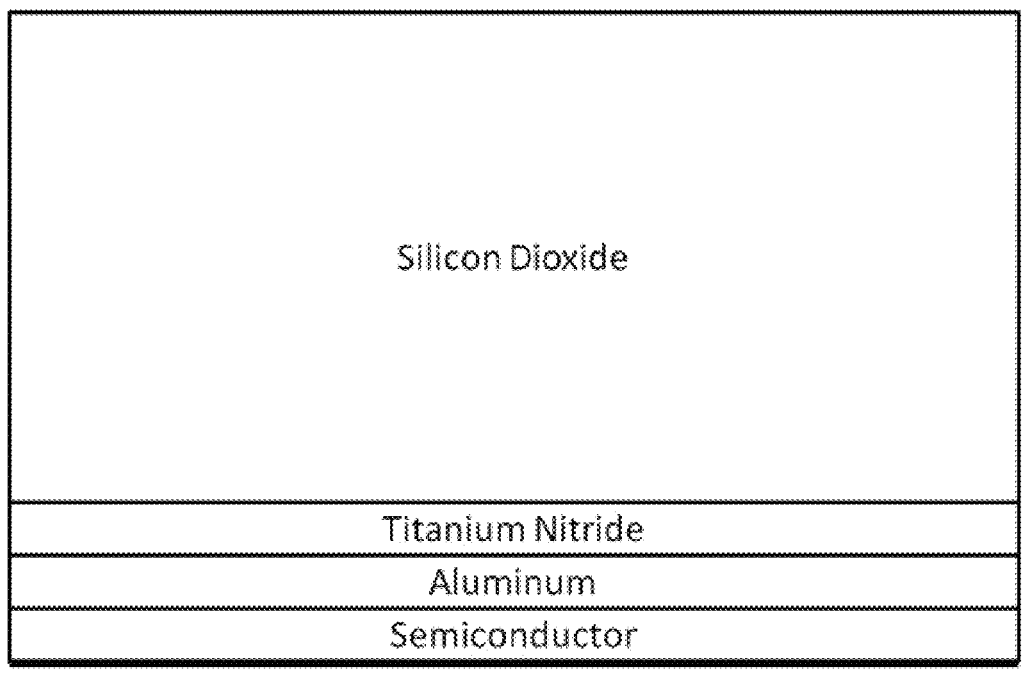
FIG. 29 shows a layer of silicon dioxide deposited on a semiconductor substrate.

In some cases, an oxide layer is deposited on the semiconductor substrate as shown in FIG. 29. In some instances, the oxide layer comprises silicon dioxide. The silicon dioxide can be deposited using tetraethyl orthosilicate (TEOS), high density plasma (HDP), or any combination thereof.

In some instances, the silicon dioxide is deposited using a low temperature technique. In some cases, the process is low-temperature chemical vapor deposition of silicon oxide. The temperature is generally sufficiently low such that pre-existing metal on the chip is not damaged. The deposition temperature can be about 50° C., about 100° C., about 150° C., about 200° C., about 250° C., about 300° C., about 350° C., and the like. In some embodiments, the deposition temperature is below about 50° C., below about 100° C., below about 150° C., below about 200° C., below about 250° C., below about 300° C., below about 350° C., and the like. The deposition can be performed at any suitable pressure. In some instances, the deposition process uses RF plasma energy.

In some cases, the oxide is not deposited by a thermally grown oxide procedure (e.g., which can use temperatures near or exceeding 1,000° C.).

The silicon dioxide can be deposited to a thickness suitable for the formation of wells comprising electrodes and a volume of electrolyte capable of sequencing at least 100, at least 1000, at least 10000, at least 100000, or at least 1000000 nucleobases of a nucleic acid molecule without recharging the electrodes.

The silicon dioxide can be deposited to any suitable thickness. In some embodiments, the silicon dioxide is about 0.5 micrometers (μm), about 1 μm, about 1.5 μm, about 2 μm, about 2.5 μm, about 3 μm, about 3.5 μm, about 4 μm, about 4.5 μm, about 5 μm, about 6 μm, about 7 μm, about 8 μm, about 9 μm, about 10 μm, or about 20 μm thick. In some embodiments, the silicon dioxide is at least about 0.5 micrometers (μm), at least about 1 μm, at least about 1.5 μm, at least about 2 μm, at least about 2.5 μm, at least about 3 μm, at least about 3.5 μm, at least about 4 μm, at least about 4.5 μm, at least about 5 μm, at least about 6 μm, at least about 7 μm, at least about 8 μm, at least about 9 μm, at least about 10 μm, or at least about 20 μm thick.

Well Etching

A biochip can comprise wells. An individual well can include a nanopore in a membrane in or over the well. A well can be part of an independently addressable nanopore sensor.

Figure 30:
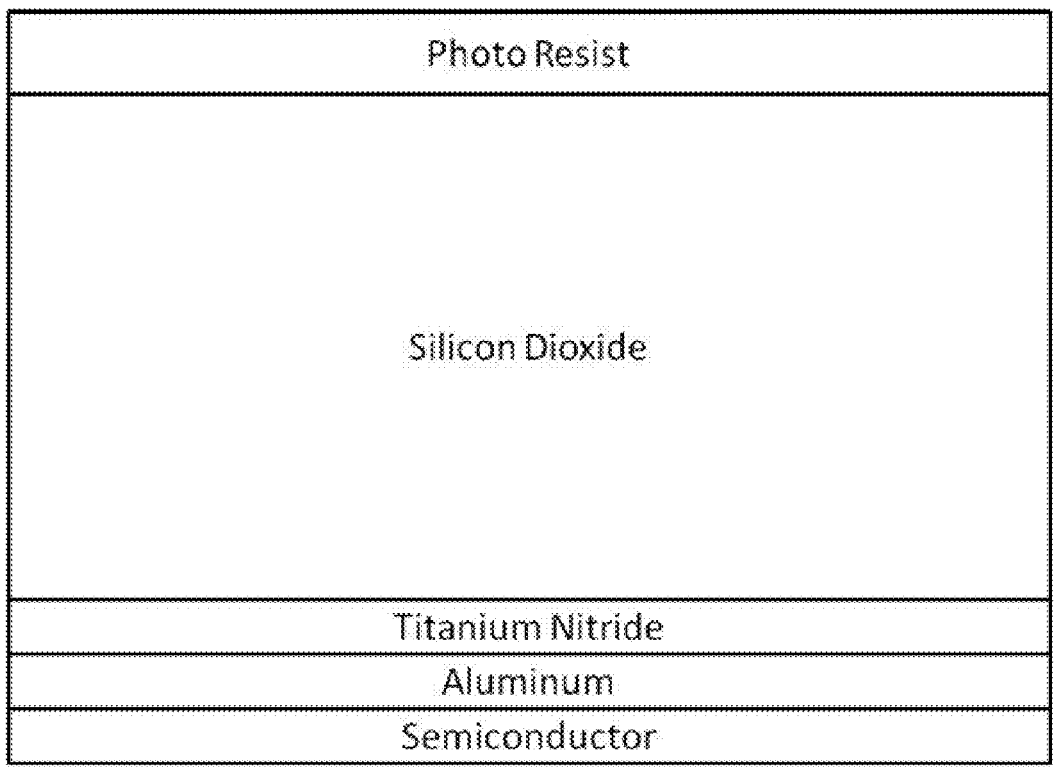
FIG. 30 shows a photo-resist deposited on a silicon dioxide layer.
Figure 31:
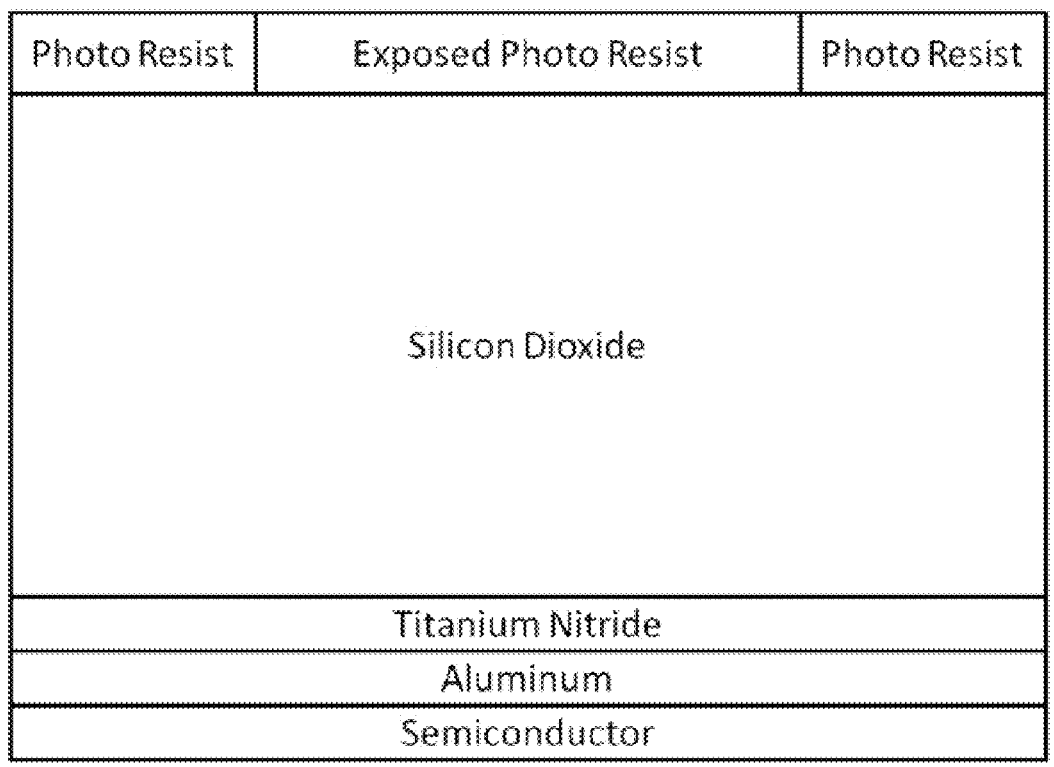
FIG. 31 shows an area of the photo-resist being exposed to radiation to define the area of a well.

Wells can be created in a silicon dioxide substrate using various manufacturing techniques. Such techniques can include semiconductor fabrication techniques. In some cases, the wells are created using photolithographic techniques such as those used in the semiconductor industry. For example, a photo-resist (e.g., a material that changes properties when exposed to electromagnetic radiation) can be coated onto the silicon dioxide (e.g., by spin coating of a wafer) to any suitable thickness as shown in FIG. 30. The substrate including the photo-resist can then be exposed to an electromagnetic radiation source. A mask can be used to shield radiation from portions of the photo-resist in order to define the area of the wells. The photo-resist can be a negative resist or a positive resist (e.g., the area of the well can be exposed to electromagnetic radiation or the areas other than the well can be exposed to electromagnetic radiation as defined by the mask). In FIG. 31, the area overlying the location in which the wells are to be created is exposed to electromagnetic radiation to define a pattern that corresponds to the location and distribution of the wells in the silicon dioxide layer. The density of sites (e.g., 500 sites per $mm^2$) in the biochip can be defined by selecting the density of features (e.g., holes representing cross-sections of wells) in the mask. The photoresist can be exposed to electromagnetic radiation through a mask defining a pattern that corresponds to the wells. Next, the exposed portion of the photoresist can be removed, such as, e.g., with the aid of a washing operation (e.g., deionized water). The removed portion of the mask can then be exposed to a chemical etchant to etch the substrate and transfer the pattern of wells into the silicon dioxide layer. The etchant can include an acid, such as, for example, sulfuric acid ($H_2SO_4$). The silicon dioxide layer can be etched in an anisotropic fashion, though in some cases etching can be isotropic. For instance, with reference to FIG. 33, an area not corresponding exactly to the area of a final well can be etched (e.g., the well can be etched under the photo-resist).

Figure 32:
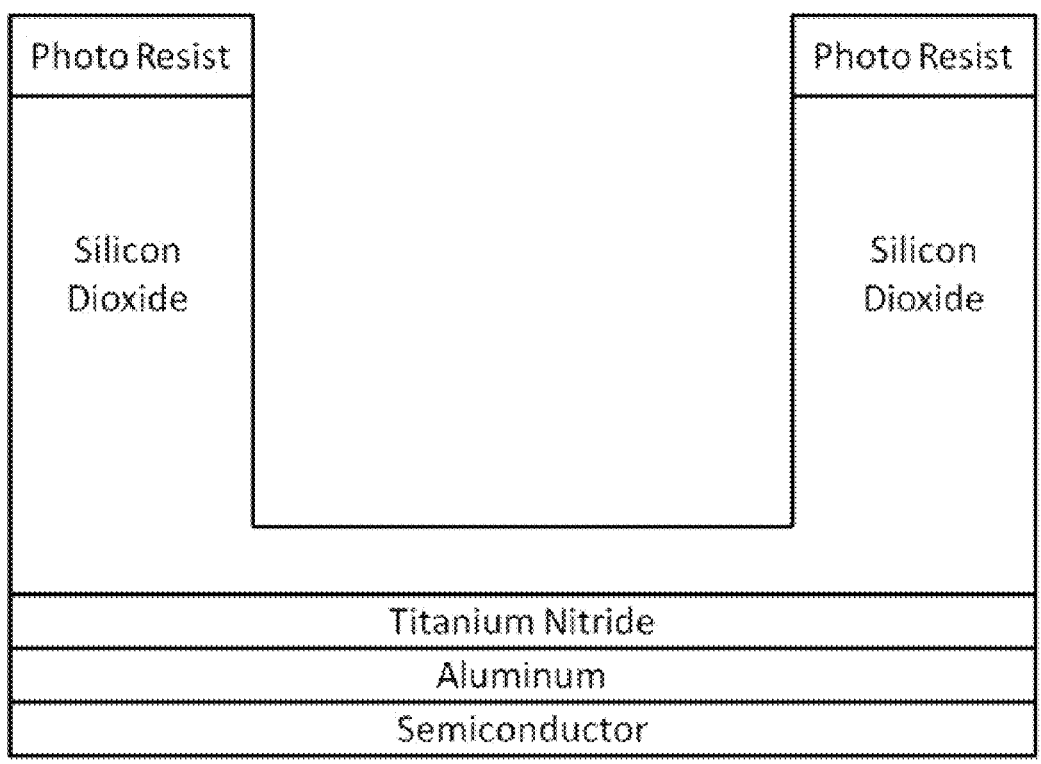
FIG. 32 shows a portion of the silicon dioxide being removed by a dry etch procedure.
Figure 33:
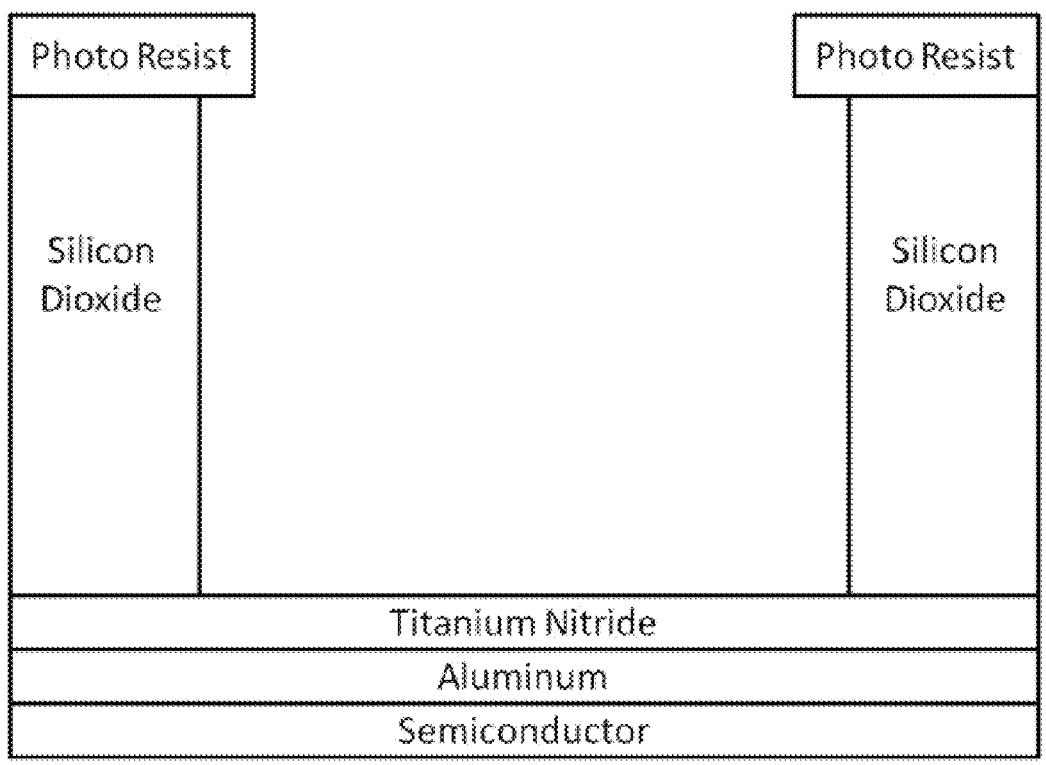
FIG. 33 shows additional silicon dioxide being removed by a wet etch procedure to create a well.

Various etching procedures can be used to etch the silicon dioxide in the area where the well is to be formed. As shown in FIG. 32 and FIG. 33, the etch can be an isotropic etch (i.e., the etch rate alone one direction is equal to the etch rate along an orthogonal direction), or an anisotropic etch (i.e., the etch rate along one direction is less than the etch rate alone an orthogonal direction), or variants thereof.

In some cases, an anisotropic etch removes the majority of the volume of the well. Any suitable percentage of the well volume can be removed including about 60%, about 70%, about 80%, about 90%, or about 95%. In some cases, at least about 60%, at least about 70%, at least about 80%, at least about 90%, or at least about 95% of the material is removed in an anisotropic etch. In some cases, at most about 60%, at most about 70%, at most about 80%, at most about 90%, or at most about 95% of the material is removed in an anisotropic etch. In some embodiments, the anisotropic etch does not remove silicon dioxide material all of the way down to the semiconductor substrate. An isotropic etch removes the silicon dioxide material all of the way down to the semiconductor substrate in some instances.

In some cases, the wells are etched using a photo-lithographic step to define the wells followed by a hybrid dry-wet etch. The photo-lithographic step can comprise coating the silicon dioxide with a photo-resist and exposing the photo-resist to electromagnetic radiation through a mask (or reticle) having a pattern that defines the wells. In some instances, the hybrid dry-wet etch comprises dry etching to remove the bulk of the silicon dioxide in the well regions defined in the photoresist by the photo-lithographic step, cleaning the biochip, and wet etching to remove the remaining silicon dioxide from the substrate in the well regions.

The biochip can be cleaned with the aid of a plasma etching chemistry, or exposure to an oxidizing agent, such as, for example, hydrogen peroxide ($H_2O_2$), oxide anion ($O_2^-$), or ozone ($O_3$). The cleaning can comprise removing residual polymer, removing material that can block the wet etch, or a combination thereof. In some instances, the cleaning is plasma cleaning. The cleaning step can proceed for any suitable period of time (e.g., 15 to 20 seconds). In an example, the cleaning can be performed for 20 seconds with an eMAx-CT machine (Applied Materials, Sunnyvale Calif.) with settings of 100 mT, 200 W, 20 G, 20 $O_2$.

The dry etch can be an anisotropic etch that etches vertically (e.g., toward the semiconductor substrate) but not laterally (e.g., parallel to the semiconductor substrate). In some instances, the dry etch comprises etching with a fluorine based etchant such as $CF_4$, $CHF_3$, $C_2F_6$, $C_3F_6$, or any combination thereof. In one instance, the etching is performed for 400 seconds with an eMax-CT machine (Applied Materials, Sunnyvale Calif.) having settings of 100 mT, 1000 W, 20 G, and 50 $CF_4$.

The wet etch can be an isotropic etch that removes material in all directions. In some instances, the wet etch undercuts the photo-resist. Undercutting the photo-resist can make the photo-resist easier to remove in a later step (e.g., photo-resist "lift off"). In an embodiment, the wet etch is buffered oxide etch (BOE). In some cases, the wet oxide etches are performed at room temperature with a hydrofluoric acid base that can be buffered (e.g., with ammonium fluoride) to slow down the etch rate. Etch rate can be dependent on the film being etched and specific concentrations of HF and/or $NH_4F$. The etch time needed to completely remove an oxide layer is typically determined empirically. In one example, the etch is performed at 22° C. with 15:1 BOE (buffered oxide etch).

The silicon dioxide layer can be etched to an underlying material layer. For example, with reference to FIG. 33, the silicon dioxide layer is etched until the titanium nitride layer.

In an aspect, a method for preparing a biochip comprises etching wells into a silicon dioxide layer coated onto a semiconductor substrate using a photo-lithographic step to define the wells, a dry etch to remove the bulk of the silicon dioxide in the well regions defined by the photo-lithographic step, and a wet etch to remove the remaining silicon dioxide from the substrate in the well regions. In some cases, the method further comprises removing residual polymer, removing material that can block the wet etch, or a combination thereof. The method can include a plasma cleaning step.

As shown in FIG. 33, the photo-resist is not removed from the silicon dioxide following the photo-lithographic step or the hybrid wet-dry etch in some cases. Leaving the photo-resist can be used to direct metal only into the wells and not onto the upper surface of the silicon dioxide in later steps. In some cases, the semiconductor substrate is coated with a metal (e.g., aluminum in FIG. 33) and the wet etch does not remove components that protect the metal from corrosion (e.g., titanium nitride (TiN) in FIG. 33). In some cases, however, the photoresist layer can be removed, such as with the aid of chemical mechanical planarization (CMP).

Electrode Metallization

The biochips described herein can be used to detect molecules and/or sequence nucleic acid molecules with aid of a nanopore and electrical detection. Electrical detection can be performed with aid of an electrode in the well and a counter-electrode located outside the well. Provided herein are methods for creating electrodes, such as metal electrodes. The electrode can be reversibly consumed during detection, not consumed during detection, or not appreciably consumed during detection.

An example of an electrode that can be reversibly consumed during molecular detection is silver. An example of an electrode that may not be appreciably consumed during detection is platinum.

An electrode can be formed adjacent to a substrate with the aid of various deposition techniques. For instance, an electrode can be formed with the aid of electroplating. As another example, an electrode can be formed with the aid of a vapor deposition techniques, such as, for example, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD) and physical vapor deposition (e.g., sputter deposition, evaporative deposition).

Figure 34:
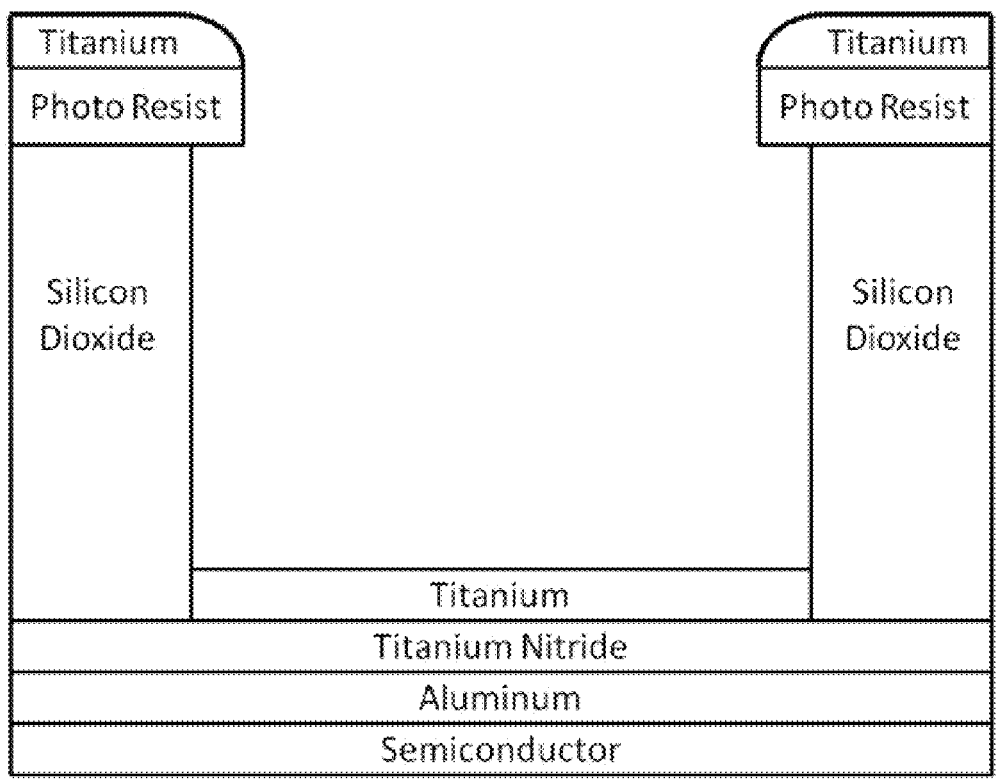
FIG. 34 shows deposition of a titanium adhesion layer.
Figure 35:
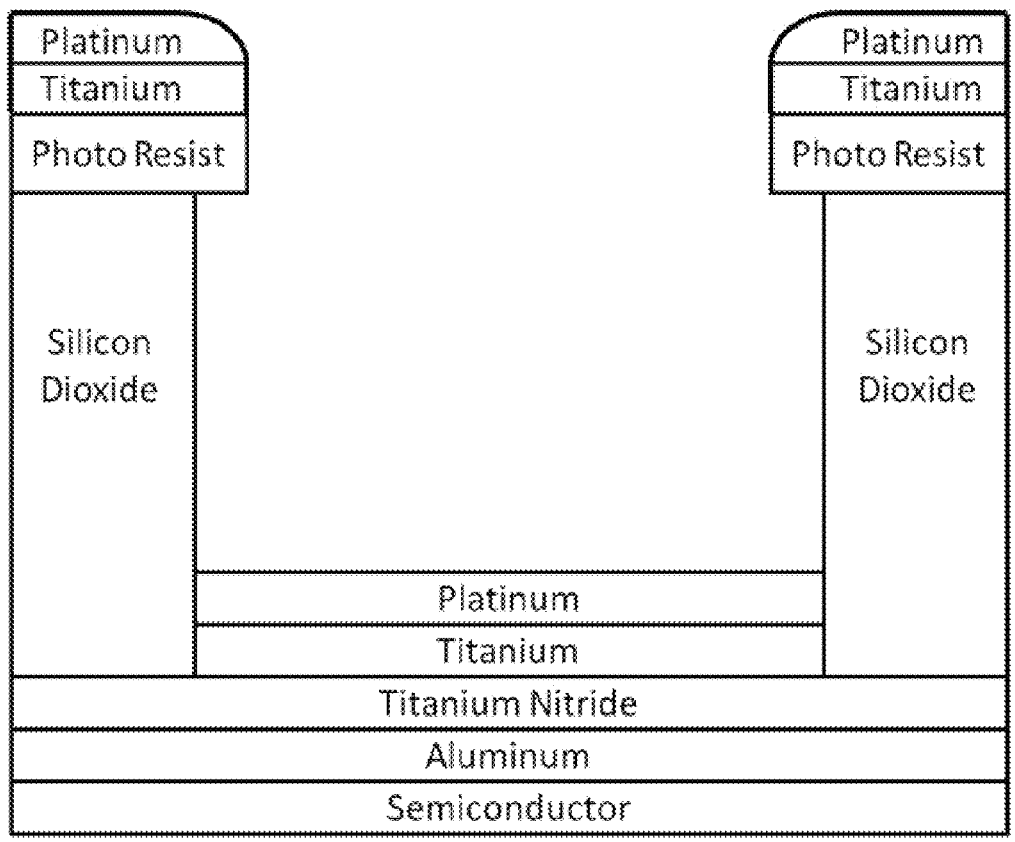
FIG. 35 shows deposition of a platinum protective layer.
Figure 36:
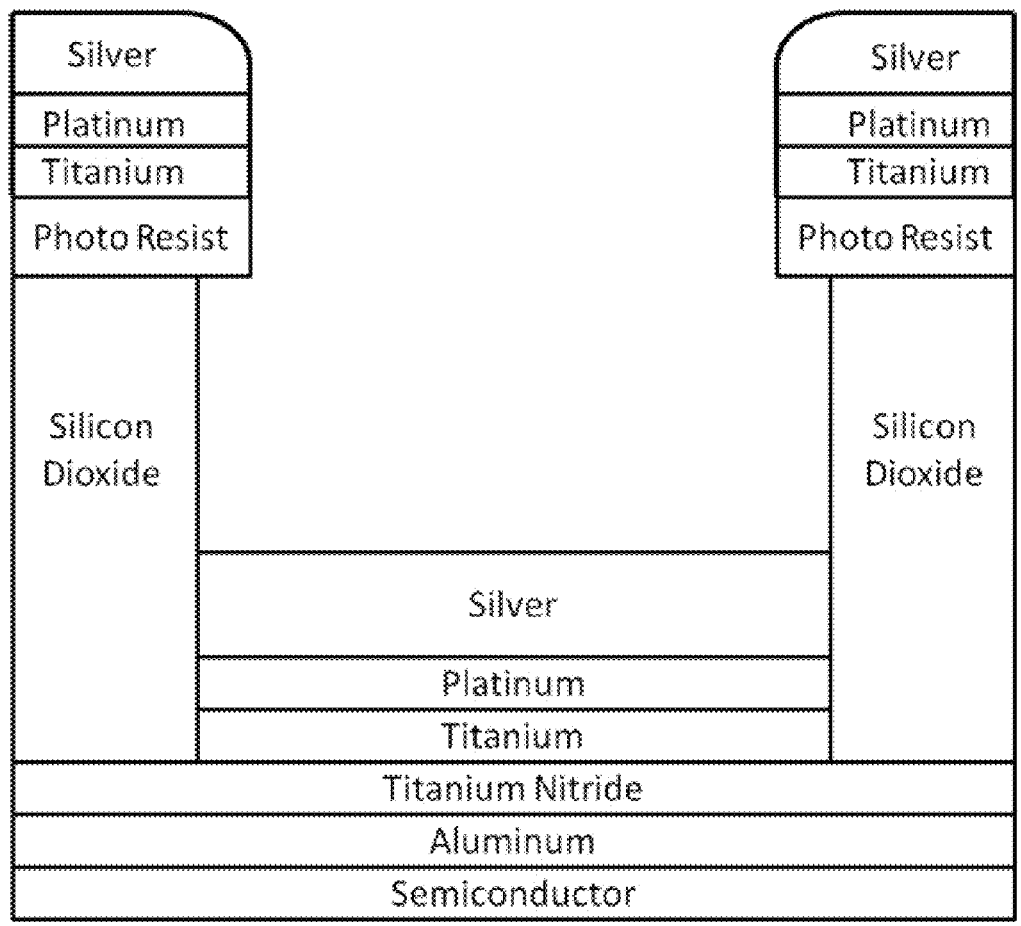
FIG. 36 shows deposition of silver electrode material.

In an aspect, a method for preparing a biochip comprises providing a semiconductor substrate coated with a layer of silicon dioxide, where a well is etched into the silicon dioxide (e.g., as shown in FIG. 33). The method can comprise depositing a protective layer onto the well surface (e.g., platinum as shown in FIG. 35) and depositing the electrode material onto the well surface (e.g., silver as shown in FIG. 36). The method can further comprise depositing a film of adhesion material onto the well surface to provide for adhesion and electrical conductivity of a metal layer to a layer below the metal layer. The adhesion material can comprise titanium, tantalum, titanium nitride (TiN), chromium, or any combination thereof. With reference to FIG. 34, an adhesion material comprising titanium can be deposited adjacent to the titanium nitride layer, such as, for example, by electroplating, or vapor deposition (e.g., chemical vapor deposition). In some cases, a single layer of metal replaces two or more layers (e.g., a single metal layer is both the adhesion layer and protective layer).

In some cases, the protective layer comprises a corrosive resistant metal (e.g., platinum, gold). Without limitation, the protective layer can provide electrical connectivity to an underlying conductor (e.g., to aluminum in FIG. 34, or titanium nitride), protect the underlying conductor from attack by a reactive solution (e.g., a corrosive solution such as sodium chloride in water), provide an electron source and/or sink so that an electrode material is not consumed in redox reactions (e.g., platinum can act as the source and/or sink when the electrode comprises silver), or any combination thereof.

The various layers of metal (e.g., adhesion layer, protective layer, electrode material, etc.) can be deposited by any suitable technique, such as sputtering, deposition, electroplating, or a combination thereof. In some instances, the electrode material is deposited by sputtering, such as, for example, magnetron sputtering.

The electrodes are capable of making any suitable measurement as required for operation of the biochip. In some cases, the electrode material makes electrical measurements of analytes in the wells. The analytes can comprise nucleic acids, amino acids, proteins, tag molecules, or any combination thereof. The electrical measurements can reversible redox reactions. In some embodiments, a sufficient volume of the electrode material is deposited into the well to provide for detection of redox reactions involving analytes in the wells.

Lift-Off Procedure

There can be one or more layers of metal deposited onto the photo-resist following electrode metallization as shown in FIG. 36. In some instances, the metal deposited onto the photo-resist is removed from the biochip while the metal deposited in the wells remains in the wells. Leaving the photo-resist following creation of the wells (e.g., as shown in FIG. 33) can be advantageous for achieving metal removal from only the surface of the biochip and not the wells.

In some situations, following formation of a well and an electrode, the photoresist and any material layers over the photoresist can be removed with the aid of a chemical or mechanical etching operation. In an example, chemical mechanical planarization (CMP) is used to remove the photoresist and any material layers over the phororesist. In another example, the photoresist and any overlying layer is removed using acetone.

Silanization of the Biochip Surface

Following formation of a well and electrode within the well, the silicon dioxide layer can be treated to render the silicon dioxide layer suitable for forming a membrane in or adjacent to the well. In some cases, a hydrophobic membrane, such as, for example, a bilayer (e.g., lipid bilayer), is formed over the well. The membrane can isolate the etched well from an overlying liquid, such as, for example, with a resistivity of at least about 10 gigaohms. As described herein, silanization of the silicon dioxide surface (e.g., to make the surface hydrophobic) makes the surface suitable for formation of a membrane.

A method for stabilizing a membrane to a semiconductor interface comprises silanizing a semiconductor surface such that a membrane is capable of adhering to the silanized surface and separating a first fluid (e.g., on the cis side of the membrane) from a second fluid (e.g., on the trans side of the membrane) with a resistivity of, for example, at least about 10 gigaohms.

Figure 37:
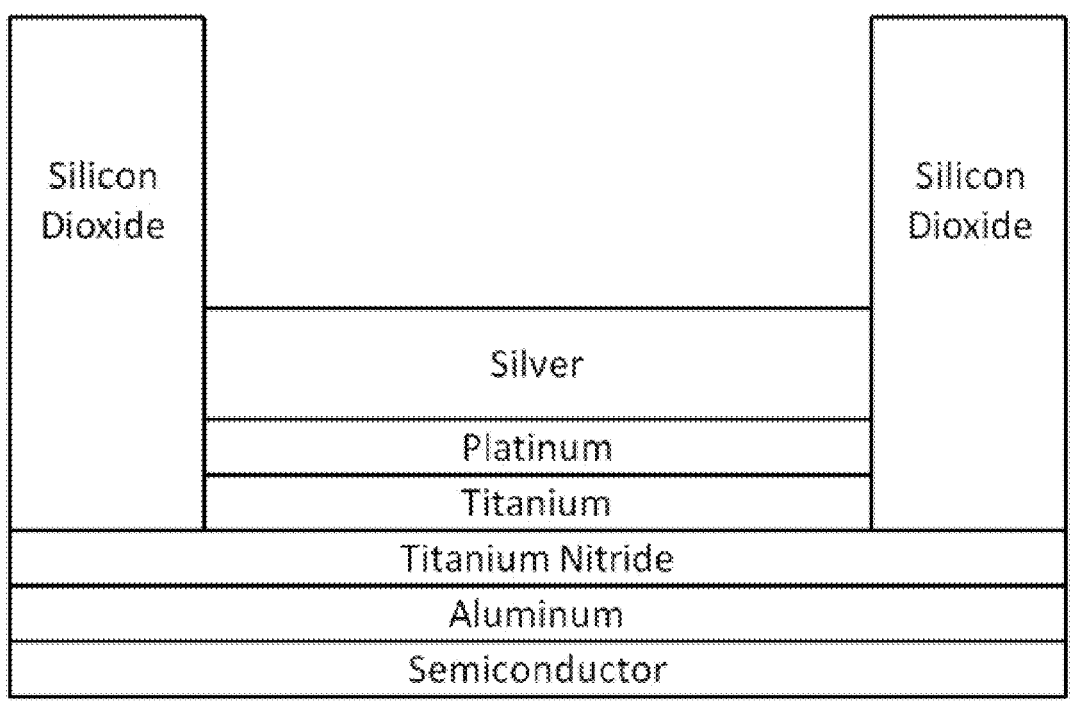
FIG. 37 shows lift off of the photo-resist and materials disposed thereupon.
Figure 38:
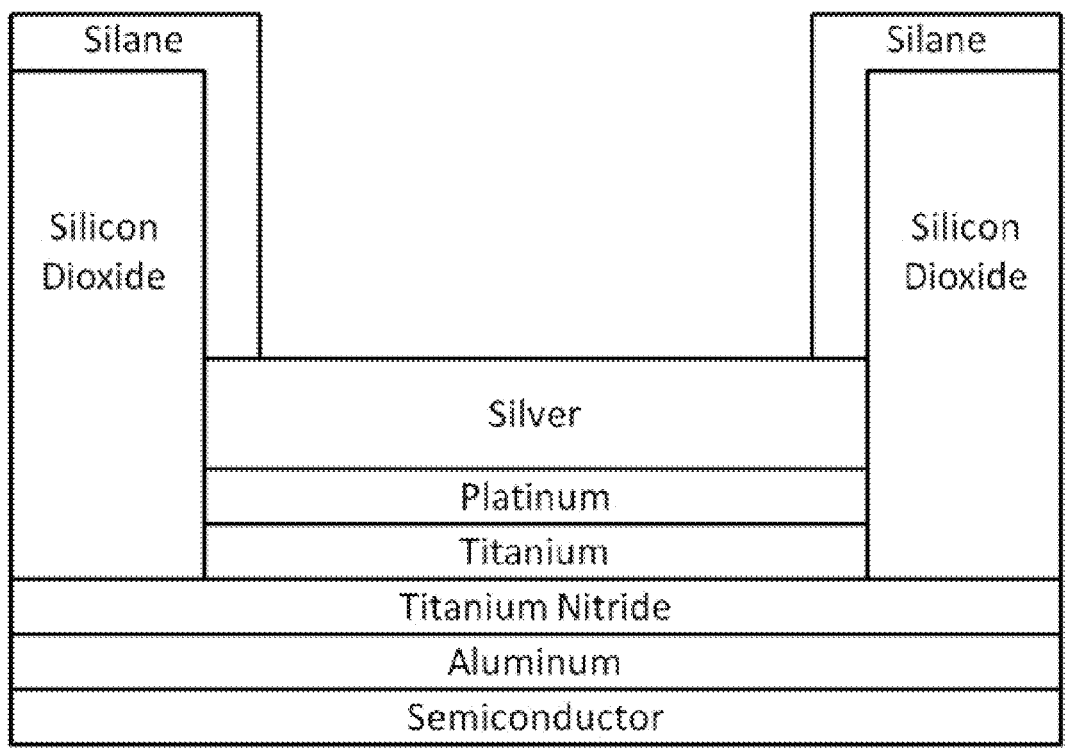
FIG. 38 shows silanization of the silicon dioxide.

A method for preparing a biochip can comprise providing a packaged biochip or biochip precursor having a surface that comprises silicon dioxide and/or metal (e.g., as shown in FIG. 37) and silanizing the surface (e.g., as shown in FIG. 38) using, for example, an organofunctional alkoxysilane molecule. In some cases, the organofunctional alkoxysilane molecule is dimethylchloro-octodecyl-silane, methyldichloro-octodecyl-silane, trichloro-octodecyl-silane, trimethyl-octodecyl-silane, triethyl-octodecyl-silane or any combination thereof.

The organofunctional alkoxysilane molecule can cover the silicon dioxide surfaces (as shown in FIG. 38) and optionally metal surfaces (not shown). The silane layer can be one molecular in thickness (FIG. 38).

Following silanization, the method can further comprise removing residual silane from the substrate with a rinsing protocol. An example rinsing protocol is a 5 second rinse with decane, acetone, ethanol, water, and ethanol followed by air drying and heating at 97° C. for 30 minutes. The rinsing protocol can also used to clean the chip prior to the application of the silane layer.

Figure 41:
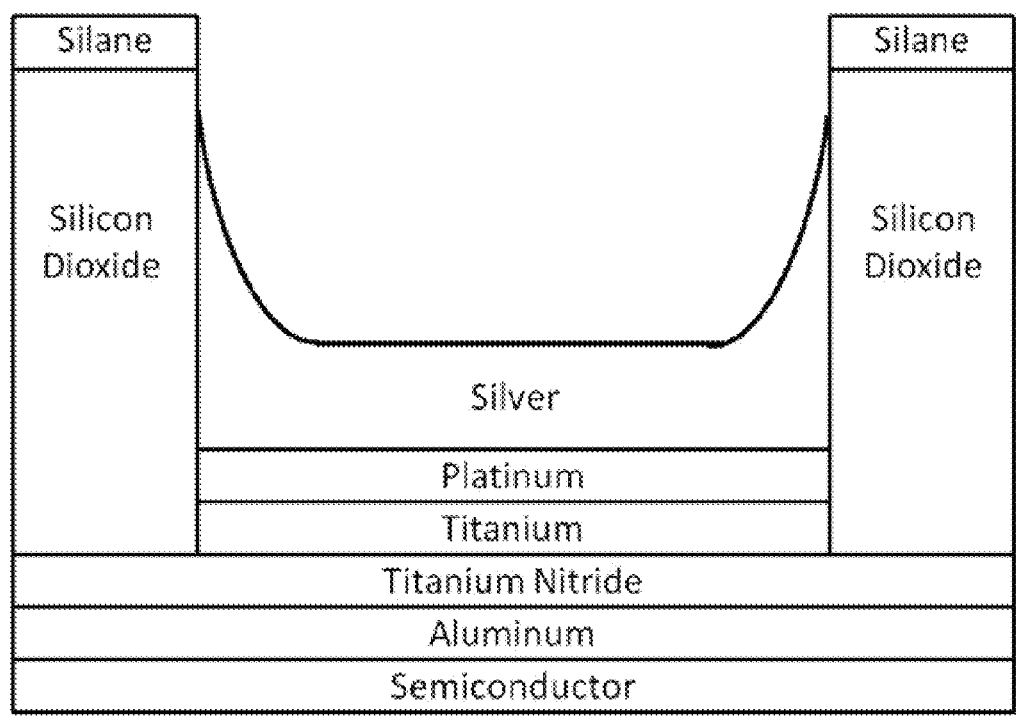
FIG. 41 shows a biochip where the silver electrode comes up on the side walls of the well.

FIG. 41 shows that the silver and protective metal underneath can sputter onto the side walls of the wells and thus the silanization may not come down into the well. In some instances, three fourths or more of the side walls of the wells are covered with silver and the protective layer underneath.

Insertion of Gel and Formation of a Membrane

In an aspect, a method comprises coating a substrate with a layer suitable for adhesion of a membrane (e.g., a lipid bilayer comprising a nanopore), where the method comprises silanizing the substrate with an organofunctional alkoxysilane molecule. FIG. 38 shows a biochip where a membrane can be disposed on the silanized surface.

Figure 39:
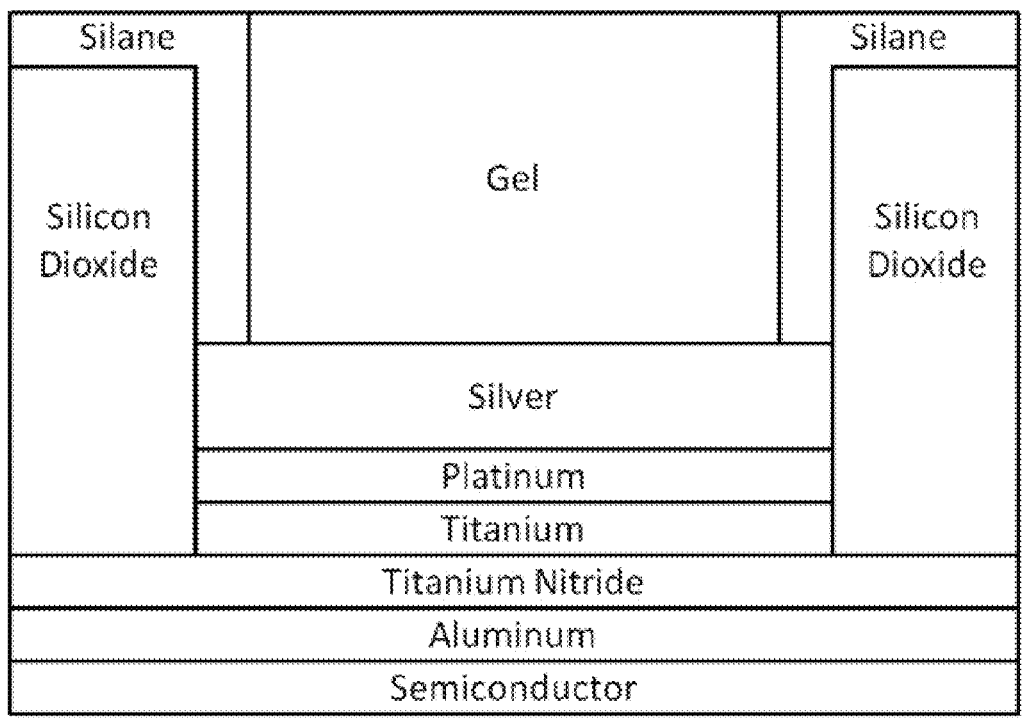
FIG. 39 shows the optional filling of the well with a gel.
Figure 40:
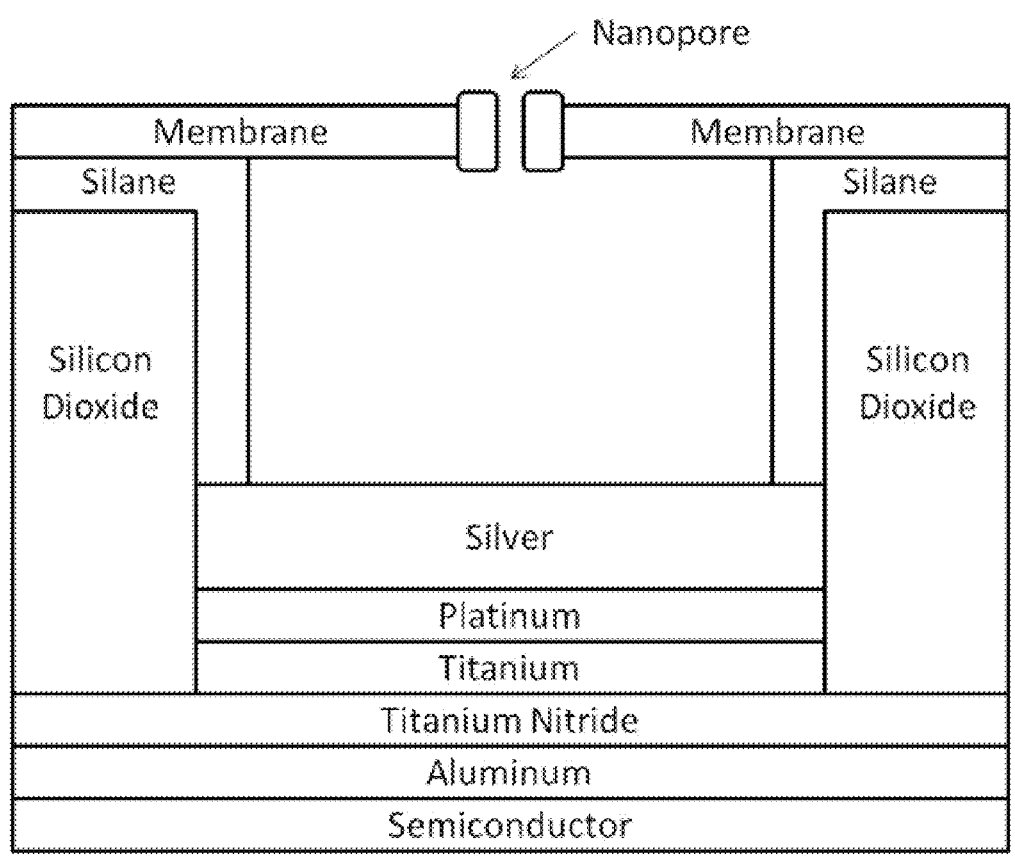
FIG. 40 shows creation of a membrane with a nanopore over the well.

In some cases, the membrane is difficult to form and/or is unstable at least in part due to the membrane being supported on the silanized silicon dioxide, but not supported over the well. It is recognized and described herein that filling the well with a gel can support the membrane over the well area, thereby making it easier to form the membrane and/or stabilizing the membrane. In some embodiments, the empty portion of a well is filled with a gel as shown in FIG. 39. The gel can provide mechanical support for a membrane disposed over the well.

In an aspect, a method for preparing a biochip comprises depositing a gel into well that is in proximity to an electrode and sensing circuit and forming a membrane over the well, where the membrane is at least partially supported by the gel.

In some cases, the gel is non-reactive, cross-linked, comprises a liquid electrolyte, or any combination thereof. Gels can include but are not limited to standard reagent gels such as agarose and commercially available proprietary gel matrixes (e.g., Collagen, Lamanin, Hydrogels, QGel, and HydroMax gels).

Insertion of a Nanopore

In some instances, a nanopore is inserted in the membrane (e.g., by electroporation). The nanopore can be inserted by a stimulus signal such as electrical stimulus, pressure stimulus, liquid flow stimulus, gas bubble stimulus, sonication, sound, vibration, or any combination thereof. The nanopore can be a protein nanopore such as alpha-hemolysin or *Mycobacterium smegmatis* (MspA) nanopore.

In some cases, a polymerase (e.g., DNA polymerase) is attached to and/or is located in proximity to the nanopore. The polymerase can be attached to the nanopore before or after the nanopore is incorporated into the membrane. In some instances, the nanopore and polymerase are a fusion protein (i.e., single polypeptide chain).

The polymerase can be attached to the nanopore in any suitable way. In some cases, the polymerase is attached to the hemolysin protein monomer and then the full nanopore heptamer is assembled (e.g., in a ratio of one monomer with an attached polymerase to 6 hemolysin monomers without an attached polymerase). The nanopore heptamer can then be inserted into the membrane.

Another method for attaching a polymerase to a nanopore involves attaching a linker molecule to a hemolysin monomer or mutating a hemolysin monomer to have an attachment site and then assembling the full nanopore heptamer (e.g., at a ratio of one monomer with linker and/or attachment site to 6 hemolysin monomers with no linker and/or attachment site). A polymerase can then be attached to the attachment site or attachment linker (e.g., in bulk, before inserting into the membrane). The polymerase can also be attached to the attachment site or attachment linker after the (e.g., heptamer) nanopore is formed in the membrane. In some cases, a plurality of nanopore-polymerase pairs are inserted into a plurality of membranes (e.g., disposed over the wells and/or electrodes) of the biochip. In some instances, the attachment of the polymerase to the nanopore complex occurs on the biochip above each electrode.

The polymerase can be attached to the nanopore with any suitable chemistry (e.g., covalent bond and/or linker). In some cases, the polymerase is attached to the nanopore with molecular staples. In some instances, molecular staples comprise three amino acid sequences (denoted linkers A, B and C). Linker A can extend from a hemolysin monomer, Linker B can extend from the polymerase, and Linker C then can bind Linkers A and B (e.g., by wrapping around both Linkers A and B) and thus the polymerase to the nanopore. Linker C can also be constructed to be part of Linker A or Linker B, thus reducing the number of linker molecules.

In some instances, the polymerase is linked to the nanopore using Solulink™ chemistry. Solulink™ can be a reaction between HyNic (6-hydrazino-nicotinic acid, an aromatic hydrazine) and 4FB (4-formylbenzoate, an aromatic aldehyde). In some instances, the polymerase is linked to the nanopore using Click chemistry (available from LifeTechnologies for example). In some cases, zinc finger mutations are introduced into the hemolysin molecule and then a molecule is used (e.g., a DNA intermediate molecule) to link the polymerase to the zinc finger sites on the hemolysin.

Systems for Forming Wells

Another aspect of the disclosure provides systems for forming wells. The system can include a deposition system, a pumping system in fluid communication with the deposition system, and a computer system (or controller) having a computer processor (also "processor" herein) for executing machine readable code implementing a method for forming the wells. The code can implement any of the methods provided herein. The pumping system can be configured to purge or evacuate the deposition system.

The deposition system can include one or more reaction spaces for forming material layers of the wells. In some situations, the deposition system is a roll-to-roll deposition system with one or more interconnected reaction chambers, which can be fluidically isolated from one another (e.g., with the aid of purging or pumping at locations in-between the chambers).

One or more deposition systems can be used to form a well. A deposition system can be configured for use with various types of deposition techniques, such as, for example, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD) and physical vapor deposition (e.g., sputter deposition, evaporative deposition). A deposition system can be configured to enable layer-by-layer formation using various semiconductor manufacturing techniques, such as photolithography.

The pumping system can include one or more vacuum pumps, such as one or more of a turbomolecular ("turbo") pump, a diffusion pump, ion pump, cryogenic ("cryo") pump, and a mechanical pump. A pump can include one or more backing pumps. For example, a turbo pump can be backed by a mechanical pump.

In some situations, an array comprising one or more wells is formed in a substrate with the aid of a deposition system. Deposition can be regulated with the aid of a controller. In some embodiments, the controller is configured to regulate one or more processing parameters, such as the substrate temperature, precursor flow rates, growth rate, carrier gas flow rate and deposition chamber pressure. The controller includes a processor configured to aid in executing machine-executable code that is configured to implement the methods provided herein. The machine-executable code is stored on a physical storage medium, such as flash memory, a hard disk, or other physical storage medium configured to store computer-executable code.

A controller can be coupled to various components of the system. For instance, the controller can be in communication with the one or more deposition systems. As another example, the controller can be in communication with the pumping system, which can enable the controller to regulate a pressure of the enclosure.

A controller can be programmed or otherwise configured to regulate one or more processing parameters, such as the substrate temperature, precursor flow rates, growth rate, carrier gas flow rate, precursor flow rate, and deposition chamber pressure. The controller, in some cases, is in communication with a valve or a plurality of valves of a deposition chamber, which aids in terminating (or regulating) the flow of a precursor in the deposition chamber. The controller includes a processor configured to aid in executing machine-executable code that is configured to implement the methods provided herein. The machine-executable code is stored on a physical storage medium, such as flash memory, a hard disk, or other physical storage medium configured to store computer-executable code.

Methods for forming lipid bilayers, inserting nanopores in lipid bilayers, and sequencing nucleic acid molecules can be found in PCT Patent Publication No. WO2011/097028, which is incorporated herein by reference in its entirety. In some cases, the membrane is formed with aid of a bubble and the nanopore is inserted in the membrane with aid of an electrical stimulus.

The present disclosure provides various users of biochips. Biochips of the present disclosure can be used for atomic or molecular sensing, such as sensing an analyte, or sequencing, such as nucleic acid sequencing. Devices of the present disclosure can be used to determine the presence of methylated nucleic acid bases in a sequence of nucleic acid bases.

The biochips described herein can be used to determine the effect of drugs or any man-made or naturally occurring molecule on the stability or performance of trans-membrane proteins or membrane bound proteins. The detector can be set up by creating an array (e.g., greater than 2) of individually addressable and electrically detectable artificial electrode or cell membranes containing any number of pre-selected or unknown trans-membrane proteins over electrodes that are each sealed with the membrane-like bilayer. Any trans-membrane protein whose presence can be detected ionically or electrically can be inserted into the lipid bilayer and the effects of chemicals, drugs, and any biological or man-made molecule on the stability or performance of these trans-membrane proteins can be sensed and detected.

The biochips described herein can be used to determine the effect of drugs or any man-made or natural molecules on the stability or performance of different membranes placed over different portions of the array sensor. By using the channels defined in the drawings of this application different lipid bilayer materials can be directed to different areas of the array chip, and a plurality of different lipid membranes can be presented to a test solution, each membrane type present at a known location. The ability of drugs to influence membrane types or any man-made or naturally occurring molecule to effect the different membranes can be detected.

The biochips described herein can be used to detect the presence of, capture, sort, and bin specific proteins or specific biomolecules in an unknown solution.

The biochips and methods of making and using biochips described herein can use an electrolyte solution. In some cases, the ions in the electrolyte solution flow through the nanopore and are detected by the electrode. In cases where the electrode is a sacrificial electrode (i.e., depleted during detection, e.g., silver) the electrode can last relatively longer when the electrolyte comprises some salts rather than others. In some embodiments, the electrolyte does not comprise potassium ion (e.g., because potassium ion results in a relatively shorter electrode life). In some embodiments, the electrolyte comprises lithium chloride, tetramethylammonium chloride, triethylammonium chloride, ammonium chloride, or any combination thereof (e.g., because the listed salts result in a relatively shorter electrode life).

Biochips of the disclosure can perform sensing measurements with the aid of resistive, inductive or capacitive sensing. In some cases, a biochip comprises an electrode that can sense a capacitance of a membrane adjacent to the electrode upon interaction of the membrane or a nanopore in the membrane with a species adjacent or in proximity to the membrane or the nanopore. Such measurements can be made with the aid of an applied alternating current (AC) waveform or a direct current (DC) waveform.

EXAMPLES

Example 1

Nucleic Acid Sequencing with a Chip Having 500 Sites Per 1 mm$^2$

A chip is provided that has a plurality of discrete sites at a density greater than or equal to about 500 sites per 1 mm$^2$. An individual site of the plurality of discrete sites has at least one nanopore formed in a membrane disposed adjacent to an electrode. Each discrete site is adapted to aid in the detection of the nucleic acid molecule. Each discrete site is independently addressable.

A plurality of nucleic acid molecules are directed to the plurality of discrete sites and characterized with the aid of a computer processor coupled to the discrete sites. A nucleic acid sequence of each of the nucleic molecules is determined based on electrical signals received from the plurality of discrete sites.

Example 2

Nucleic Acid Sequencing with an Accuracy of at Least 97%

A chip is provided that has an array of individual sensors. An individual sensor of the array has an electrode that is disposed adjacent to a membrane having a nanopore. The electrode is coupled to an electrical circuit that is adapted to generate an electrical signal to aid in the detection of the nucleic acid molecule upon the flow of the nucleic acid molecule or portion thereof through or in proximity to the nanopore. The electrode and, hence, the individual sensor are independently addressable.

A nucleic acid molecule is directed through or in proximity to the nanopore. Nucleic acid sequence information (raw read) is obtained from the individual sensor and stored in computer memory. Raw reads are obtained from other individual sensors concurrently and stored in the computer memory. The raw reads are generated from copies of the nucleic acid molecule. As such, this process generates redundant sequence information which can be used for error analysis. A computer system in communication with the chip has software that performs error analysis on the raw reads and eliminates erroneous raw reads. The computer system then generates a nucleic acid sequence of the nucleic acid molecule at an accuracy of at least about 97%. In some examples, the computer system aligns the nucleic acid sequence with the nucleic acid sequence of other nucleic acid molecules as part of a larger nucleic acid sample, and generates a sequence of the nucleic acid sample at an accuracy of at least about 97%.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A device for use in molecular sensing comprising one or more nanopores in a membrane disposed upon at least one membrane incompatible surface in sensing proximity to an electrode coupled to an integrated circuit, wherein said membrane comprising said one or more nanopores exhibits a capacitance greater than about 5 fF/µm2 and a conductance less than about 10 nano Siemens per mole of electrolyte per nanopore as measured by said electrode under an applied voltage of at least about 50 mV.

2. The device of claim 1, wherein said integrated circuit is an individually addressable integrated circuit.

3. The device of claim 1, wherein said integrated circuit comprises a logic controller.

4. A method for sequencing a nucleic acid molecule, comprising:
   (a) providing a chip comprising an array of sensors, wherein an individual sensor of said array of sensors comprises a membrane adjacent to a sensing electrode, wherein said membrane comprises at least one nanopore configured to aid in the detection of one or more nucleic acid bases of said nucleic acid molecule or portion thereof upon the flow of said nucleic acid molecule or portion thereof through or adjacent to said at least one nanopore;
   (b) directing said nucleic acid molecule to said individual sensor;
   (c) applying a series of electrical pulses to said membrane upon directing said nucleic acid molecule to said individual sensor; and
   (d) detecting one or more nucleic acid bases of said nucleic acid molecule or portion thereof between said series of electrical pulses.

5. A method for sequencing a nucleic acid molecule, comprising:
   (a) providing a chip comprising an array of individual sensors, wherein an individual sensor of said array comprises an electrode that is disposed adjacent to a membrane having a nanopore therein, wherein said electrode is coupled to an electrical circuit that is adapted to generate an electrical signal to aid in the detection of said nucleic acid molecule or a portion thereof upon the flow of said nucleic acid molecule or portion thereof through or in proximity to said nanopore;
   (b) directing said nucleic acid molecule or portion thereof through or in proximity to said nanopore; and
   (c) identifying a nucleic acid sequence of said nucleic acid molecule or portion thereof at an accuracy of at least about 97%.

6. The method of claim 5, wherein said nucleic acid sequence is generated with the aid of a computer processor coupled to said electrical circuit.

7. The method of claim 5, wherein said individual sensor is independently addressable.

8. The method of claim 5, wherein said nucleic acid molecule comprises a tag that is detected by said nanopore upon the incorporation of complementary nucleic acid bases into said nucleic acid molecule.

9. The method of claim 5, wherein said nucleic acid sequence of said nucleic acid molecule or portion thereof is identified by combining data collected from at least 10 passes of said nucleic acid molecule or portion thereof through or in proximity to said nanopore.

10. The method of claim 9, wherein said nucleic acid sequence of said nucleic acid molecule or portion thereof is identified by combining data collected from at least 20 passes of said nucleic acid molecule or portion thereof through or in proximity to said nanopore.

11. A system for sequencing a nucleic acid molecule, comprising:
   (a) a chip comprising an array of individual sensors, wherein an individual sensor of said array comprises an electrode that is disposed adjacent to a membrane having a nanopore therein, wherein said electrode is coupled to an electrical circuit that is adapted to generate an electrical signal to aid in the detection of said nucleic acid molecule or a portion thereof upon the flow of said nucleic acid molecule or portion thereof through or adjacent to said nanopore; and
   (b) a processor coupled to said chip, wherein said processor is programmed to aid in characterizing a nucleic acid sequence of said nucleic acid molecule based on electrical signals received from said plurality of discrete sites at an accuracy of at least about 97%.

12. A system for sensing a biological sample from a subject, the system comprising:
   a) a housing;
   b) a sensor within the housing, the sensor having an electrical circuit adjacent to a membrane with a nanopore therein, wherein the electrical circuit is adapted to generate an electrical signal in response to the biological sample flowing through or adjacent to the nanopore; and
   c) an identification member on or within the housing, the identification member having a unique identifier associated with the system and adapted to aid in associating the electrical signal, or characteristic information derived from the electrical signal, with the subject.

13. A method for manipulating a fluid on a surface, comprising:
   (a) providing a surface, an array of electrodes in proximity to the surface, and a fluid comprising a hydrophilic phase and a hydrophobic phase, wherein said hydrophobic phase is adjacent to said surface; and
   (b) energizing the electrodes in a spatial and/or temporal pattern, thereby decreasing a volume of said hydrophobic phase in relation to said hydrophilic phase in proximity to said electrodes.

14. A biochip, comprising a nanopore in a membrane that is disposed within, adjacent to, or in proximity to a well, wherein the well comprises an electrode that is capable of detecting a change in the flow of ions through said nanopore in response to a species passing through, in proximity to, or adjacent to the nanopore, wherein said electrode is capable of detecting said change in the flow of ions for at least 1 hour without re-adjusting the ion concentrations on either side of the membrane.

15. A method for forming a biochip, the method comprising:
   (a) providing a semiconductor substrate;
   (b) forming a plurality of wells in said semiconductor substrate at a density of at least 500 wells/mm2;
   (c) forming an electrode in an individual well of said plurality, wherein said electrode is capable of performing electrical measurements of detectable species that are disposed on or adjacent to the semiconductor substrate, and wherein said electrode has an operating life of at least 15 minutes with 40 mV applied potential; and
   (d) preparing the substrate for the formation of a membrane that seals the individual well at a resistivity of at least about 10 gigaohms.

* * * * *